(12) United States Patent
Hergenrother et al.

(10) Patent No.: US 11,691,967 B2
(45) Date of Patent: Jul. 4, 2023

(54) ANTIBIOTICS EFFECTIVE FOR GRAM-NEGATIVE PATHOGENS

(71) Applicant: The Board of Trustees of the University of Illinois, Urbana, IL (US)

(72) Inventors: Paul J. Hergenrother, Champaign, IL (US); Emily Jane Geddes, Urbana, IL (US); Bryon Shane Drown, Champaign, IL (US); Stephen E. Motika, Urbana, IL (US); Erica Nicole Parker, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/980,022

(22) PCT Filed: Mar. 11, 2019

(86) PCT No.: PCT/US2019/021622
§ 371 (c)(1),
(2) Date: Sep. 11, 2020

(87) PCT Pub. No.: WO2019/177975
PCT Pub. Date: Sep. 19, 2019

(65) Prior Publication Data
US 2021/0017165 A1   Jan. 21, 2021

Related U.S. Application Data

(60) Provisional application No. 62/641,708, filed on Mar. 12, 2018.

(51) Int. Cl.
| | | |
|---|---|---|
| C07D 409/14 | (2006.01) | |
| C07D 471/04 | (2006.01) | |
| C07D 519/00 | (2006.01) | |
| A61P 31/04 | (2006.01) | |

(52) U.S. Cl.
CPC ............ *C07D 409/14* (2013.01); *A61P 31/04* (2018.01); *C07D 471/04* (2013.01); *C07D 519/00* (2013.01)

(58) Field of Classification Search
CPC .. C07D 409/14; C07D 471/04; C07D 519/00; A61P 31/04
See application file for complete search history.

(56) References Cited

U.S. PATENT DOCUMENTS

| | | |
|---|---|---|
| 7,250,424 B2 | 7/2007 | Burgess et al. |
| 8,263,613 B2 | 9/2012 | Pauls et al. |
| 8,901,105 B2 | 12/2014 | Partridge et al. |
| 2006/0142265 A1 | 6/2006 | Berman et al. |
| 2008/0125423 A1 | 5/2008 | Miller et al. |
| 2009/0156578 A1 | 6/2009 | Pauls et al. |
| 2011/0098277 A1 | 4/2011 | Burgess et al. |
| 2011/0124633 A1 | 5/2011 | Berman et al. |

FOREIGN PATENT DOCUMENTS

| | | |
|---|---|---|
| WO | 2001027103 A1 | 4/2001 |
| WO | 2004052890 A1 | 6/2004 |
| WO | 2004082586 A2 | 9/2004 |
| WO | 2013021054 A1 | 2/2013 |
| WO | 2017156519 A1 | 9/2017 |

OTHER PUBLICATIONS

Hermann, T., "Antibiotic Tricks a Switch," Nature, 526:650-651, Oct. 2015.
International Search Report and Written Opinion of the ISA/US in PCT/US2019/021622, dated Jul. 17, 2019; 18pgs.
Margalit et al., "Targeting Cell Division: Small-molecule Inhibitors of FtsZ GTPase Perturb Cytokinetic Ring Assembly and Induce Bacterial Lethality," Proc Natl Acad Sci U S A., 101(32):11821-11826, Aug. 2004.
Nepomuceno et al., "Synthesis and Evaluation of Quinazolines as Inhibitors of the Bacterial Cell Division Protein FtsZ," ACS Med. Chem. Lett., 6(3):308-312, Jan. 2015.
Richter et al., "Predictive Compound Accumulation Rules Yield a Broad-Spectrum Antibiotic," Nature, 545(7654):299-304, May 2017.
Sampson et al., "Spiro-naphthyridinone Piperidines as Inhibitors of *S. aureus* and *E. coli* enoyl-ACP Reductase (FabI)," Bioorg Med Chem Lett., 19(18), Abstract, 2 pgs., Sep. 2009.
Wang et al., "Dual-Targeting Small-Molecule Inhibitors of the *Staphylococcus aureus* FMN Riboswitch Disrupt Riboflavin Homeostasis in an Infectious Setting," Cell Chem Biol., 24(5):576-588, May 2017.

*Primary Examiner* — Brandon J Fetterolf
*Assistant Examiner* — Lauren Wells
(74) *Attorney, Agent, or Firm* — Haukaas Fortius PLLC; Michael Haukaas

(57) ABSTRACT

Disclosed herein are antibacterial compounds that accumulate in Gram-negative bacteria, methods of preparing the compounds, and methods of using the compounds to inhibit or kill microbes, and methods of treating microbial infections, such as Gram-negative bacterial infections. Compounds selected for conversion to potential Gram-negative antibacterial compounds were identified based on compounds having low globularity and low flexibility. Amine substituents were then strategically added to the selected compounds to provide compounds having antibacterial activity against Gram-negative bacteria.

15 Claims, 16 Drawing Sheets
Specification includes a Sequence Listing.

| Bacterial Strain | MIC (µg/mL) | | |
| --- | --- | --- | --- |
| | Debio-1452 | Debio-1452-NH3 | 8 |
| WT Gram-positive | | | |
| S. aureus ATCC29213 | 0.008 | 0.03 | 0.016 |
| Gram-negative permeability mutant | | | |
| E. coli ΔtolC JW5503 | 0.031 | 0.062 | 0.125 |
| E. coli ΔfabC | 0.5 | 0.25 | 0.25 |
| WT Gram-negative | | | |
| E. coli MG1655 | >32 | 4 | >32 |
| E. coli BAA-2340 | >32 | 4 | >32 |
| E. coli AR-0493 | >32 | 4 | >32 |
| E. cloacae ATCC 29893 | >32 | 8 | >32 |
| K. pneumoniae BAA-1705 | >32 | 8 | >32 |
| K. pneumoniae S47889 | >32 | 8 | >32 |
| A. baumannii W41979 | >32 | 4 | >32 |
| A. baumannii F19521 | >32 | 4 | >32 |
| P. aeruginosa PA01 | >32 | >64 | >32 |

*Fig. 2*

Molecule Submission

Single Molecule

6DNM

CC(C1=C2C(OCC3)=C(N3C(C=C4C)=O)C4=C1)=CC(N2C)=O

Submit Molecule

Batch Submission

Batch name

Pick a SMILES list

Choose File  No file chosen

Submit Batch

MOLECULES:

PENICILLIN G

No Primary Amine

Low Globularity

Low Flexibility

| | |
|---:|:---|
| SMILES | CC1(C)[C@H](C(O)=O)N2C([C@@H](NC(CC3=CC=CC=C3)=O)[C@@]2([H])S1)=O |
| Job status | Complete |
| Formula | C16H18N2O4S |
| Mol. Wt. | 334.39 |
| Rotatable bonds | 4 |
| Globularity | 0.129 |
| PBF | 1.138 |
| Functional Group | No Amine |

AMPICILLIN

| | |
|---|---|
| SMILES | CC1([C@@H](N(C2=O)[C@@]([C@@]2(NC([C@@H](C3=CC=CC=C3)N)=O)[H])(S1)[H])C(O)=O)C |
| Job status | Complete |
| Formula | C16H19N3O4S |
| Mol. Wt. | 349.4 |
| Rotatable bonds | 4 |
| Globularity | 0.101 |
| PBF | 1.011 |
| Functional Group | Primary Amine |

6DNM-NH3

Primary Amine

Low Globularity

Low Flexibility

| | |
|---:|:---|
| SMILES | CC(C1=C2C(OCC3CN)=C(N3C(C=C4C)=O)C4=C1)=CC(N2C)=O |
| Job status | Complete |
| Formula | C18H19N3O3 |
| Mol. Wt. | 325.36 |
| Rotatable bonds | 1 |
| Globularity | 0.068 |
| PBF | 0.549 |
| Functional Group | Primary Amine |

6DNM

No Primary Amine

Low Globularity

Low Flexibility

| | |
|---:|:---|
| SMILES | CC(C1=C2C(OCC3)=C(N3C(C=C4C)=O)C4=C1)=CC(N2C)=O |
| Job status | Complete |
| Formula | C17H16N2O3 |
| Mol. Wt. | 296.32 |
| Rotatable bonds | 0 |
| Globularity | 0.034 |
| PBF | 0.294 |
| Functional Group | No Amine |

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: SYNTHETIC PRIMER

<400> SEQUENCE: 1
ggggccagcg tttctttttc          20

<210> SEQ ID NO 2
<211> LENGTH: 20
<212> TYPE: DNA
<213> ORGANISM: Artificial Sequence
<220> FEATURE:
<223> OTHER INFORMATION: SYNTHETIC PRIMER

<400> SEQUENCE: 2
aaacatggag acggtgctgg          20

<210> SEQ ID NO 3
<211> LENGTH: 20
<212> TYPE: DNA
<213> ORGANISM: Artificial Sequence
<220> FEATURE:

<223> OTHER INFORMATION: SYNTHETIC PRIMER

<400> SEQUENCE: 3
atagctactc acagccaggt                                              20

<210> SEQ ID NO 4
<211> LENGTH: 20
<212> TYPE: DNA
<213> ORGANISM: Artificial Sequence
<220> FEATURE:
<223> OTHER INFORMATION: SYNTHETIC PRIMER

<400> SEQUENCE: 4 gaagggaga aagacggatc                                               20

<210> SEQ ID NO 5
<211> LENGTH: 26
<212> TYPE: DNA
<213> ORGANISM: Artificial Sequence
<220> FEATURE:
<223> OTHER INFORMATION: SYNTHETIC PRIMER

<400> SEQUENCE: 5
ttcaaaattg tccacgacat cagctc                                       26

<210> SEQ ID NO 6
<211> LENGTH: 18
<212> TYPE: DNA
<213> ORGANISM: Artificial Sequence
<220> FEATURE:
<223> OTHER INFORMATION: SYNTHETIC PRIMER

<400> SEQUENCE: 6
gccttcacgg gtaacggc                                                18

<210> SEQ ID NO 7
<211> LENGTH: 21
<212> TYPE: DNA
<213> ORGANISM: Artificial Sequence
<220> FEATURE:
<223> OTHER INFORMATION: SYNTHETIC PRIMER

<400> SEQUENCE: 7 ttcctaccttt agcgctgagc g                                           21

<210> SEQ ID NO 8
<211> LENGTH: 18
<212> TYPE: DNA
<213> ORGANISM: Artificial Sequence
<220> FEATURE:
<223> OTHER INFORMATION: SYNTHETIC PRIMER

<400> SEQUENCE: 8
agggtcagca gggcagaa                                                18

ANTIBIOTICS EFFECTIVE FOR GRAM-NEGATIVE PATHOGENS

RELATED APPLICATIONS

This application is a National Stage filing under 35 U.S.C. § 371 of International Application No. PCT/US2019/021622 filed Mar. 11, 2019, which claims priority under 35 U.S.C. § 119(e) to U.S. Provisional Patent Application No. 62/641,708 filed Mar. 12, 2018, each of which is incorporated herein by reference in its entirety.

GOVERNMENT SUPPORT

This invention was made with government support under Grant Nos. R01 GM118575 and R01 AI136773 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Feb. 15, 2023, is named 500.102US1 SEQUENCE LISTING_ST25.txt and is 1820 bytes in size.

BACKGROUND OF THE INVENTION

Drug-resistant bacteria are a major public health concern, with Gram-negative bacteria particularly troubling as they are insensitive to many commonly used antibiotics. Exacerbating this problem is the fact that a new class of antibiotics active against Gram-negative bacteria has not been introduced into the clinic since the quinolones in 1968. This void in discovery is not due to a lack of effort; as one example, in 2007 GlaxoSmithKline reported screening ~500,000 synthetic compounds for whole cell activity against *Escherichia coli*, but no tractable hits were identified.

The difficulty of killing Gram-negative pathogens is largely attributed to the structure of their outer membranes. Gram-negative bacteria possess two cellular membranes, with the outer membrane allowing only very slow passive diffusion of small molecules. Once inside the cell, small molecules are susceptible to efflux pumps; thus, in order to accumulate in Gram-negatives, small molecules must cross the outer membrane at a faster rate than they are pumped out. In order to accumulate to a level sufficient for activity, small molecules typically must cross the outer-membrane via channel proteins called porins, which are narrow β-barrels lined with charged amino acids that serve as selective gateways to entry for many small molecule antibiotics.

For many Gram-negative species, antibiotics enter through general porins such as OmpF, the prototypical porin of *E. coli*. Although general porins are wider than typical substrate specific channels, most contain a relatively narrow constriction zone, limiting the size of small molecules capable of diffusing through. For example, the constriction zone of OmpF is approximately 7×11 Å, which is believed to restrict passive diffusion of small molecules to an estimated 600 Da.

Central to the problem of Gram-negative antibiotic discovery is a limited understanding of the physicochemical properties that enable small molecule accumulation in Gram-negative bacteria, with current knowledge based largely on retrospective analyses of known antibiotics, and free energy calculations of small molecule permeation across the outer membrane. In 2008 O'Shea and Moser reported that antibiotics effective against Gram-negative pathogens almost always have a molecular weight (MW) less than 600 Da and tend to be very polar as measured by C log $D_{7.4}$, observations consistent with porin architecture. Retrospective studies by others have re-enforced these observations that Gram-negative active compounds tend to be small and highly polar. However, there are a number of antibiotics that meet these polarity and size criteria but are inactive against Gram-negative species, suggesting these properties do not fully encompass the determinants for small molecule accumulation.

Additionally, retrospective analyses are highly skewed by the over-representation of certain drug classes. For example, an analysis by AstraZeneca showed that carboxylic acids are present on up to 40% of Gram-negative active compounds in their collection; however, these carboxylic-acid-containing compounds are almost exclusively β-lactams. While a handful of compound accumulation studies in whole cells have been performed, broad conclusions cannot be drawn from these small data sets (10-20 compounds and all within a single structural class). Perhaps most importantly, the canonical view about the importance of C log $D_{7.4}$ and MW for Gram-negative activity has not led to general strategies to convert Gram-positive-only compounds into broad-spectrum antibiotics. The seminal observation over 50 years ago that derivatizing penicillin G into ampicillin results in broad-spectrum activity has not been generalizable, and important classes of experimental therapeutics and FDA-approved antibiotics have coverage only against Gram-positive organisms despite intensive derivatization efforts.

Therefore, there exists a need for novel Gram-negative antibiotics and methods of use thereof.

SUMMARY

In one aspect, provided herein are novel compounds of any one of Formulas I, II, III, IV, V, or a pharmaceutically acceptable salt thereof.

In another aspect, provided herein is a method of antimicrobial treatment, comprising, administering to a subject in need thereof a therapeutically effective amount of a compound of any one of Formulas I, II, III, IV, V, or a pharmaceutically acceptable salt thereof, thereby killing or inhibiting the growth of at least a portion of a plurality of microorganisms in the subject.

In another aspect, provided herein is a method of antimicrobial treatment, comprising providing a sample comprising a plurality of microorganisms; and contacting the sample with a compound disclosed herein; thereby killing or inhibiting the growth of at least a portion of the plurality of microorganisms in the sample.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2. Antimicrobial activity of Debio-1452 and derivatives. MIC values were determined using the micro-dilution broth method as outlined by the Clinical and Laboratory Standards Institute (clsi.org/). All experiments were performed in biological triplicate.

DETAILED DESCRIPTION

Figure 1:
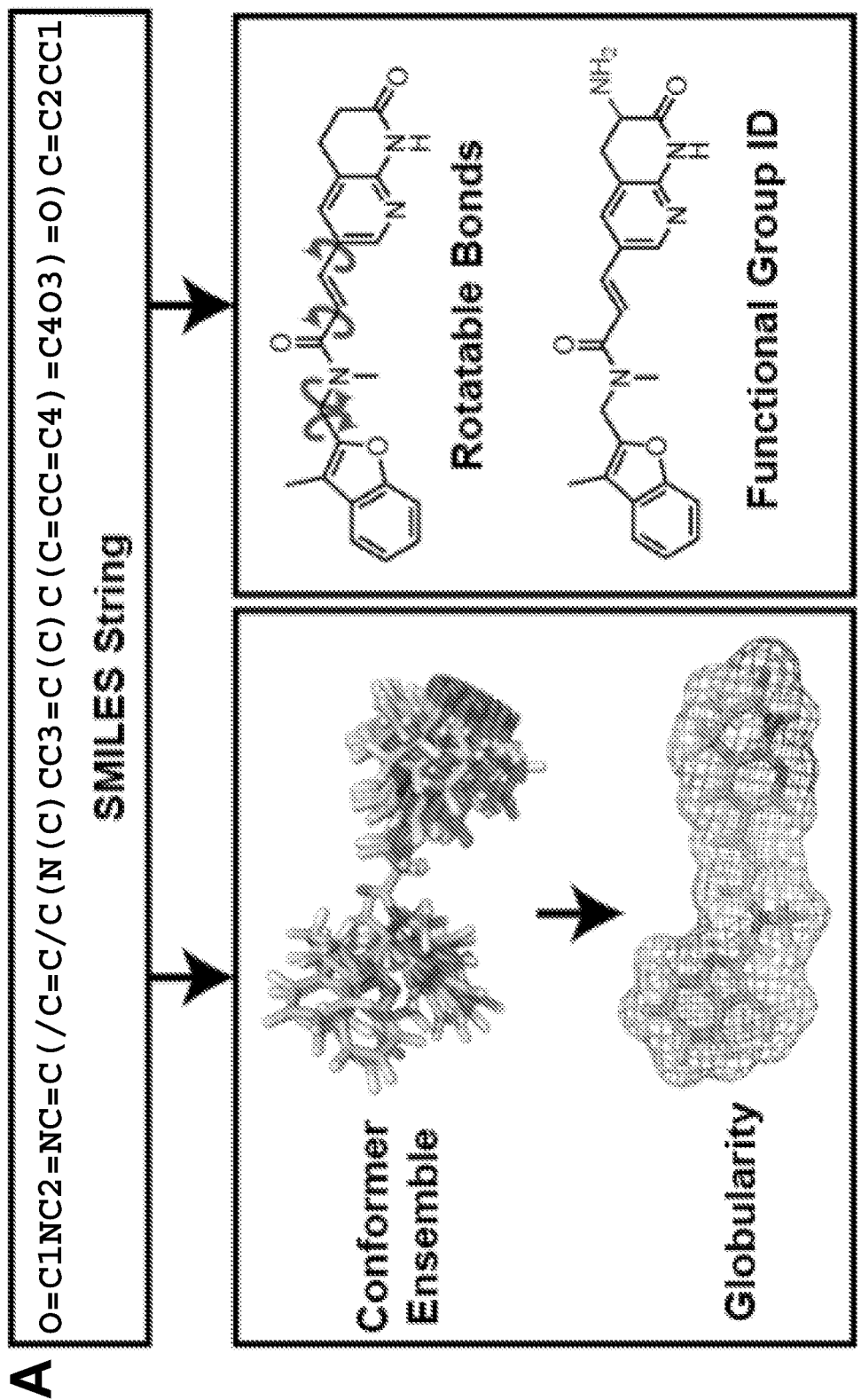
FIG. 1. A. Overview of eNTRyway molecule processing. Molecules are submitted as SMILES strings, and after an initial estimate of the 3D structure, a conformer space is systematically explored from which an average globularity is calculated. Particular functional groups and number of rotatable bonds are determined directly from 2D structure. B. Physiochemical properties of existing Gram-positive-only antibiotics, Debio-1452 is indicated with red arrow. C. Solvent exposure of the naphthyridinone of Debio-1452 when bound to *S. aureus* FabI (PDB: 4FS3) suggests sites for modification. D. Molecular docking of amine-containing derivative, Debio-1452-NH3. Additional derivative docking and docking scores are shown in Table 2.
Figure 1:
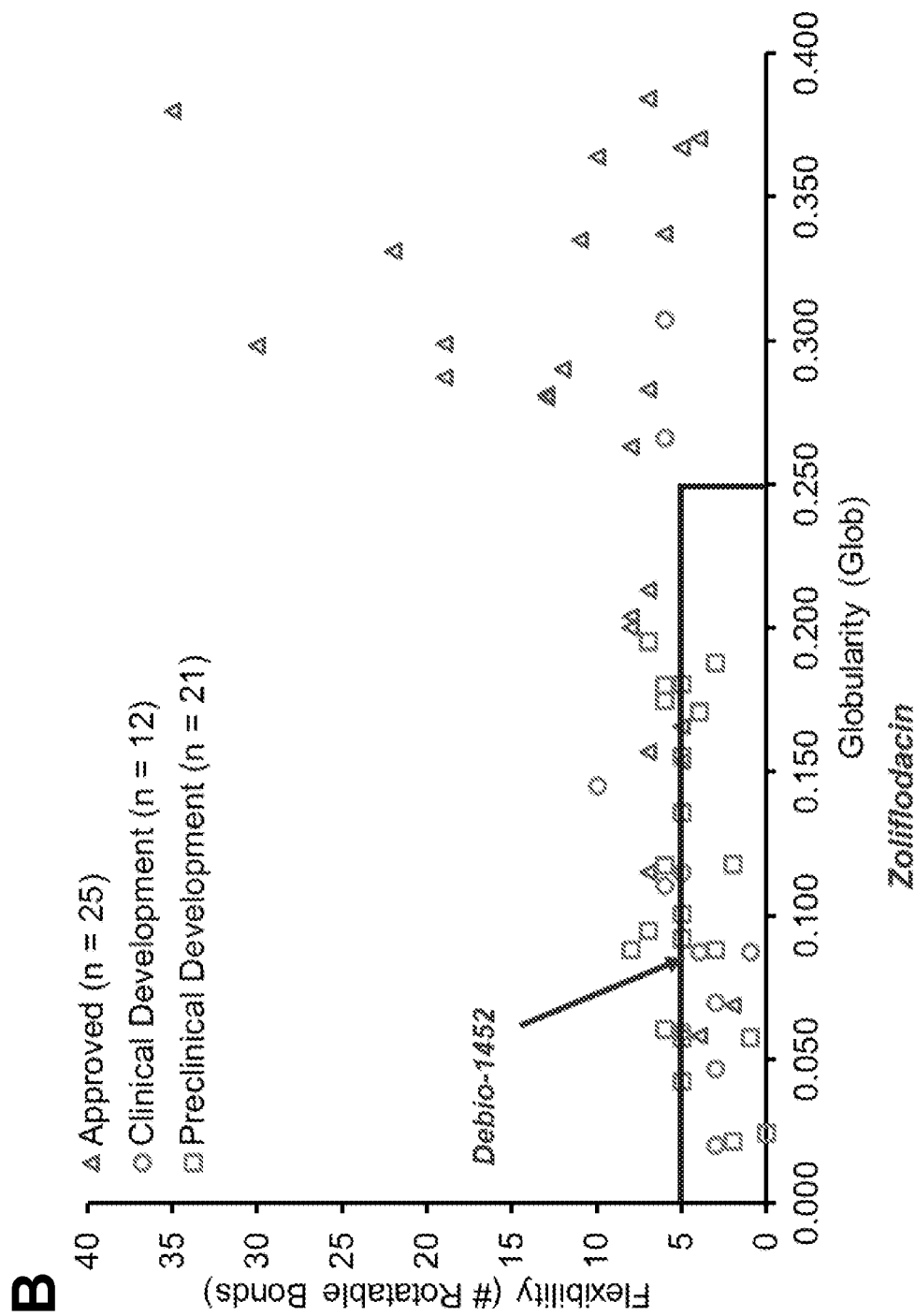
Figure 1:
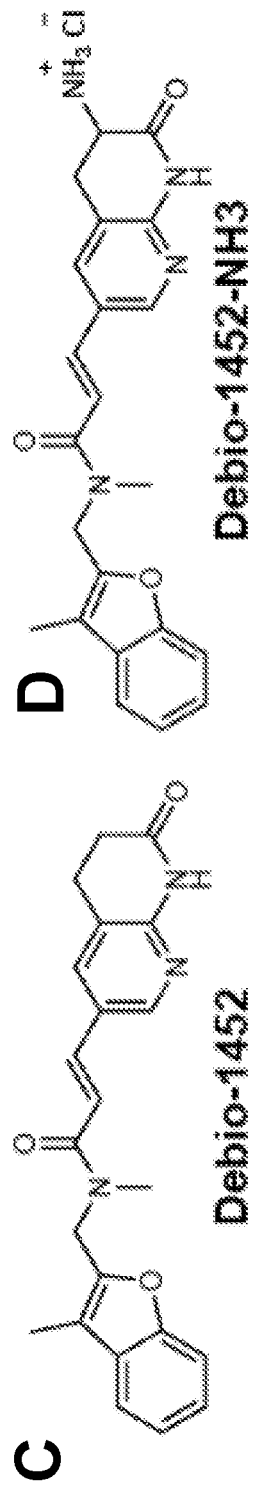
Figure 1:
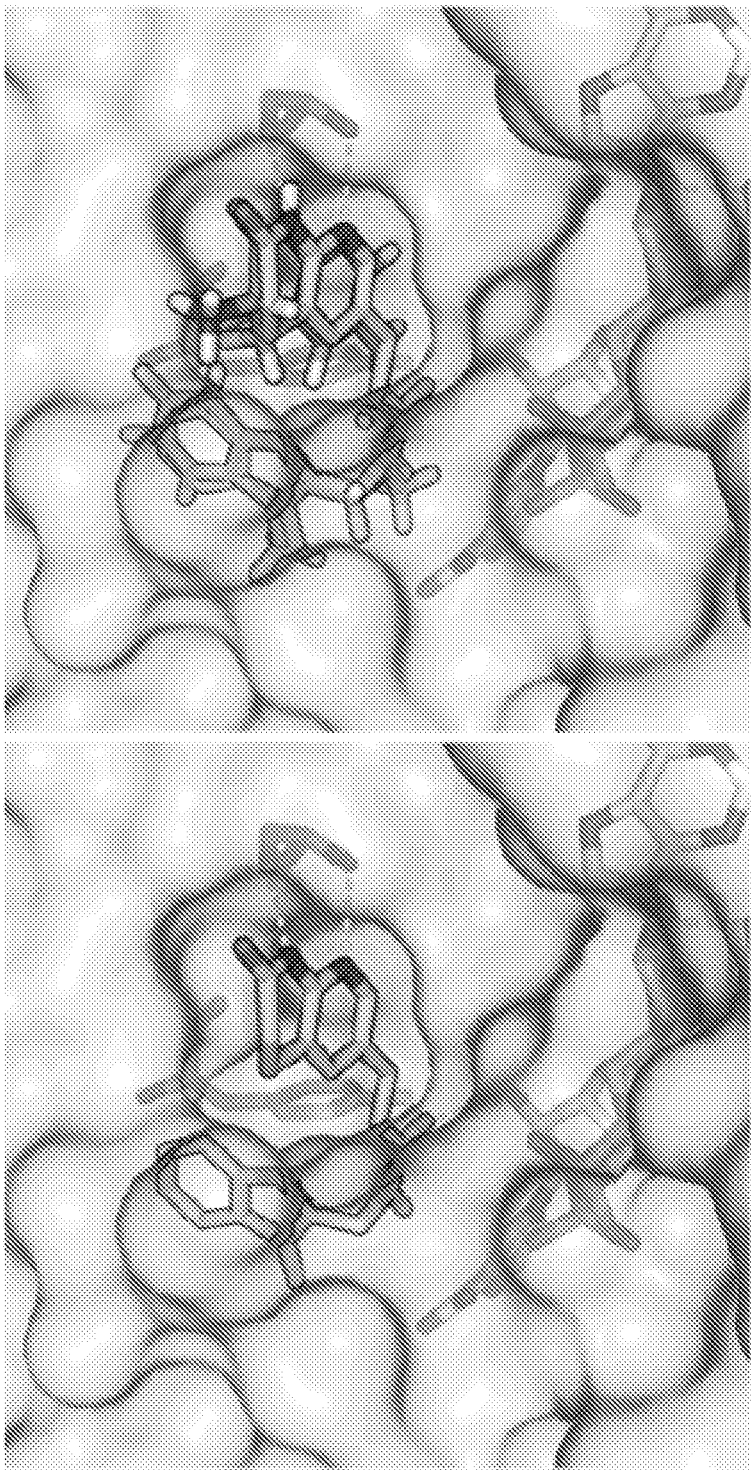

The canonical view about the importance of highly polar molecules with a molecular weight less than 600 Da for Gram-negative activity has not led to general strategies to convert Gram-positive-only compounds into broad-spectrum antibiotics. The seminal observation over 50 years ago that derivatizing penicillin G into ampicillin results in broad-spectrum activity has not been generalizable, and important classes of experimental therapeutics and FDA-approved antibiotics have coverage only against Gram-positive organisms despite intensive derivatization efforts. Described herein are novel compounds and methods of use thereof as antibiotics having effective Gram-negative activity.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983).

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this disclosure, the heteroatoms, such as nitrogen, may have hydrogen substituents and/or any permissible substituents of organic compounds described herein which satisfy the valencies of the heteroatoms.

For example, the terms "substituted", "substitution", or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound, e.g., which does not spontaneously undergo transformation such as by rearrangement, cyclization, elimination, etc. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SW, SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof. Such as racemic mixtures, form part of the present invention. Many organic compounds exist in optically active forms, i.e., they have the ability to rotate the plane of plane-polarized light. In describing an optically active compound, the prefixes D and L, or Rand S. are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "heteroatom" is art-recognized and refers to an atom of any element other than carbon or hydrogen. Illustrative heteroatoms include boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. For example, ($C_1$-$C_6$)alkyl. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths but with at least two carbon atoms. Preferred alkyl groups are lower alkyls. In preferred embodiments, a substituent designated herein as alkyl is a lower alkyl.

The term "aralkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "carboxy" as used herein, means a —$CO_2H$ group.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "amido" as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "aryl" as used herein includes 5-, 6- and 7-membered aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. Also, "DCM" stands for dichloromethane; "rt" stands for room temperature, and may mean about 20° C., about 21° C., about 22° C., about 23° C., about 24° C., about 25° C., or about 26° C.; "THF" stands for tetrahydrofuran; "BINAP" stands for 2,2'-bis(diphenylphosphino)-1,1'-binaphthyl; "dppf" stands for 1,1'-bis(diphenylphosphino)ferrocene; "dppb" stands for 1,4-bis(diphenylphosphinobutane; "dppp" stands for 1,3-bis(diphenylphosphino)propane; "dppe" stands for 1,2-bis(diphenylphosphino)ethane. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl", "heterocycloalkyl", or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" or "halo" designates —F, —Cl, —Br or —I; the term "sulfhydryl" means —SH; the term "hydroxyl" means —OH; the term "sulfonyl" means —$SO_2$—; and the term "cyano" as used herein, means a —CN group.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The terms "amine" and "amino" are art recognized and refer to both unsubstituted and substituted amines, e.g., a moiety that can be represented by the general formula:

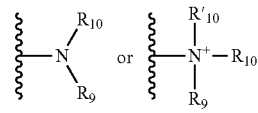

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The definition of each expression, e.g., alkyl, m, n, and the like, when it occurs more than once in any structure, is intended to be independent of its definition elsewhere in the same structure.

The terms triflyl (-Tf), tosyl (-Ts), mesyl (-Ms), and nonaflyl are art-recognized and refer to trifluoromethanesulfonyl, p-toluenesulfonyl, methanesulfonyl, and nonafluorobutanesulfonyl groups, respectively. The terms triflate (—OTf), tosylate (—OTs), mesylate (—OMs), and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein means temporary modifications of a potentially reactive functional group which protect it from undesired chemical transformations. Examples of such protecting groups include silyl ethers of alcohols, and acetals and ketals of aldehydes and ketones, respectively. In embodiments of the disclosure, a carboxylate protecting group masks a carboxylic acid as an ester. In certain other embodiments, an amide is protected by an amide protecting group, masking the —NH$_2$ of the amide as, for example, —NH(alkyl), or —N(alkyl)$_2$. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

As used herein, the term "rotatable bonds" as used herein is a count of single bonds, not in a ring, bound to a nonterminal heavy atom. Excluded from the count are C—N amide bonds because of their high rotational energy barrier. Rotatable bonds are abbreviated as "RB" herein.

Exemplary Compounds

The compounds disclosed herein exclude Debio 1452 and afabicin (Debio 1450):

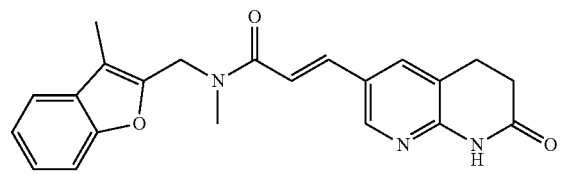

Debio 1452

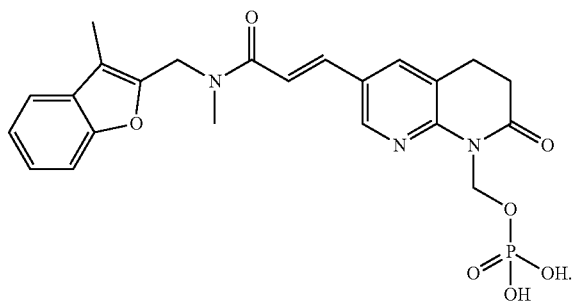

Afabicin (Debio 1450)

In one aspect, the compound is a compound of Formula I or Formula II:

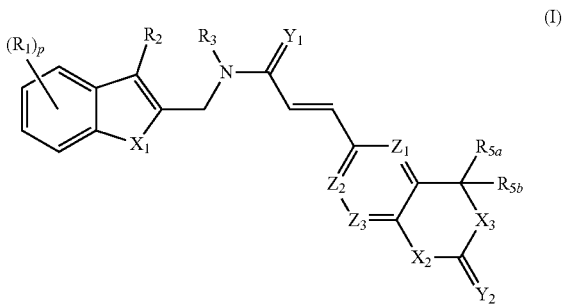

(I)

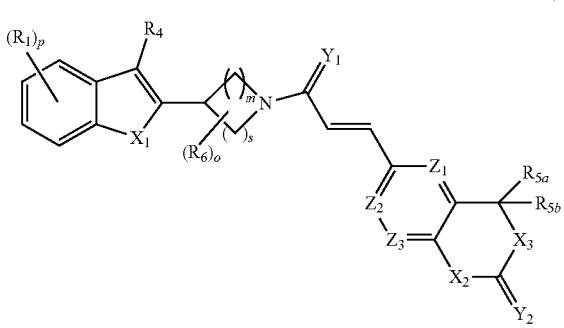

(II)

or a pharmaceutically acceptable salt thereof;
wherein
$X_1$ is selected from the group consisting of O, S, and N($R_7$);
$X_2$ and $X_3$ are each independently selected from the group consisting of C($R_{8a}$)($R_{8b}$), O, S, and N($R_9$);
$Y_1$ and $Y_2$ are each independently selected from the group consisting of O, S, and N($R_{10}$);
$Z_1$, $Z_2$, and $Z_3$ are each independently selected from the group consisting of N and C($R_{11}$);
each $R^1$ is independently selected from the group consisting of halogen, hydroxyl, —O(C$_1$-C$_6$)alkyl, nitro, cyano, N($R_{12a}$)($R_{12b}$), —((C$_1$-C$_6$)alkylene)N($R_{12a}$)($R_{12b}$), cycloalkyl, heterocyclyl, aryl, heteroaryl, aralkyl, and heteroaralkyl;
$R_2$ is selected from the group consisting of halogen, hydroxyl, —O(C$_1$-C$_6$)alkyl, nitro, cyano, N($R_{12a}$)($R_{12b}$), —((C$_1$-C$_6$)alkylene)N($R_{12a}$)($R_{12b}$), —(C$_1$-C$_6$)alkyl, —C(O)(C$_1$-C$_6$)alkyl, cycloalkyl, heterocyclyl, aryl, heteroaryl, aralkyl, and heteroaralkyl;
$R_3$ is selected from the group consisting of —(C$_1$-C$_6$)alkyl, and —C(O)(C$_1$-C$_6$)alkyl; or together $R_2$ and $R_3$ form —(C($R_{13a}$)($R_{13b}$)$_q$—;
$R_4$ selected from the group consisting of halogen, hydroxyl, —O(C$_1$-C$_6$)alkyl, nitro, cyano, —(C$_1$-C$_6$)alkyl, C(O)(C$_1$-C$_6$)alkyl, cycloalkyl, heterocyclyl, aryl, heteroaryl, aralkyl, and heteroaralkyl;
$R_{5a}$ and $R_{5b}$ are each independently selected from the group consisting of hydrogen, —(C$_1$-C$_6$)alkyl, N($R_{12a}$)($R_{12b}$), and —((C$_1$-C$_6$)alkylene)N($R_{12a}$)($R_{12b}$); or together $R_{5a}$ and $R_{5b}$ form an oxo;
each $R_6$ is independently selected from the group consisting of halogen, hydroxyl, —O(C$_1$-C$_6$)alkyl, and —(C$_1$-C$_6$)alkyl;
$R_7$ is selected from the group consisting of hydrogen, —(C$_1$-C$_6$)alkyl, —C(O)(C$_1$-C$_6$)alkyl, and aralkyl;

$R_{8a}$ and $R_{8b}$ are each independently selected from the group consisting of hydrogen, —($C_1$-$C_6$)alkyl, —O($C_1$-$C_6$)alkyl, N($R_{12a}$)($R_{12b}$), and —(($C_1$-$C_6$)alkylene)N($R_{12a}$)($R_{12b}$);

$R_9$ is selected from the group consisting of hydrogen, —($C_1$-$C_6$)alkyl, —(($C_1$-$C_6$)alkylene)OP(O)(O$R_{14}$)$_2$, —C(O)($C_1$-$C_6$)alkyl, C(O)O($C_1$-$C_6$)alkyl, and —(($C_1$-$C_6$)alkylene)N($R_{12a}$)($R_{12b}$);

$R_{10}$ is selected from the group consisting of hydrogen, aryl, aralkyl, and —($C_1$-$C_6$)alkyl;

$R_{11}$ is selected from the group consisting of hydrogen, halogen, hydroxyl, —O($C_1$-$C_6$)alkyl, nitro, cyano, N($R_{12a}$)($R_{12b}$), —(($C_1$-$C_6$)alkylene)N($R_{12a}$)($R_{12b}$), cycloalkyl, heterocyclyl, aryl, heteroaryl, aralkyl, and heteroaralkyl;

$R_{13a}$ and $R_{13b}$ are each independently selected from the group consisting of hydrogen, —($C_1$-$C_6$)alkyl, —C(O)($C_1$-$C_6$)alkyl, and C(O)O($C_1$-$C_6$)alkyl;

each $R_{13a}$ and $R_{13b}$ is independently selected from hydrogen, halogen, hydroxyl, —O($C_1$-$C_6$)alkyl, and —($C_1$-$C_6$)alkyl;

each $R_{14}$ is independently selected from hydrogen and —($C_1$-$C_6$)alkyl;

p is an integer from 0-5;
q is an integer from 1-4 (or 2 or 3 in other embodiments);
m and s are each independently an integer from 0-3; and
o is an integer from 0-5;
provided that:
a) at least one of $R_1$, $R_2$, $R_{5a}$, and $R_{5b}$ is N($R_{12a}$)($R_{12b}$) or —(($C_1$-$C_6$)alkylene)N($R_{12a}$)($R_{12b}$); or
b) together $R_2$ and $R_3$ form —(C($R_{13a}$)($R_{13b}$))$_q$—; or
c) at least one of $Z_1$, $Z_2$, and $Z_3$ is C($R_{11}$), wherein $R_{11}$ is —(($C_1$-$C_6$)alkylene)N($R_{12a}$)($R_{12b}$); or
d) at least one of $X_2$ and $X_3$ is C($R_{8a}$)($R_{8b}$), wherein at least one of $R_{8a}$ and $R_{8b}$ is N($R_{12a}$)($R_{12b}$), or —(($C_1$-$C_6$)alkylene)N($R_{12a}$)($R_{12b}$).

In certain embodiments, the compound is not one of:

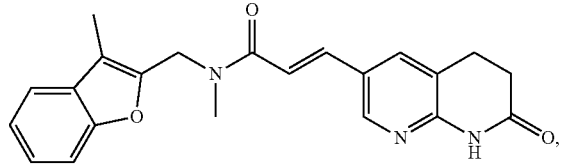

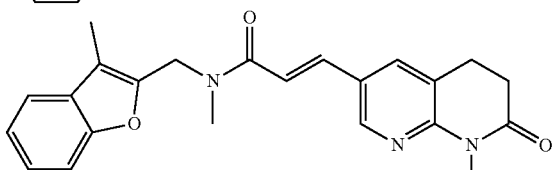

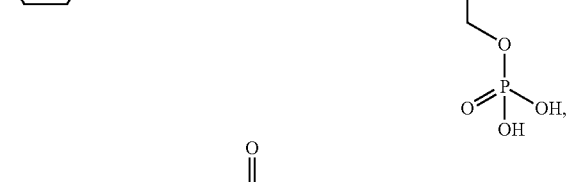

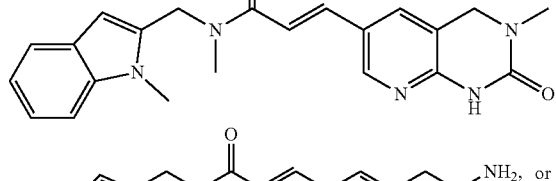

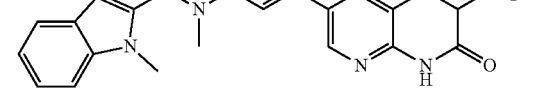

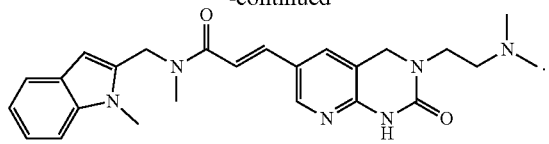

In certain embodiments, the compound of Formula I is represented by Formula Ia:

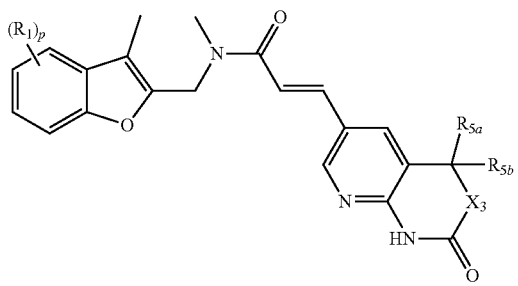

(Ia)

or a pharmaceutically acceptable salt thereof.

In certain embodiments, the compound of Formula I is represented by Formula Ib:

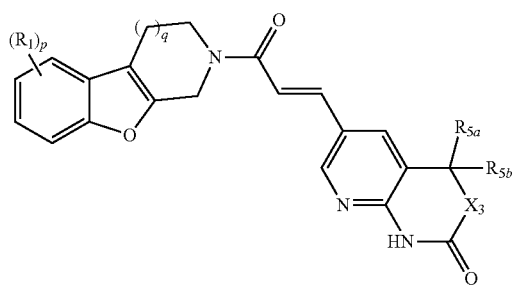

(Ib)

or a pharmaceutically acceptable salt thereof.

In certain embodiments, q of Formula Ib is 2 or 3.

In certain embodiments, the compound of Formula II is represented by Formula IIa:

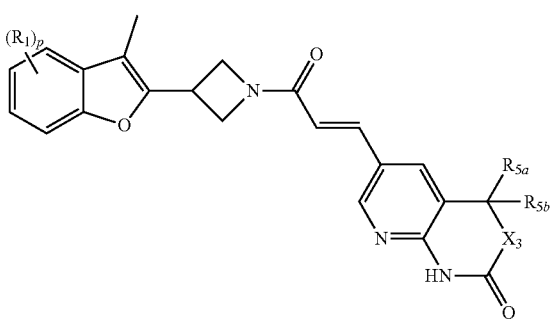

(IIa)

or a pharmaceutically acceptable salt thereof.

In certain embodiments, $R_1$ is —(($C_1$-$C_6$)alkylene)N($R_{12a}$)($R_{12b}$).

In certain embodiments, at least one of $R_{5a}$ and $R_{5b}$ is hydrogen. In certain embodiments, at least one of $R_{5a}$ and $R_{5b}$ is $N(R_{12a})(R_{12b})$ or $—((C_1-C_6)alkylene)N(R_{12a})(R_{12b})$. In other embodiments, both $R_{5a}$ and $R_{5b}$ are hydrogen. In yet other embodiments, together $R_{5a}$ and $R_{5b}$ form an oxo.

In certain embodiments, $X_3$ is $C(R_{8a})(R_{8b})$. In certain embodiments, at least one of $R_{8a}$ and $R_{8b}$ is hydrogen. In certain embodiments, at least one of $R_{8a}$ and $R_{8b}$ is $N(R_{12a})(R_{12b})$ or $—((C_1-C_6)alkylene)N(R_{12a})(R_{12b})$. In other embodiments, both $R_{8a}$ and $R_{8b}$ are hydrogen.

In certain embodiments, at least one of $R_{12a}$ and $R_{12b}$ is hydrogen. In certain embodiments, at least one of $R_{12a}$ and $R_{12b}$ is $C_1-C_6$alkyl, $C(O)(C_1-C_6)$alkyl or $C(O)O(C_1-C_6)$alkyl. In certain embodiments, at least one of $R_{12a}$ and $R_{12b}$ is hydrogen. In other embodiments, both $R_{12a}$ and $R_{12b}$ are hydrogen. In certain embodiments, $R_{12a}$ and $R_{12b}$ are $C_1-C_6$alkyl. In yet other embodiments, both $R_{12a}$ and $R_{12b}$ are $C_1-C_6$alkyl.

In certain embodiments, p is 1.

In certain embodiments, the compound of Formula I or Formula II is selected from the group consisting of:

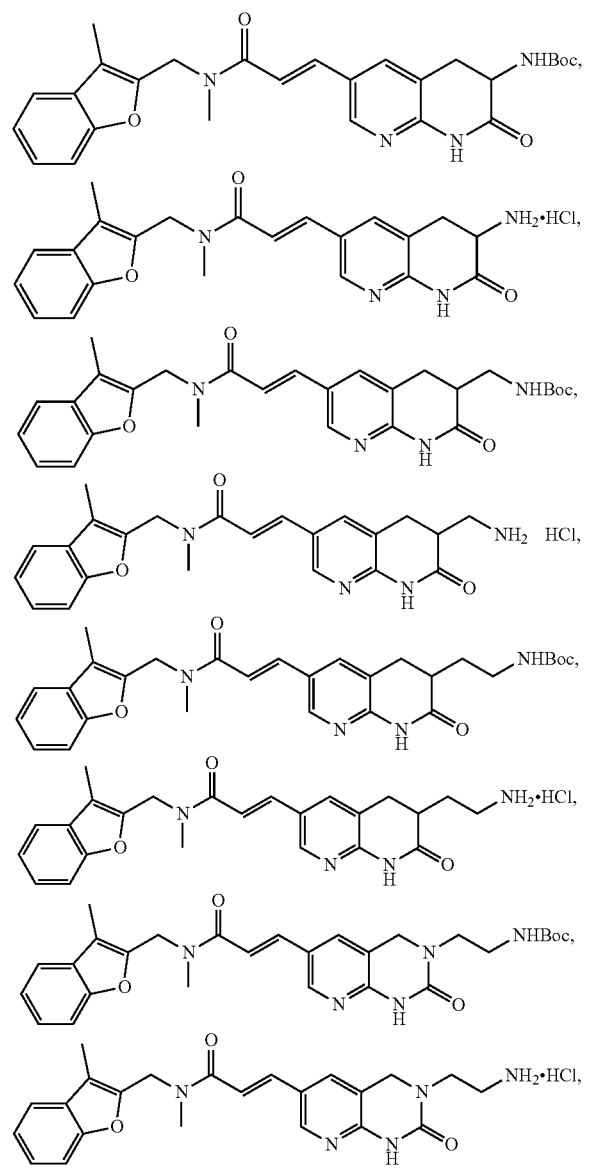

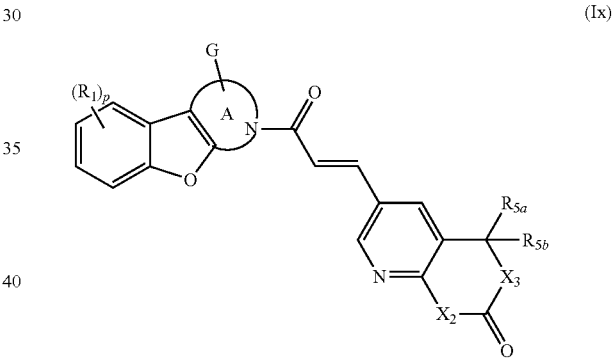

This disclosure also provides an antibacterial compound that is a compound of Formula Ix:

(Ix)

or a pharmaceutically acceptable salt thereof;
wherein
Ring A is a heterocycle comprising 4-6 carbon atoms including the two carbons of the furanyl ring;
G is selected from the group consisting of hydrogen, —(C$_1$-C$_6$)alkyl, N(R$_{12a}$)(R$_{12b}$), and —((C$_1$-C$_6$)alkylene)N(R$_{12a}$)(R$_{12b}$), wherein G is a substituent at one of the 4-6 carbon atoms not including the two carbons of the furanyl ring;
$X_2$ and $X_3$ are each independently selected from the group consisting of C(R$_{8a}$)(R$_{8b}$), O, S, and N(R$_9$);
each R$^1$ is independently selected from the group consisting of halogen, hydroxyl, —O(C$_1$-C$_6$)alkyl, nitro, cyano, N(R$_{12a}$)(R$_{12b}$), —((C$_1$-C$_6$)alkylene)N(R$_{12a}$)(R$_{12b}$), cycloalkyl, heterocyclyl, aryl, heteroaryl, aralkyl, and heteroaralkyl;
R$_{5a}$ and R$_{5b}$ are each independently selected from the group consisting of hydrogen, —(C$_1$-C$_6$)alkyl, N(R$_{12a}$)(R$_{12b}$), and —((C$_1$-C$_6$)alkylene)N(R$_{12a}$)(R$_{12b}$); or together R$_{5a}$ and R$_{5b}$ form an oxo;
R$_{5a}$ and R$_{5b}$ are each independently selected from the group consisting of hydrogen, —(C$_1$-C$_6$)alkyl, —O(C$_1$-C$_6$)alkyl, N(R$_{12a}$)(R$_{12b}$), and —((C$_1$-C$_6$)alkylene)N(R$_{12a}$)

($R_{12b}$); $R_9$ is selected from the group consisting of hydrogen, —($C_1$-$C_6$)alkyl, —(($C_1$-$C_6$)alkylene)OP(O)(OR$_{14}$)$_2$, —C(O)($C_1$-$C_6$)alkyl, C(O)O($C_1$-$C_6$)alkyl, and —(($C_1$-$C_6$)alkylene)N($R_{12a}$)($R_{12b}$);

$R_{12a}$ and $R_{12b}$ are each independently selected from the group consisting of hydrogen, —($C_1$-$C_6$)alkyl, —C(O)($C_1$-$C_6$)alkyl, and C(O)O($C_1$-$C_6$)alkyl;

each $R_{14}$ is independently selected from hydrogen and —($C_1$-$C_6$)alkyl; and p is an integer from 0-5.

In certain embodiments, Ring A is a 5-, 6- or 7-membered heterocyclic ring wherein Ring A includes the nitrogen atom of the amide moiety in the heterocycle of Formula Ix. In other embodiments, the nitrogen atom of said amide moiety of Formula Ix is bonded to the carbon atom positioned alpha or beta to the furanyl oxygen atom. In certain other embodiments, the nitrogen atom of said amide moiety of Formula Ix is 1-, 2-, 3-, 4-, 5-, or 6-carbon atoms from the furanyl oxygen atom.

In certain embodiments, the compound of Formula Ix is selected from the group consisting of:

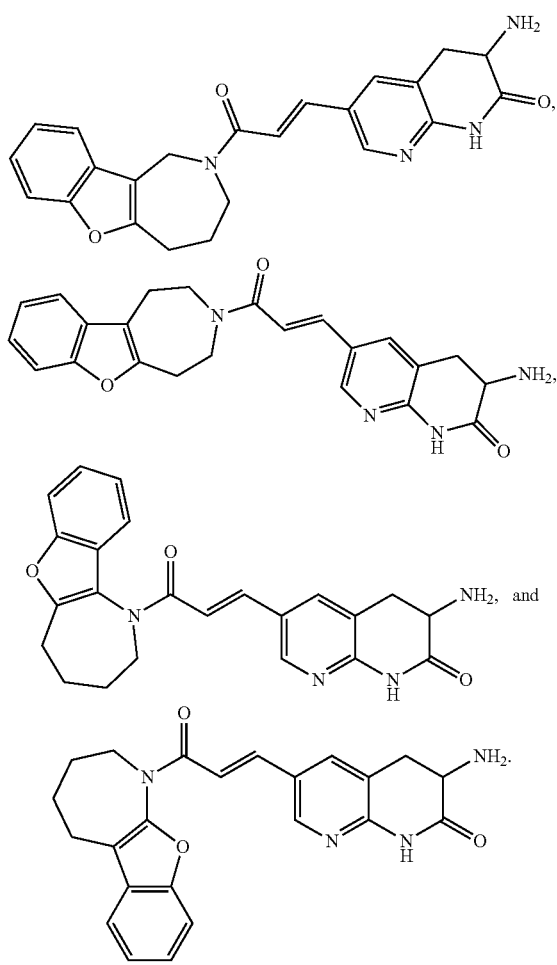

This disclosure also provides a pharmaceutical composition comprising a compound disclosed herein and a pharmaceutically acceptable excipient. In other embodiments, the pharmaceutical composition is formulated for intraperitoneal, intravenous or oral administration.

The compounds disclosed herein exclude Ribocil C:

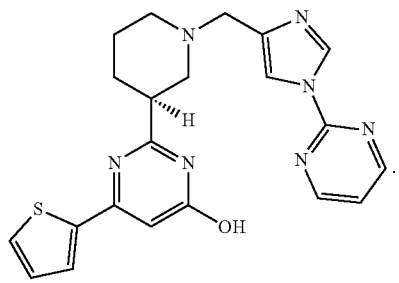

Ribocil C

In certain aspects, the compounds are represented by Formula III:

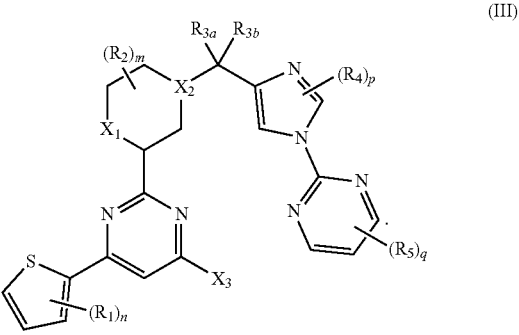

(III)

or a pharmaceutically acceptable salt thereof;
wherein
$X_1$ is selected from the group consisting of NR$_6$ and C(R$_{7a}$)(R$_{7b}$);
$X_2$ is selected from the group consisting of N and CR$_8$;
$X_3$ is selected from the group consisting of OR$_9$, SR$_9$ and N(R$_{10a}$)(R$_{10b}$);
each $R_1$, $R_2$, $R_4$, and $R_5$ is independently selected from the group consisting of halogen, hydroxyl, —O($C_1$-$C_6$)alkyl, nitro, cyano, —($C_1$-$C_6$)alkyl, N(R$_{11a}$)(R$_{11b}$), —(($C_1$-$C_6$)alkylene)N(R$_{11a}$)(R$_{11b}$), cycloalkyl, heterocyclyl, aryl, heteroaryl, aralkyl, and heteroaralkyl;
$R_{3a}$ and $R_{3b}$ are each independently selected from the group consisting of hydrogen, —($C_1$-$C_6$)alkyl, N(R$_{11a}$)(R$_{11b}$), and (($C_1$-$C_6$)alkylene)N(R$_{11a}$)(R$_{11b}$); or $R_{3a}$ and $R_{3b}$ together form an oxo;
$R_6$ is selected from the group consisting of hydrogen, aryl, heteroaryl, cycloalkyl, heterocyclyl, aralkyl, —($C_1$-$C_6$) alkyl, and (($C_1$-$C_6$)alkylene)N(R$_{11a}$)(R$_{11b}$);
$R_{7a}$ and $R_{7b}$ are each independently selected from the group consisting of hydrogen, —($C_1$-$C_6$)alkyl, N(R$_{11a}$)(R$_{11b}$), and (($C_1$-$C_6$)alkylene)N(R$_{11a}$)(R$_{11b}$); or together $R_{7a}$ and $R_{7b}$ form an oxo;
$R_8$ is selected from the group consisting of hydrogen, N(R$_{11a}$)(R$_{11b}$), —(($C_1$-$C_6$)alkylene)N(R$_{11a}$)(R$_{11b}$), and —($C_1$-$C_6$)alkyl; $R_9$ is selected from the group consisting of hydrogen, aryl, heteroaryl, cycloalkyl, heterocyclyl, aralkyl, and —($C_1$-$C_6$)alkyl;
$R_{10a}$ and $R_{10b}$ are each independently selected from the group consisting of hydrogen, aryl, heteroaryl, cycloalkyl, heterocyclyl, aralkyl, —($C_1$-$C_6$)alkyl, C(O)($C_1$-$C_6$)alkyl, and C(O)O($C_1$-$C_6$)alkyl;

$R_{11a}$ and $R_{11b}$ are each independently selected from the group consisting of hydrogen, aryl, heteroaryl, cycloalkyl, heterocyclyl, aralkyl, —($C_1$-$C_6$)alkyl, C(O)($C_1$-$C_6$)alkyl, and C(O)O($C_1$-$C_6$)alkyl;

n and q are each independently an integer from 0-3;

m is an integer from 0-7; and p is an integer from 0-2;

provided that:

a) at least one of $R_1$, $R_2$, $R_{3a}$, $R_{3b}$, $R_4$, and $R_5$ is $N(R_{11a})(R_{11b})$ or $((C_1$-$C_6)$alkylene$)N(R_{11a})(R_{11b})$, and at least one of n, q, m and p is 1;

b) $X_1$ is $NR_6$ or $C(R_{7a})(R_{7b})$, and at least one of $R_{7a}$ and $R_{7b}$ is $N(R_{11a})(R_{11b})$; or c) $X_2$ is $CR_8$ and $R_8$ is $N(R_{11a})(R_{11b})$ or $((C_1$-$C_6)$alkylene$)N(R_{11a})(R_{11b})$.

In certain specific embodiments, the compound of Formula III is not:

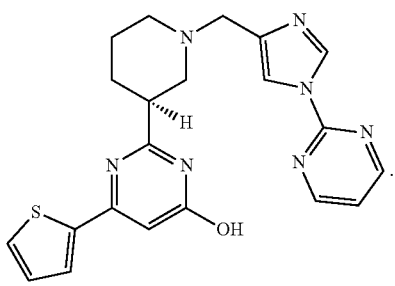 [SMILES: Oc1cc(-c2cccs2)nc([C@H]2CCCN(Cc3cn(-c4ncccn4)cn3)C2)n1]

In certain embodiments, the compound of Formula III is represented by Formula IIIa:

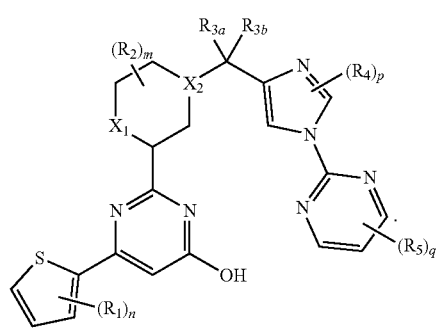

(IIIa)

or a pharmaceutically acceptable salt thereof.

In certain embodiments, $R_1$ is $((C_1$-$C_6)$alkylene$)N(R_{11a})(R_{11b})$.

In certain embodiments, $X_1$ is $NR_6$. In certain embodiments, $R_6$ is hydrogen, —($C_1$-$C_6$)alkyl, or —(($C_1$-$C_6$)alkylene$)N(R_{11a})(R_{11b})$.

In other embodiments, $X_1$ is $C(R_{7a})(R_{7b})$. In other embodiments, $R_{7a}$ and $R_{7b}$ is —$N(R_{11a})(R_{11b})$. In certain embodiments, at least one of $R_{7a}$ and $R_{7b}$ is hydrogen. In certain embodiments, both $R_{7a}$ and $R_{7b}$ are hydrogen.

In certain embodiments, $X_2$ is $CR_8$. In certain embodiments, $R_8$ is —$N(R_{11a})(R_{11b})$ or —(($C_1$-$C_6$)alkylene$)N(R_{11a})(R_{11b})$. In certain embodiments, at least one of $R_{3a}$ and $R_{3b}$ is $((C_1$-$C_6)$alkylene$)N(R_{11a})(R_{11b})$. In other embodiments, at least one of $R_{3a}$ and $R_{3b}$ is hydrogen. In other embodiments, both $R_{3a}$ and $R_{3b}$ are hydrogen.

In certain embodiments, $R_4$ is $((C_1$-$C_6)$alkylene$)N(R_{11a})(R_{11b})$.

In certain embodiments, $R_2$ is $N(R_{11a})(R_{11b})$ or $((C_1$-$C_6)$alkylene$)N(R_{11a})(R_{11b})$. In certain embodiments, $R_5$ is $((C_1$-$C_6)$alkylene$)N(R_{11a})(R_{11b})$.

In certain embodiments, at least one of $R_{11a}$ and $R_{11b}$ is hydrogen. In certain embodiments, at least one of $R_{11a}$ and $R_{11b}$ is —($C_1$-$C_6$)alkyl, C(O)($C_1$-$C_6$)alkyl, or C(O)O($C_1$-$C_6$)alkyl. In other embodiments, both $R_{11a}$ and $R_{11b}$ are hydrogen. In yet other embodiments, both $R_{11a}$ and $R_{11b}$ are —($C_1$-$C_6$)alkyl.

In certain embodiments, at least one of n, q, m, and p is 1.

In certain embodiments, the compound of Formula III is selected from the group consisting of:

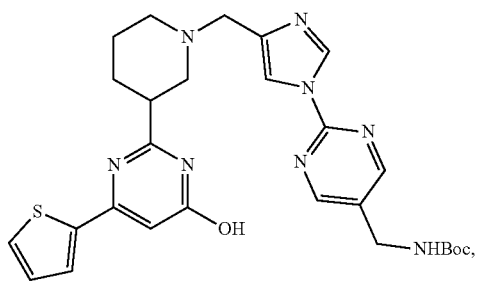

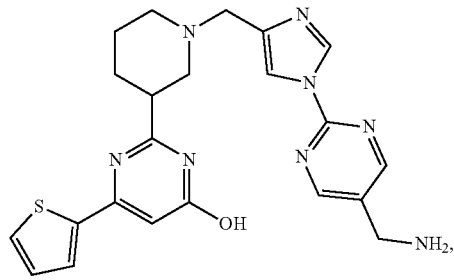

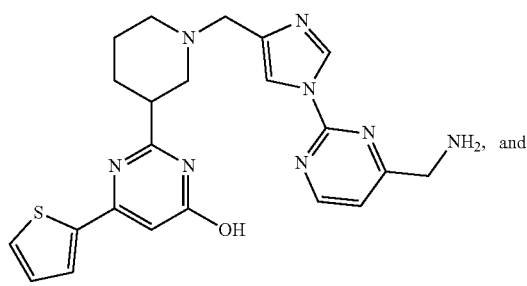

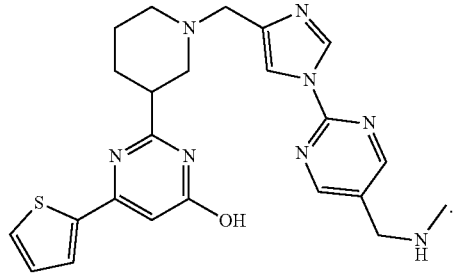

The compounds disclosed herein exclude Zantrin Z3:

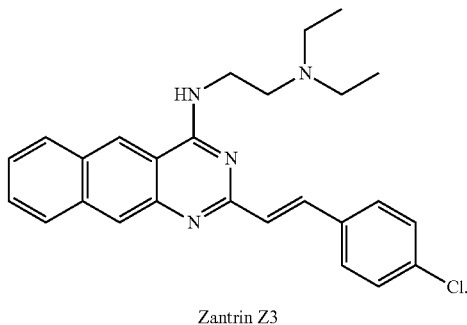 [SMILES: CCN(CC)CCNc1nc(/C=C/c2ccc(Cl)cc2)nc2cc3ccccc3cc12]

Zantrin Z3

In certain aspects, the compounds are represented by Formula IV or Formula V:

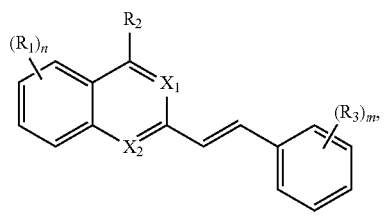

(IV)

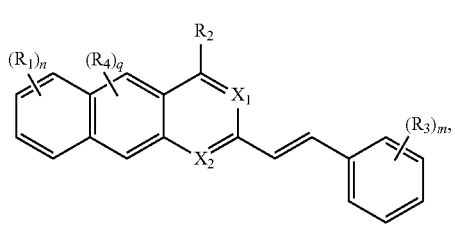

(V)

or a pharmaceutically acceptable salt thereof;
wherein
$X_1$ and $X_2$ are selected from the group consisting of CH, $CR_5$ and N;
each $R_1$, $R_2$, $R_3$, $R_4$, and $R_5$ is independently selected from the group consisting of halogen, hydroxyl, —O($C_1$-$C_6$)alkyl, nitro, cyano, —($C_1$-$C_6$)alkyl, N($R_{6a}$)($R_{6b}$), —(($C_1$-$C_6$)alkylene)N($R_{6a}$)($R_{6b}$), C(O)($C_1$-$C_6$)alkyl, C(O)O($C_1$-$C_6$)alkyl, C(O)N($C_1$-$C_6$)alkyl, S(O)$_t$$R_7$, cycloalkyl, heterocyclyl, aryl, heteroaryl, aralkyl, and heteroaralkyl;
$R_{6a}$ and $R_{6b}$ are each independently selected from the group consisting of hydrogen, aryl, heteroaryl, cycloalkyl, heterocyclyl, aralkyl, —($C_1$-$C_6$)alkyl, —(($C_1$-$C_6$)alkylene)N($R_{8a}$)($R_{8b}$), C(O)($C_1$-$C_6$)alkyl, and C(O)O($C_1$-$C_6$)alkyl;
$R_7$ is selected from the group consisting of hydrogen, aryl, heteroaryl, cycloalkyl, heterocyclyl, aralkyl, and —($C_1$-$C_6$)alkyl;
$R_{8a}$ and $R_{8b}$ are each independently selected from the group consisting of hydrogen, aryl, heteroaryl, cycloalkyl, heterocyclyl, aralkyl, —($C_1$-$C_6$)alkyl, C(O)($C_1$-$C_6$)alkyl, and C(O)O($C_1$-$C_6$)alkyl;

n is an integer from 0-4; m is an integer from 0-5; and t and q are each independently an integer from 0-2;
provided that:
the compound is not

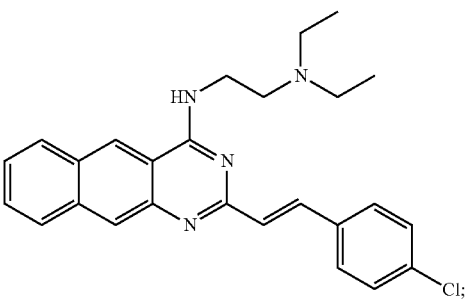 [SMILES: CCN(CC)CCNc1nc(/C=C/c2ccc(Cl)cc2)nc2cc3ccccc3cc12]

and
a) at least one of $R_1$, $R_2$, $R_3$, and $R_4$, is N($R_{6a}$)($R_{6b}$) or —(($C_1$-$C_6$)alkylene)N($R_{6a}$)($R_{6b}$); and at least one of n, m, and q is 1; or
b) $X_1$ or $X_2$ is $CR_5$, wherein $R_5$ is N($R_{6a}$)($R_{6b}$) or (($C_1$-$C_6$)alkylene)N($R_{6a}$)($R_{6b}$).

In certain embodiments, the compound of Formula IV or Formula V is represented by Formula IVa or Formula Va:

(IVa)

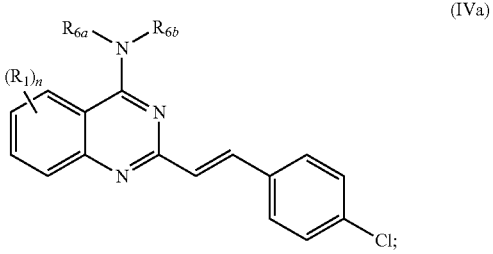

(Va)

or a pharmaceutically acceptable salt thereof.
In certain embodiments, $R_1$ is —($C_1$-$C_6$)alkyl.
In certain embodiments, at least one of $R_{6a}$ and $R_{6b}$ is hydrogen. In certain embodiments, at least one of $R_{6a}$ and $R_{6b}$ is —(($C_1$-$C_6$)alkylene)N($R_{8a}$)($R_{8b}$).
In certain embodiments, at least one of $R_{8a}$ and $R_{8b}$ is hydrogen. In certain embodiments, at least one of $R_{8a}$ and $R_{8b}$ is —($C_1$-$C_6$)alkyl or —C(O)($C_1$-$C_6$)alkyl. In other embodiments, both $R_{8a}$ and $R_{8b}$ are hydrogen or —($C_1$-$C_6$)alkyl.

In certain embodiments, the compound of Formula IV or Formula V is selected from the group consisting of:
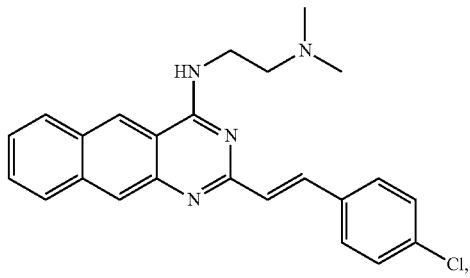
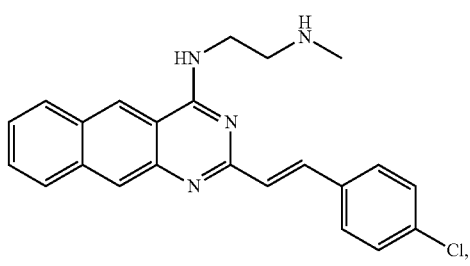
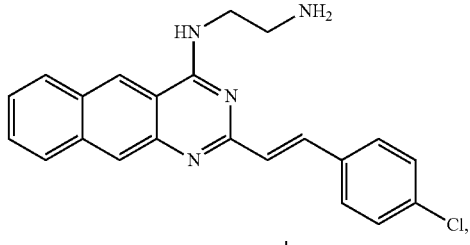
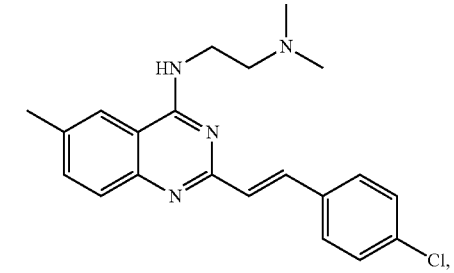
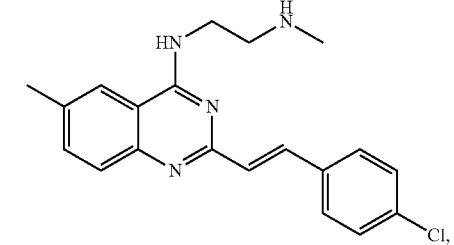
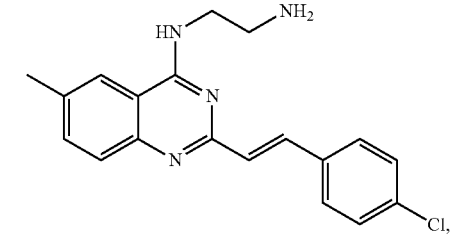
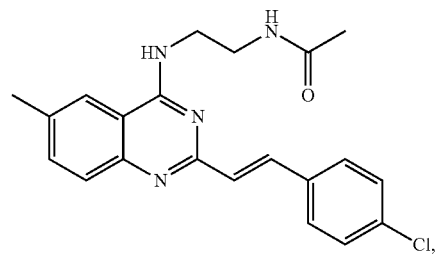
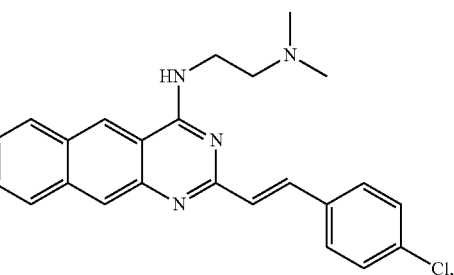
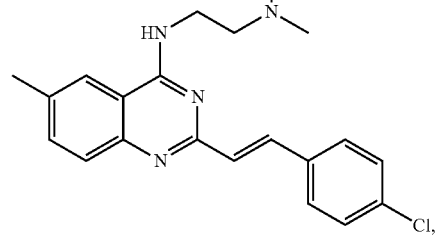
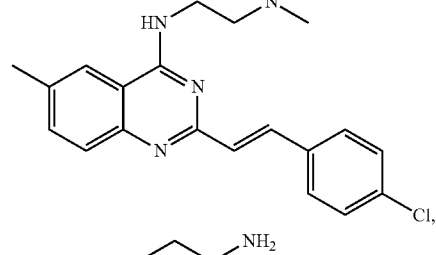
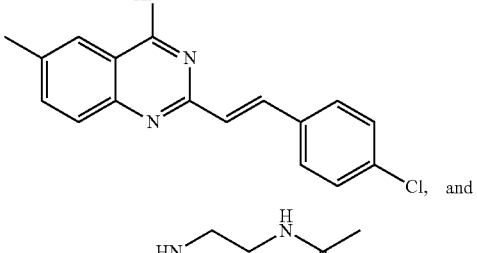, and
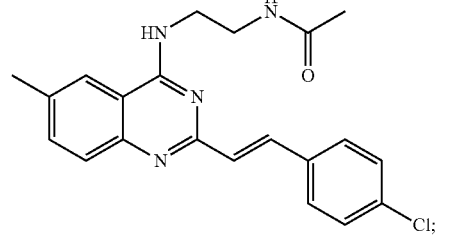;
or a pharmaceutically acceptable salt thereof.

Exemplary Methods

In certain embodiments, the compounds disclosed herein accumulate in Gram-negative bacteria.

In certain embodiments, the compounds disclosed herein traverse a porin.

In certain embodiments, provided herein is a method of antimicrobial treatment, comprising, administering to a subject in need thereof a therapeutically effective amount of a compound disclosed herein, or a pharmaceutically acceptable salt thereof, thereby killing or inhibiting the growth of at least a portion of a plurality of microorganisms in the subject.

In certain embodiments, the compound is a compound of any one of Formulas I, II, III, IV, or V.

In certain embodiments, provided herein is a method of antimicrobial treatment, comprising providing a sample comprising a plurality of microorganisms; and contacting the sample with a compound disclosed herein; thereby killing or inhibiting the growth of at least a portion of the plurality of microorganisms in the sample.

In certain embodiments of the methods of antimicrobial treatment disclosed herein, at least a portion of the plurality of microorganisms is killed.

In certain embodiments of the methods of antimicrobial treatment disclosed herein, the growth of at least a portion of the plurality of microorganisms is inhibited.

In certain embodiments, the microorganism is a bacterium, a virus, a fungus, or a parasite. In certain embodiments, the microorganism is drug resistant, such as antibiotic resistant. In certain embodiments, the microorganism is multi-drug resistant.

In certain embodiments, the microorganism is a bacterium. In certain embodiments, the microorganism is a Gram-negative bacterium. In certain embodiments, the microorganism is a Gram-positive bacterium. In certain embodiments, for example, the microorganism is at least one bacterium selected from the group consisting of *Acinetobacter*, anthrax-causing bacteria, Bacilli, *Bordetella*, *Borrelia*, botulism, *Brucella, Burkholderia, Campylobacter, Chlamydia*, cholera-causing bacteria, *Clostridium, Gonococcus, Corynebacterium*, diptheria-causing bacteria, *Enterobacter, Enterococcus, Erwinia, Escherichia, Francisella, Haemophilus, Heliobacter, Klebsiella, Legionella, Leptospira*, leptospirosis-causing bacteria, *Listeria*, Lyme's disease-causing bacteria, *meningococcus, Mycobacterium, Mycoplasma, Neisseria, Pasteurella, Pelobacter*, plague-causing bacteria., *Pneumonococcus, Proteus, Pseudomonas, Rickettsia, Salmonella, Serratia, Shigella, Staphylococus, Streptococcus*, tetanus-causing bacteria, *Treponema, Yersinia* and *Xanthomonas*. In certain embodiments, the microorganism is at least one bacterium selected from the group consisting of *Acinetobacter baumannii, Escherichia coli, Enterobacter cloacae, Klebsiella pneumoniae, Pseudomonas aeruginosa*, and *Staphylococcus aureus*. In certain embodiments, the microorganism is methicillin-resistant *Staphylococcus aureus* (MRSA). In certain embodiments, the microorganism is *Pseudomonas aeruginosa*.

In certain embodiments, for example, the microorganism is at least one virus selected from *Adenoviridae, Papillomaviridae, Polyomaviridae, Herpesviridae, Poxviridae, Hepadnaviridae, Parvoviridae, Astroviridae, Caliciviridae, Picornaviridae, Coronaviridae, Flaviviridae, Reiroviridae, Togaviridae, Arenaviridae, Bunyaviridae, Filoviridae, Orthomyxoviridae, Paramyxoviridae, Rhabdoviridae*, and *Reoviridae*. In certain embodiments, the virus may be arboviral encephalitis virus, adenovirus, herpes simplex type I, herpes simplex type 2, Varicella-zoster virus, Epstein-barr virus, cytomegalovirus, herpesvirus type 8, papillomavirus, BK virus, coronavirus, echovirus, JC virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, chola virus, Marburg virus, measles virus, molluscum virus, mumps virus, parainfluenza, respiratory syncytial virus, human metapneumovirus, Hendra virus, Nipah virus, rabies, Hepatitis D, rotavirus, orb virus, coltivirus, vaccinia virus, and Banna virus.

In certain embodiments, for example, the microorganism is at least one fungus selected from *Aspergillus (fumigatus, niger*, etc.), *Basidiobolus (ranarum*, etc.), *Blastomyces dermatitidis, Candida (albicans, krusei, glabrata, tropicalis*, etc.), *Coccidioides immitis, Cryptococcus (neoformans*, etc.), *eumycetoma, Epidermophyton (floccosum*, etc.), *Histoplasma capsulatum, Hortaea werneckii, Lacazia loboi, Microsproum (audouinii, nanum* etc.), *Mucorales (mucor, absidia, rhizophus), Paracoccidioides brasiliensis, Rhinosporidium seeberi, Sporothrix schenkii*, and *Trichophyton (schoeleinii, mentagrophytes, rubrum, verrucosum*, etc.).

In certain embodiments, for example, the microorganism is at least one parasite selected from *Acanthamoeba, Babesia microti, Balantidium coli, Entamoeba hystolytica, Giardia Cryptosporidium muris, Trypanosomatids gambiense, Trypanosomatida rhodesiense, Trypanosoma brucei, Trypanosoma cruzi, Leishmania mexicana, Leishmania brasiliensis, Leishmania tropica, Leishmania donovani, Toxoplasma gondii, Plasmodium vivax, Plasmodium ovale, Plasmodium malariae, Plasmodium falciparum, Pneumocystis carinii, Trichomonas vaginalis, Histomonas meleagridis, Secenientea, Trichuris trichiura, Ascaris lumbricoides, Enterobius Ancylostoma duodenale, Naegleria fowleri, Necator americanus, Nippostrongylus brasiliensis, Strangyloides stercoralis, Wuchereria bancrofti, Dracunculus medinensis*, blood flukes, liver flukes, intestinal flukes, lung flukes, *Schistosoma mansoni, Schistosoma haematobium, Schistosoma japonicum, Fasciola hepatica, Fasciola gigantica, Heterophyes heterophyes*, and *Paragonimus westermani*.

In certain embodiments, the subject is a mammal or reptile. In certain embodiments, the mammal is a primate, feline, canine, rodent, ovine, or bovine. In certain embodiments, the mammal is a human. In other embodiments, the subject is a vertebrate or invertebrate. In other embodiments, the subject is a fish, amphibian, or bird.

Results and Discussion

The increased frequency of multidrug resistant (MDR) bacterial infections coupled with a low number of antibiotic classes has left a diminished arsenal of effective antibacterial agents. During the last half-century seven new antibiotic classes have been introduced into the clinic, none of which are useful against the most problematic Gram-negative "ESKAPE" pathogens, namely *Klebsiella pneumoniae, Acinetobacter baumannii, Pseudomonas aeruginosa*, and *Enterobacter* species. Despite tremendous advances in genomics and high-throughput screening in the last 50 years, novel antibiotic classes active against these high priority Gram-negative pathogens have remained elusive.

While there are over two dozen new small molecule antibiotics in some stage of clinical trials, only one that is effective against Gram-negative ESKAPE pathogens is from a novel drug class, and this compound (murepavadin) is only effective against *P. aeruginosa*. This lack of new drug classes for the problematic Gram-negatives is consistent with the low hit rate reported from extensive antimicrobial high-throughput screening campaigns. This discovery challenge is not ascribed to poor target activity, but rather to challenges of compound accumulation in Gram-negative pathogens, given the impermeability of their cell membranes coupled with promiscuous efflux pumps. In contrast to the discouraging results in screening for Gram-negative actives, there have been an abundance of compounds discovered that have promising activity against Gram-positive bacteria. Present amongst these compounds are both natural products and synthetic compounds, many of which act through mechanisms outside the common targets, that is, they are not ribosome binders, cell wall biosynthesis inhibitors, or DNA gyrase inhibitors. Importantly, the vast majority of these compounds would kill Gram-negative bacteria if they could accumulate inside these pathogens.

Unfortunately, this rich array of diverse and promising agents has not led to an expanded arsenal of antibiotics for Gram-negative pathogens, as no method for the conversion of Gram-positive-only compounds into broad-spectrum antibiotics has been widely applicable. Creative approaches to this problem such as attachment to siderophores, cotreatment with efflux pump inhibitors, and potentiation by nonlytic polymyxins are under active investigation. An alternative approach is tuning the physiochemical properties of antibiotics to favor accumulation inside the bacterial cell. If Gram-negative bacterial accumulation could be optimized by employing routine medicinal chemistry strategies—analogous to the now-common practice of improving solubility or pharmacokinetics—then the attrition of antibiotics in early discovery stage might be mitigated. Such a strategy would necessarily rely on an appropriate knowledgebase detailing the physicochemical parameters allowing compound accumulation in Gram-negative bacteria.

Toward this end, the results from a prospective study examining the ability of diverse compounds to accumulate in *E. coli* was reported (*Nature* 545, 299-304 (2017)). This work revealed that compounds with certain physicochemical properties—the presence of an ionizable nitrogen, low three-dimensionality, and low numbers of rotatable bonds (codified as the "eNTRy rules" (*Ann. N. E Acad. Sci.* 1435, 18-38 (2019)))—have a significantly higher probability of accumulating in *E. coli*. Herein is reported a convenient web-based cheminformatics tool to assist in the design of compounds that accumulate in and are active against Gram-negative bacteria.

The initial methodology for calculating eNTRy rule parameters relied on proprietary algorithms to perform conformer generation and globularity calculation. With the goal of developing a free, easy-to-use web application, the first step was to implement these calculations with open-source libraries. While several conformer generation methods were evaluated, ultimately confab was found to rapidly and accurately generate an ensemble of conformers. Globularity calculation was implemented with linear algebra modules from NumPy (*Guide to NumPy.* (Trelgol Publishing, 2006), pp. 364).

Figure 5:
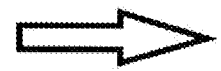
FIG. 5. Overview of entry-way functionality and examples of visual outputs.
Figure 5:
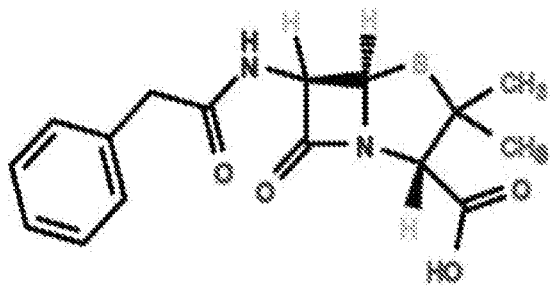
Figure 5:
Figure 5:
Figure 5:
Figure 5:
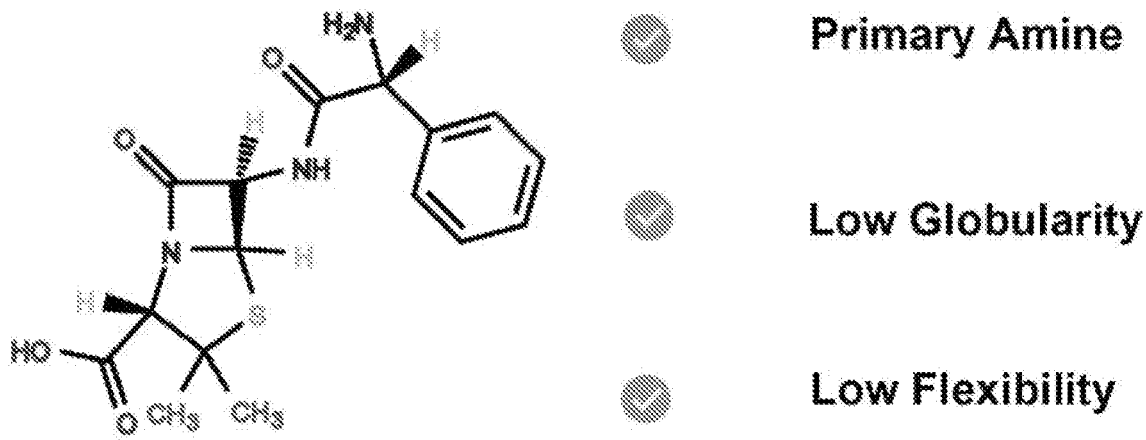
Figure 5:
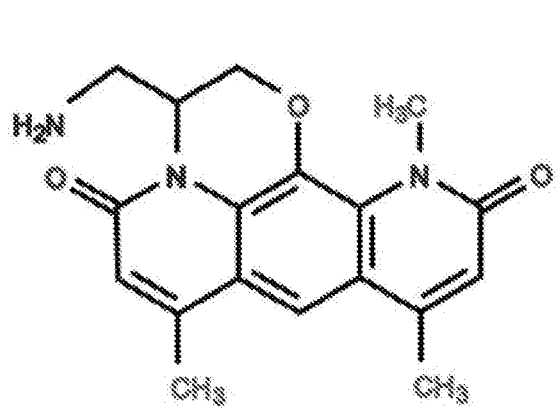
Figure 5:
Figure 5:
Figure 5:
Figure 5:
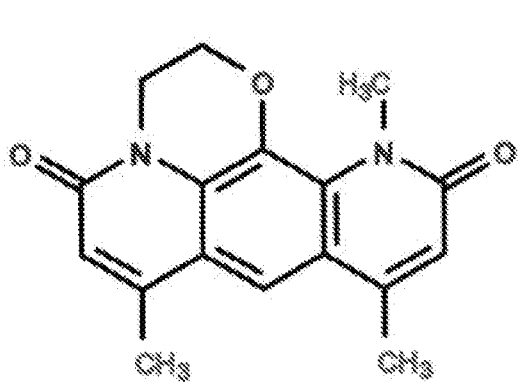
Figure 5:
Figure 5:
Figure 5:

Upon establishing accurate and accessible calculation methods for eNTRy rules, a web application (entry-way.org) was built in which users submit a SMILES string of a molecule of interest. RDkit parses the SMILES string and makes an initial estimate of the 3D coordinates, confab generates a library of conformers, and a custom Python program calculates globularity (FIG. 1A). The rotatable bond counting and functional group detection is performed separately using the 2D structure (FIG. 1A). Results from these calculations are displayed to the user and are compared to breakpoints provided by the eNTRy rules; for specific examples of visual outputs from entry-way.org, see FIG. 5.

Applying eNTRyway to almost 70 Gram-positive only FDA-approved antibiotics, drugs currently in clinical development, and lead compounds in pre-clinical stages indicates that there are numerous candidates for conversion at all stages of development (FIG. 1B). Through this analysis Debio-1452 emerged as an attractive candidate for transformation to a Gram-negative active version. With a low globularity (Glob=0.087) and few rotatable bonds (RB=4), Debio-1452 (FIG. 1C) conforms to two of the three eNTRy rules, lacking only a primary amine.

Debio-1452 (also called AFN-1252) originated in the early 2000s from lead optimization efforts of a hit discovered in a target-based (biochemical) high-throughput screen at GlaxoSmithKline for inhibitors of the enoyl-acyl carrier reductase enzyme FabI. FabI plays a pivotal role in the elongation cycle of the bacterial fatty acid biosynthesis pathway (FAS-II); for Gram-negative pathogens the FAS-II pathway is essential to survival and inhibition of the FAS-II pathway cannot be bypassed during host infections through uptake of exogenous nutrients. Notably, components of the bacterial FAS-II pathway are distinct from those found in the analogous mammalian FAS-I pathway.

This essentiality and orthogonality to the mammalian counterpart makes components of the FAS-II pathway attractive biological targets for antimicrobial drug discovery, and the potential for targeting FAS-II is exemplified by the success of triclosan and isoniazid, both of which inhibit FabI or a closely related enzyme. Although redundant isoforms of FabI are present in certain bacterial species, such as FabV present in *P. aeruginosa*, which can compensate for FabI inhibition, FabI is the sole enoyl-acyl carrier reductase for the other Gram-negative ESKAPE pathogens including *Enterobacter* spp., *A. baumannii*, and *K. pneumonia*.

While Debio-1452 displays significant antibiotic activity against *Staphylococcus aureus* (MIC=0.008 µg/mL), activity against Gram-negative ESKAPE pathogens and *E. coli* is lacking (MIC>32 µg/mL, FIG. 2); however, Debio-1452 is very potent in *E. coli* with compromised efflux or permeability defects (ΔtolC, ΔrfaC, FIG. 2), indicating that whole cell activity against Gram-negative bacteria is limited by low cellular accumulation and not by on-target activity.

Debio-1452 has marked efficacy in animal models of *S. aureus* infections and in patients in an open-label clinical trial. Debio-1452 thus is a constituent of a novel antimicrobial drug class, hits a compelling antibiotic target and possesses structural features making it appropriate for conversion to a Gram-negative active via the eNTRy rules. While over 100 derivatives of Debio-1452 have been prepared, none are reported to have robust activity against the Gram-negative ESKAPE pathogens.

Debio-1452-NH3: As Debio-1452 already possessed favorable physicochemical properties in terms of globularity and flexibility, conversion into an analogue with increased potential for Gram-negative antibacterial activity required the strategic introduction of a primary amine. Examination of the co-crystal structure of Debio-1452 bound to *S. aureus* FabI (FIG. 1C and FIG. 1E) showed the 3-position of the naphthyridinone ring (adjacent to the lactam carbonyl) to be the most solvent-exposed region of the molecule, consistent with antibacterial data suggesting that substituents were tolerated at this position. eNTRyway predicted that key compounds with amines at this location would accumulate in *E. coli*, highlighting the 3-position of the naphthyridinone ring as a promising point of for incorporation of an amine. Additionally, computational docking of these compounds, including Debio-1452-NH3 (FIG. 1D and Table 1), indicating that amine modification would not be disruptive to binding the FabI target.

positive *S. aureus*, and against *E. coli* strains with defective efflux (ΔtolC) or modified outer membranes (ΔrfaC) which render them susceptible to Gram-positive-only antibiotics (FIG. 2). Importantly, Debio-1452-NH3 also possesses antibacterial activity (MIC=4 μg/mL) in *E. coli* strains with intact outer membranes, whereas Debio-1452 has no activity

TABLE 1

Results from molecular docking of Debio-1452 derivatives into FabI.

| | | Docking Score (kcal/mol) | | MM-GBSA ΔΔ $G_{bind}$ (kcal/mol) | |
|---|---|---|---|---|---|
| Name | R | E. coli | S. aureus | E. coli | S. aureus |
| Debio-1452 | n.c. | n.a. | n.a. | 0 | 0 |
| Debio-1452-NH3 | | −15.25 | −15.18 | −4.29 | −5.76 |
| 2 | | −15.19 | −14.84 | −3.11 | −1.50 |
| 3 | | −14.59 | −14.33 | −7.57 | −4.62 | n.c. = no change

*S. aureus* FabI (PDB: 4FS3) was prepared as a receptor using Schrodinger Protein Prep Wizard. Ligands were prepared using LigPrep and docked using Glide XP (rigid receptor, flexible ligand). Amine-containing derivatives were docked as protonated forms. Top ranked poses were refined using MM-GBSA with Prime (VSGB solvation model, OPLS3e force field, flexibility allowed 5 Å around ligands with hierarchical sampling).

Figure 6:
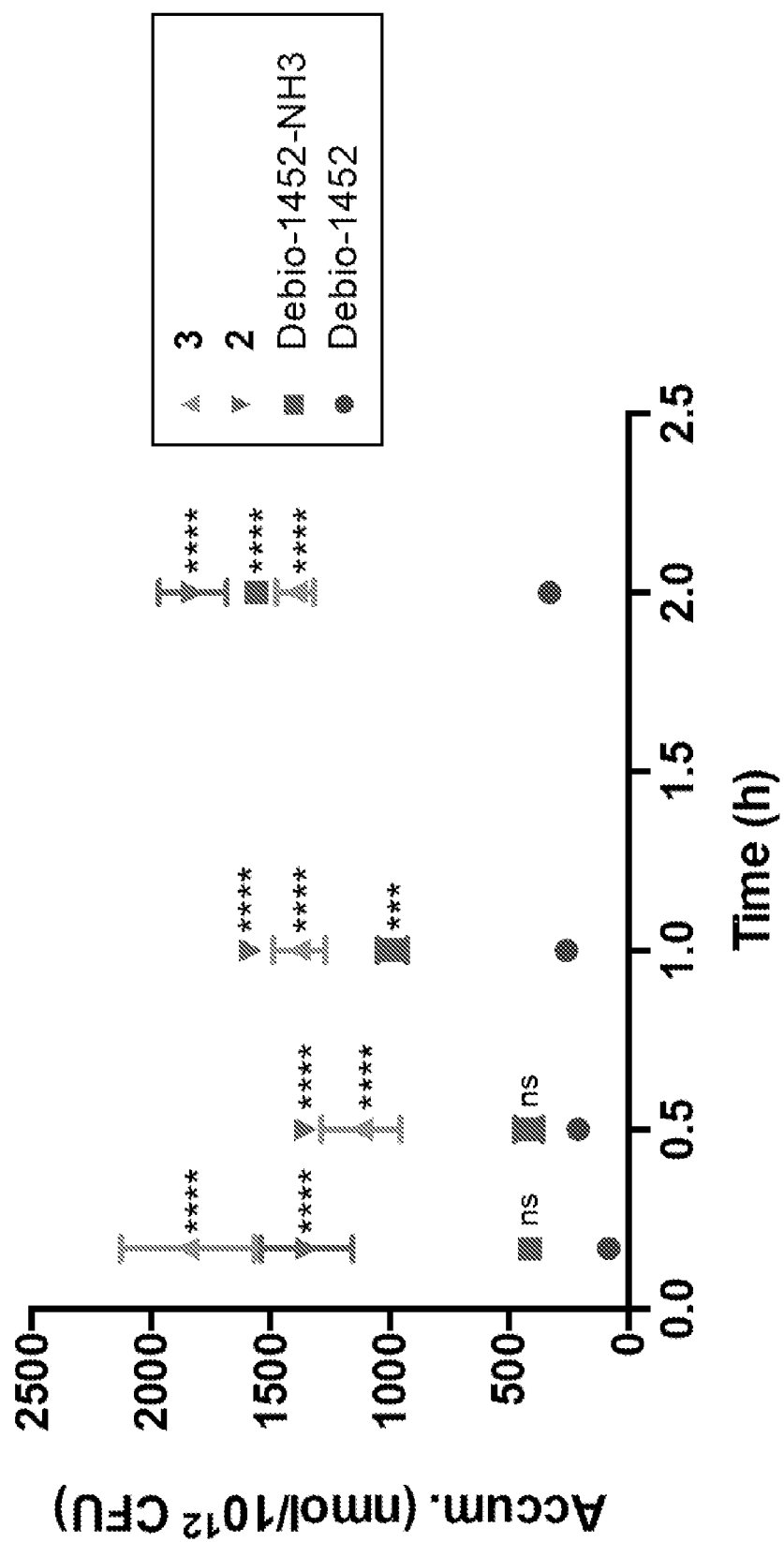
FIG. 6. Accumulation of Debio-1452 and derivatives in *E. coli* MG1655 over time. Bacterial cells were washed with and suspended in PBS. Cells were exposed to compound (50 µM final) and incubated at 37° C. with shaking for 10 min, 30 min, 1 h, and 2 h. All cells were viable at these time points. Extra-cellular compound was removed, cells were lysed, and amount of compound in lysate was quantified by LC-MS/MS. Accumulation reported in nmol per $10^{12}$ colony-forming units (CFUs). Data shown represents the average of three independent experiments. Error bars represent the standard error of the mean. Measurements were compared by ordinary two-way ANOVA. Tukey's multiple comparisons test was used to compare compounds at each timepoint. Statistical significance from Debio-1452 is indicated with asterisks (ns $p>0.05$, * $p<0.001$, ** $p<0.0001$).

The synthesis of the amine functionalized acryloaminopyridines was performed in a modular fashion with a late-stage Heck coupling of acrylamide 4 with functionalized naphthyridinones 5-7 (prepared as described in Scheme A) followed by deprotection of 8-10 to yield target amine-containing compounds 1-3. Compounds 1-3 were assessed for their ability to accumulate in *E. coli* MG1655 using the standard LC-MS/MS assay. While Debio-1452 showed no accumulation, compounds with ionizable nitrogens accumulated in *E. coli* as predicted by eNTRyway; the accumulation over the course of 2 h is shown in FIG. 6.

Debio-1452-NH3 retained potent antibacterial activity similar to parent Debio-1452 when assessed against Gramin these strains (MIC>32 μg/mL, FIG. 2); while compounds 2 and 3 are also active, Debio-1452-NH3 is the most active of the modified compounds (Table 2).

Figure 3:
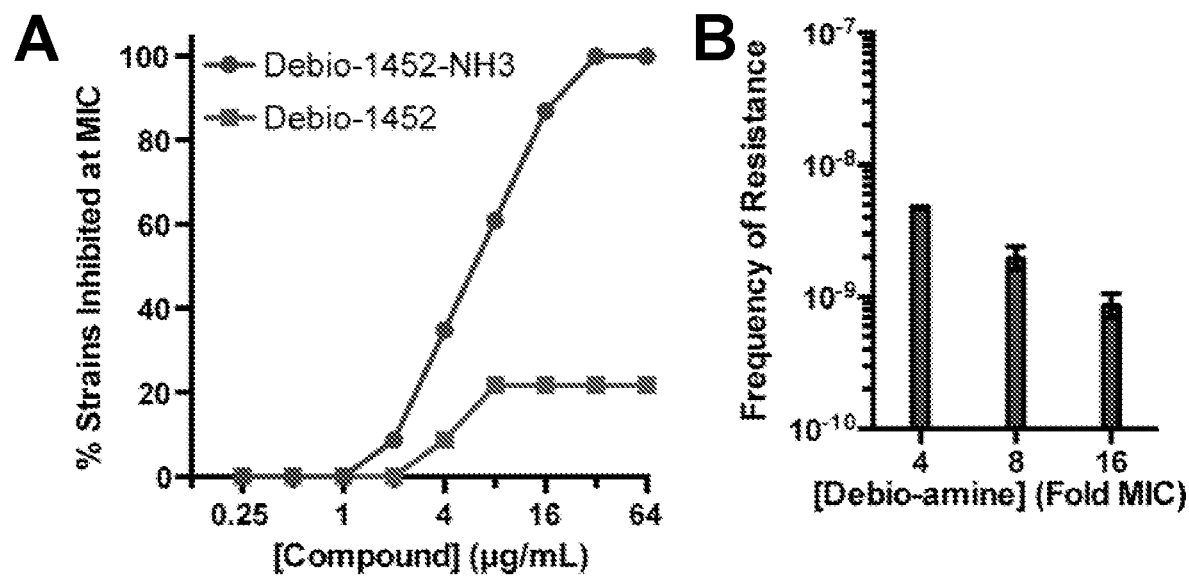
FIG. 3. A. Antimicrobial activity of Debio-1452 and Debio-1452-NH3 against a panel of Enterobacteriaceae clinical isolates. B. Spontaneous frequency of *E. coli* MG1655 resistance to Debio-1452-NH3 as a function of concentration. Data shown represent the average of three independent experiments. Error bars represent standard error of the mean. C. Relative prevalence of FabI mutants in *E. coli* resistant to Debio-1452-NH3. Resistant colonies of *E. coli* MG1655 were isolated following selection at 4- and 8-fold the MIC of Debio-1452-NH3. D. Fitness of *E. coli* isolates that harbor the FabI mutant conferring resistance to Debio-1452-NH3 (either A116V or G148S) were evaluated relative to parental strain. Data points represent average of four independent experiments. Error bars represent standard error of the mean. Measurements were compared by repeated measure two-way ANOVA. Tukey's multiple comparisons test was used to compare strains at each timepoint. Statistical significance from the wild-type strain (*E. coli* MG1655) is indicated with asterisks (* $p<0.05$,  $p<0.01$, * $p<0.001$, **** $p<0.0001$). E. Location of *E. coli* FabI mutations conferring resistance to Debio-1452-NH3 (red residues, A116V and G148S). PDB: 4JQC. F. In vitro inhibition of *E. coli* FabI and (G) the A116V FabI mutant by Debio-1452 and derivatives. Initial reaction rates were used to calculate percent activity relative to inhibitor-free reaction. Dose-response curves were fit to Morrison's quadratic to determine apparent K. Data is represented as average of three independent experiments. Error bars represent standard error of the mean.
Figure 3:
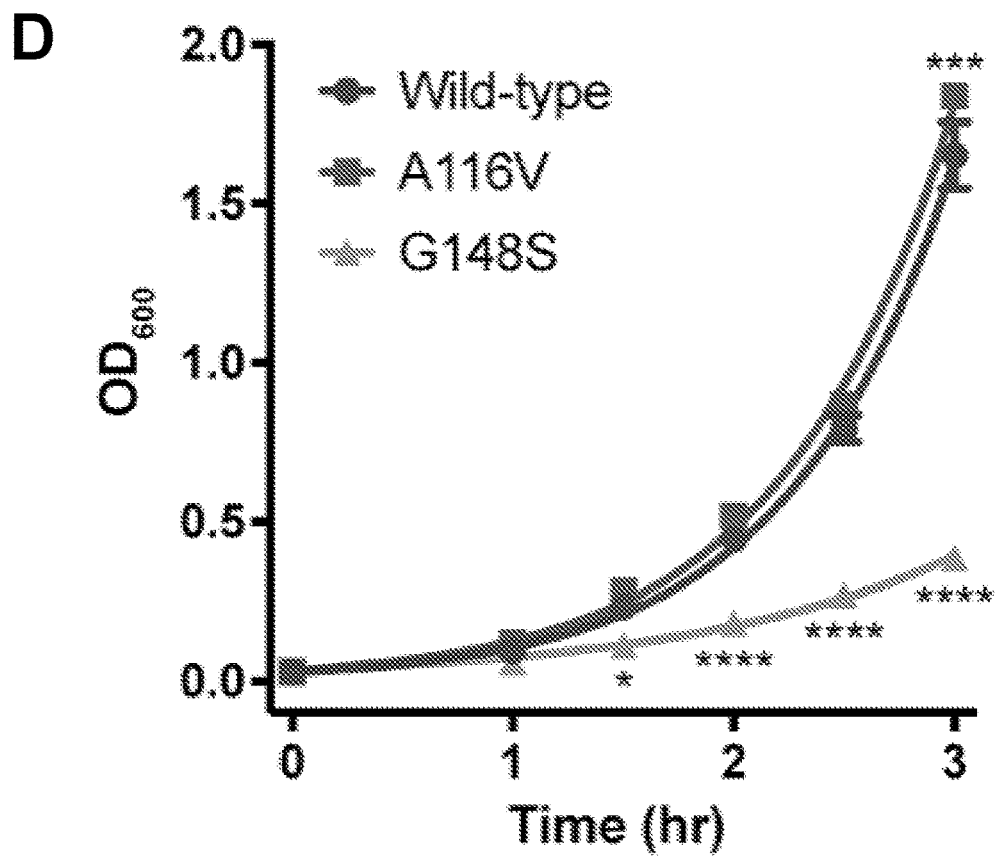
Figure 3:
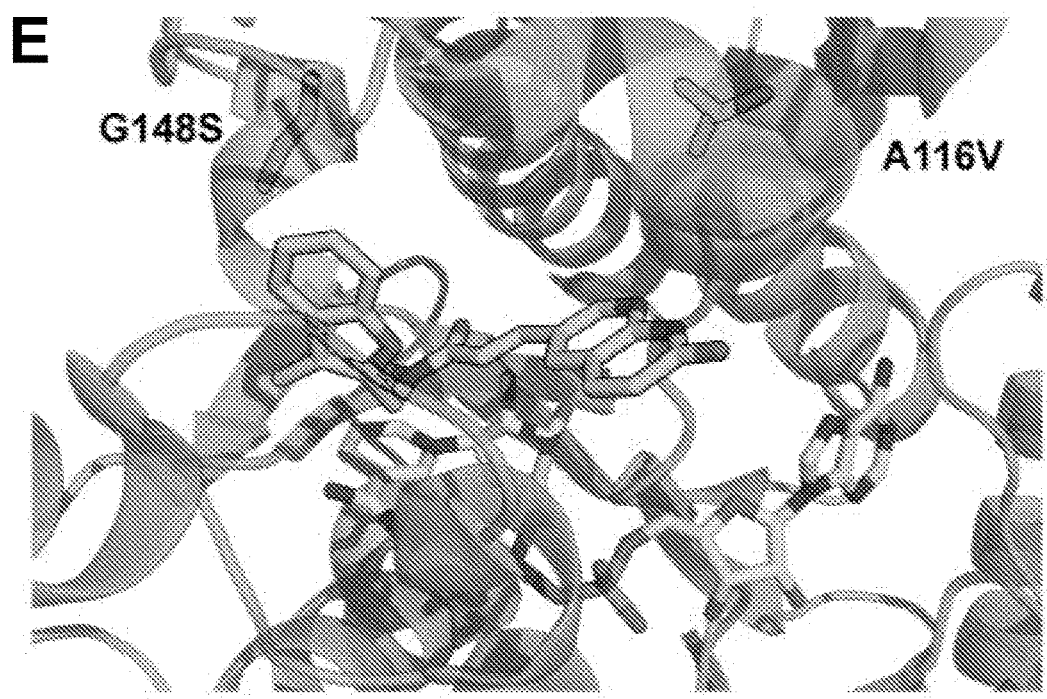
Figure 3:
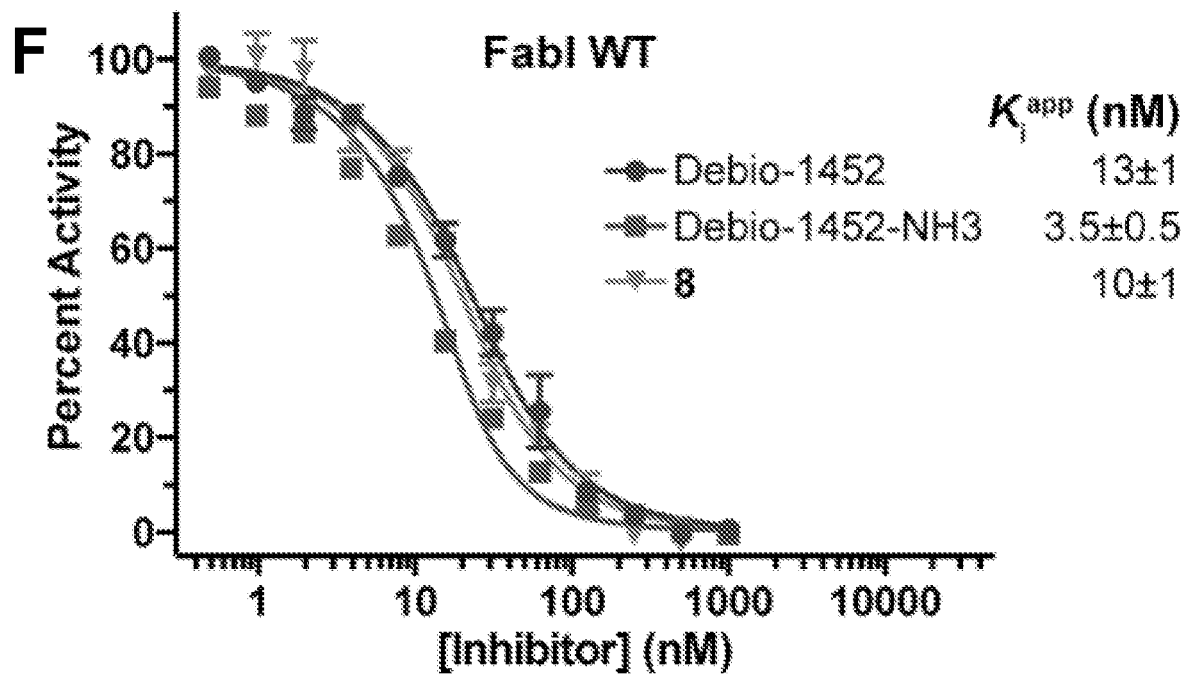
Figure 3:
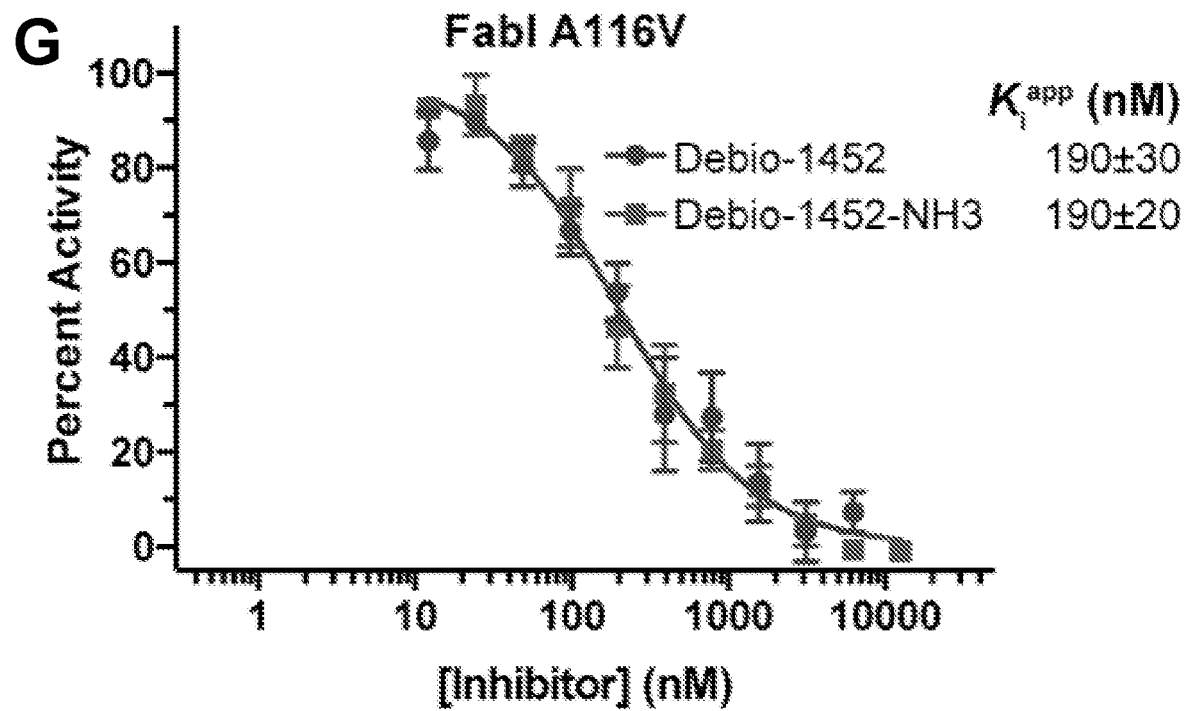

Debio-1452-NH3 is active against strains of Gram-negative pathogens *E. cloacae, K. pneumoniae*, and *A. baumannii*, with MIC values from 4-8 μg/mL, while Debio-1452 and compound 8 (possessing a non-ionizable nitrogen at the 3-position of the naphthryidinone ring) are very potent against *S. aureus* and *E. coli* ΔtolC and ΔrfaC strains, but have no activity against Gram-negatives with intact outer membranes (FIG. 2). As anticipated, amine analogues were not active against *P. aeruginosa* (FIG. 2 and Table 2), as these bacteria possess an additional FabI isoform, FabV, which enables rescue of the FASII pathway from inhibition of FabI. Debio-1452-NH3 was further evaluated for its antibiotic activity against a panel of clinical isolates. Multidrug-resistant Enterobacteriaceae clinical isolates were more susceptible to Debio-1452-NH3 than Debio-1452 (FIG. 3A).

Scheme A. Synthesis of Naphthyridinones and Debio-1452 Amine Containing Analogues.

Synthesis of Modified Napthyridinones 5-7:

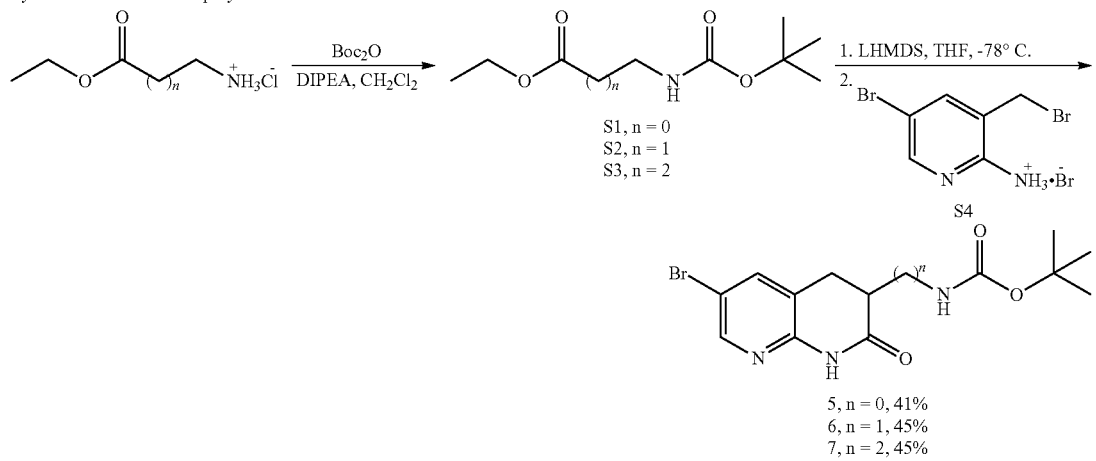

Synthesis of Debio-1452 Amine Containing Analogues 1-3:

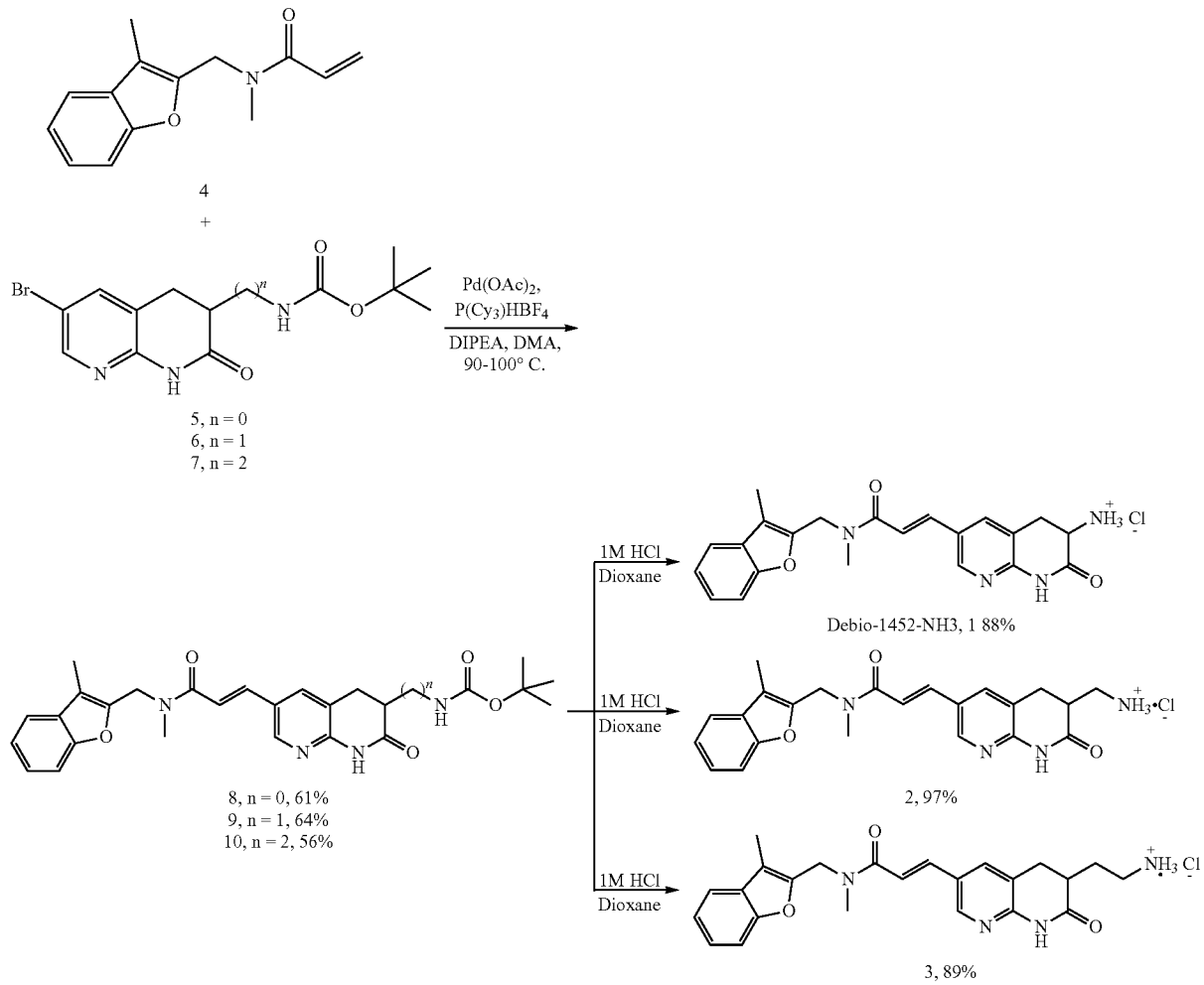

di-tert-butyl dicarbonate; DIPEA, diisopropylamine; LHMDS, Lithium bis(trimethylsilyl)amide; THF, tetrahydrofuran; Cy, cyclohexyl; DMA, dimethylacetamide.

To assess the antibacterial mode-of-action of Debio-1452-NH3, *E. coli* MG1655 colonies resistant to this compound were generated via the large-inoculum method. The frequency of resistance (FoR) for Debio-1452-NH3 was $10^{-8}$-$10^{-9}$ (FIG. 3B), similar to the FoR observed for Debio-1452 in *S. aureus* (J. Biol. Chem. 288, 36261-36271 (2013)). Sequencing of fabI in *E. coli* MG1655 resistant to Debio- 1452-NH3 revealed mutations near the active site of FabI, at positions A116 and G148 (FIG. 3C and FIG. 3E). *E. coli* harboring FabI A116V, which possessed MIC values of 64 μg/mL with Debio-1452-NH3, showed little impact on fitness as assessed by bacterial growth rates, while strains harboring FabI G148S, which possessed MIC values of >64 μg/mL, had significantly reduced fitness (FIG. 3D).

Key compounds were also evaluated for their ability to inhibit *E. coli* FabI in vitro utilizing a standard biochemical assay. The results of these experiments revealed Debio-1452, Debio-1452-NH3, and compound 8 to all be potent FabI inhibitors (FIG. 3F). Site directed mutagenesis of fabI allowed for production and in vitro enzymatic evaluation of the mutant enzymes, and the inhibitors showed reduced potency against FabI A116V (FIG. 3G). Taken together these results point to Debio-1452-NH3 killing Gram-negative bacteria through inhibition of FabI.

Debio-1452-NH3 showed little toxicity to mammalian cells grown in culture in 24 hour exposures (Table 2). In addition, the activity of Debio-1452-NH3 was only marginally altered (2-fold higher MIC) in the presence of serum, while Debio-1452 showed an 8-fold increase in MIC in the presence of serum (Table 2). The lack of mammalian cell toxicity and the small MIC shift in the presence of serum encouraged the exploration of Debio-1452-NH3 in vivo. Debio-1452-NH3 was found to be well tolerated in mice at doses of 50 mg/kg daily (IP injection, once-a-day for 5 days).

Figure 4:
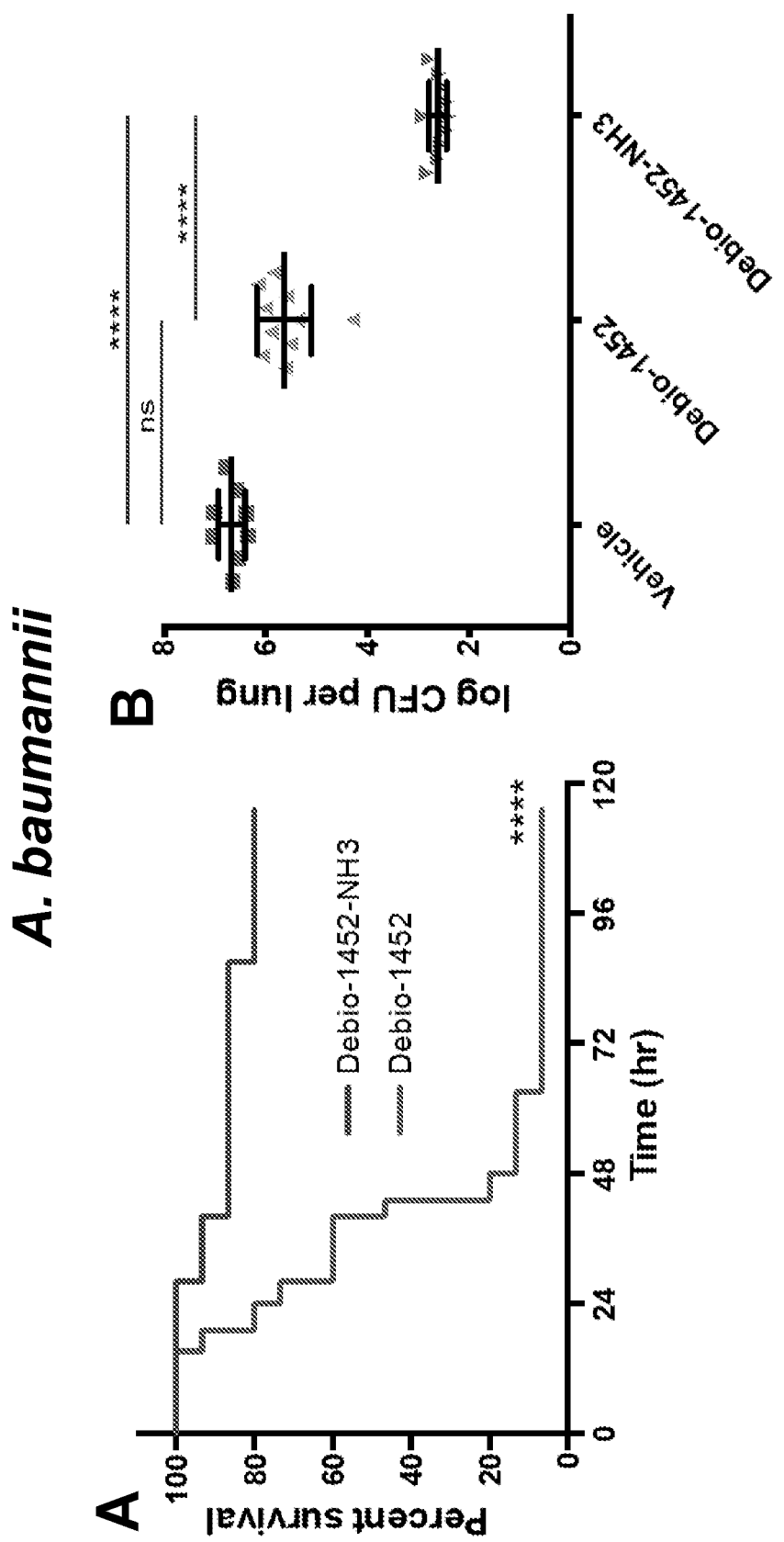
FIG. 4. In vivo efficacy of Debio-1452-NH3. A. Kaplan-Meier survival curve of mouse efficacy model of *A. baumannii* sepsis. Seven-week old CD-1 mice were infected with *A. baumannii* W41979 ($2.6\times10^8$ CFU/mouse, 15 mice per group) via IV injection. Mice were treated once-a-day for 4 days with FabI inhibitor (IV, 50 mg/kg). Log-rank test, $p<0.0001$. B. Acute pneumonia infections initiated in CD-1 mice with *A. baumannii* W41979 ($2.1\times10^8$ CFU/mouse, intranasal) were treated with vehicle (8 mice) or FabI inhibitor (10 mice per group) 8, 30, and 48 h post-infection (IV, 50 mg/kg), and the bacterial burden was evaluated 72 h post-infection. C. Kaplan-Meier survival curve of in vivo efficacy model of *K. pneumonia* sepsis. Seven-week old CD-1 mice were infected with *K. pneumoniae* BAA-1705 ($1.08\times10^8$ CFU/mouse, 15 mice per group) via IV injection. Mice were treated once-a-day for 4 days with FabI inhibitor (IV, 50 mg/kg). Log-rank test, $p<0.0001$. D. *K. pneumoniae* bacterial burden study. Acute pneumonia infections initiated in CD-1 mice with *K. pneumoniae* BAA-1705 ($4.4\times10^8$ CFU/mouse, intranasal) were treated with vehicle or FabI inhibitor (8 mice per group) 6, 23, and 45 h post-infection (IV, 50 mg/kg), and the bacterial burden was evaluated 72 h post-infection. E. Kaplan-Meier survival curve of in vivo efficacy model of *E. coli* sepsis. Seven-week old CD-1 mice were infected with *E. coli* AR-0493 ($1.6\times10^8$ CFU/mouse, 15 mice per group) via IV injection. Mice were treated once-a-day for 4 days with FabI inhibitor (IV, 50 mg/kg). Log-rank test, $p<0.001$. F. *E. coli* bacterial burden study. Acute pneumonia infections initiated in CD-1 mice with *E. coli* AR-0493 ($1.73\times10^8$ CFU/mouse, intranasal) were treated with vehicle or FabI inhibitor (8 mice per group) 6 and 28 h post-infection (IV, 50 mg/kg), and the bacterial burden was evaluated 48 h post-infection. Drugs were formulated in 20% sulfobutyl ether β-cyclodextrin from solid immediately before treatment. Statistical significance is indicated with asterisks (ns not significant, * $p<0.001$, ** $p<0.0001$).
Figure 4:
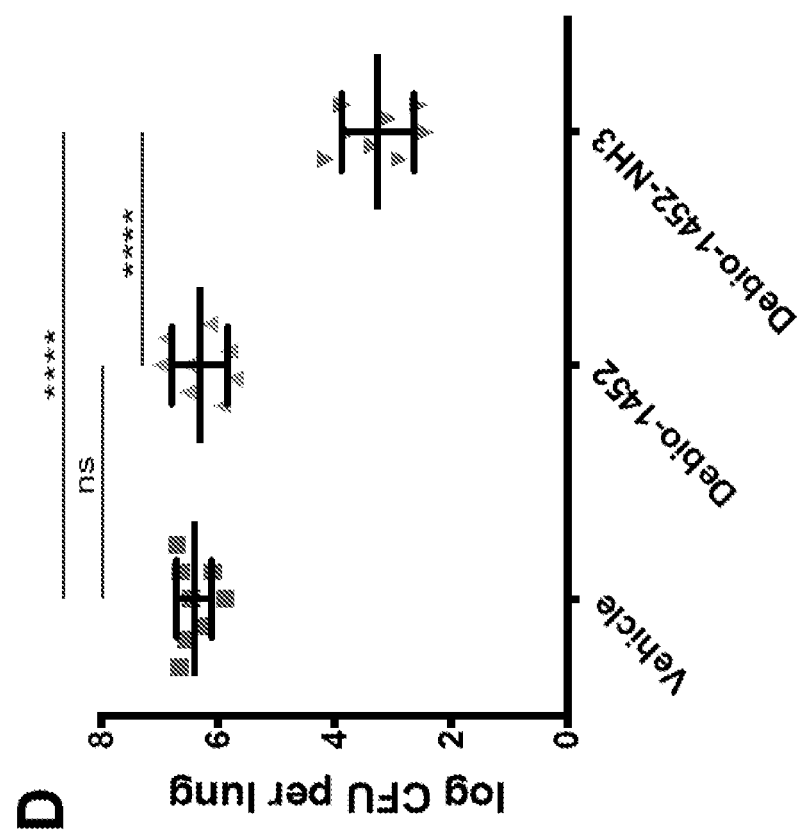
Figure 4:
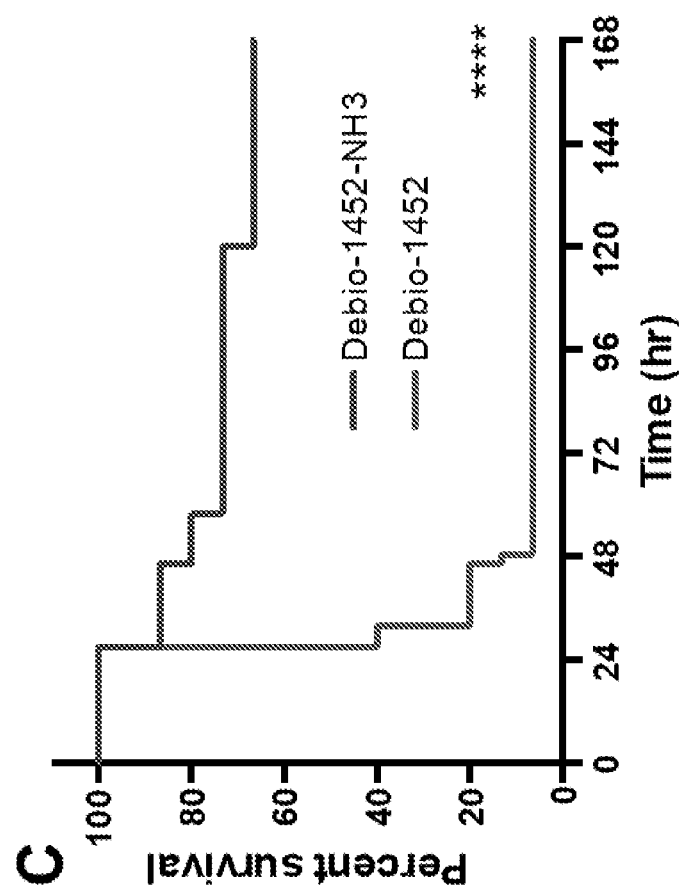
Figure 4:
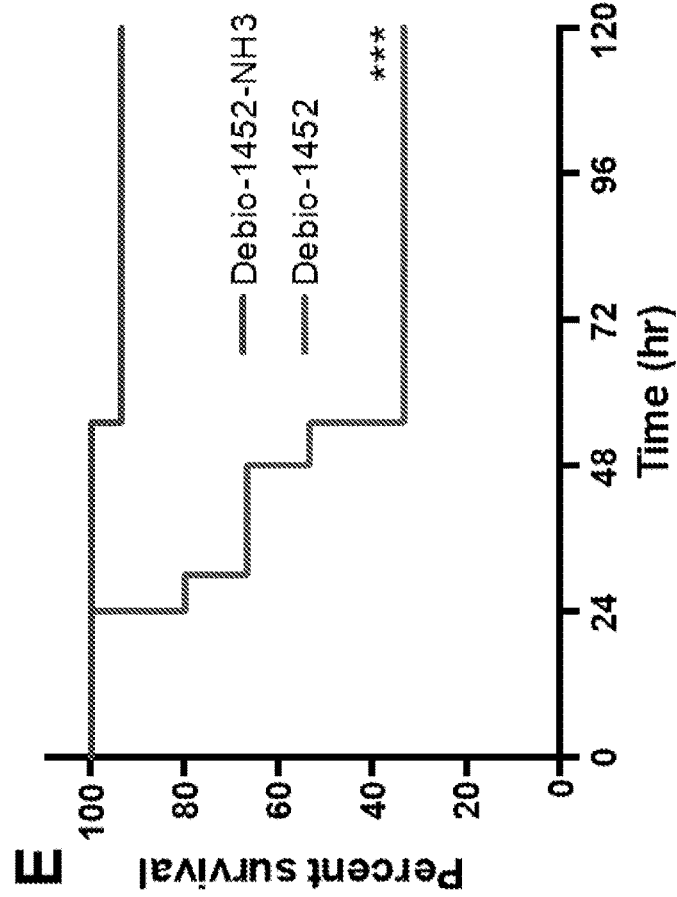

For the efficacy models Debio-1452 and Debio-1452-NH3 were assessed side-by-side in mouse models of infection with *A. baumannii*, *K. pneumonia*, and *E. coli*, evaluating both overall survival and bacterial burden for each type of infection. Mice were infected with *A. baumannii* W41979, a clinical isolate resistant to carbapenems and aminoglycosides, to induce sepsis. Four doses of Debio-1452 or Debio-1452-NH3 were administered once-per-day (50 mg/kg, IV) to separate groups of mice, resulting in significantly increased survival of the Debio-1452-NH3 treated mice (FIG. 4A), and other experiments with *A. baumannii* showed Debio-1452-NH3 reduced bacterial burden (FIG. 4B). Analogous experiments demonstrated the efficacy of Debio-1452-NH3 against mice infected with carbepenem-resistant *K. pneumoniae* and colistin-resistant *E. coli* (FIGS. 4C-4F).

TABLE 2

Antimicrobial susceptibility of clinical isolates to Debio-1452 and derivatives.

| | MIC (μg/mL) | | | | |
|---|---|---|---|---|---|
| Bacterial Strain | Debio-1452 | Debio-1452-NH3 | 2 | 3 | 8 |
| WT Gram-positive | | | | | |
| *S. aureus* ATCC 29213 | 0.008-0.016 | 0.03 | 0.03 | 0.125 | 0.016 |
| *S. aureus* ATCC 29213 (+50% Human serum) | 0.125 | 0.062 | | | |
| Gram-negative permeability mutant | | | | | |
| *E. coli* ΔtolC JW5503 | 0.031 | 0.062 | 0.125 | 0.062 | 0.125 |
| *E. coli* ΔrfaC JW3596 | 0.5 | 0.25 | 0.5 | 0.5 | 0.25 |
| WT Gram-negative | | | | | |
| *E. coli* MG1655 | >32 | 4 | 8 | 8 | >32 |
| *E. coli* BAA-2340 | >32 | 4 | | | >32 |
| *E. coli* BAA-2469 | 4 | 2 | 2 | | |
| *E. coli* BAA-2471 | 8 | 4 | 4 | | |
| *E. coli* F20987 | >32 | 4 | | | |
| *E. coli* M66623 | >32 | 8 | | | |
| *E. coli* AR-0346 | >32 | 8 | 4 | | |
| *E. coli* AR-0349 | 4 | 2 | 2 | | |
| *E. coli* AR-0493 | >32 | 4 | 4 | | >32 |
| *E. coli* AR-0495 | 8 | 4 | 2 | | |
| *E. cloacae* ATCC 29893 | >32 | 8 | | | >32 |
| *E. cloacae* BAA-2341 | >32 | 8 | 16 | | |
| *E. cloacae* BAA-2468 | >32 | 8 | 8 | | |
| *E. cloacae* S28901.1 | >32 | 16 | 8 | | |
| *K. pneumoniae* AR-0347 | >32 | 16 | 8 | | |
| *K. pneumoniae* BAA-1705 | >32 | 8 | 16 | | |
| *K. pneumoniae* BAA-2342 | >32 | 16 | 16 | | |
| *K. pneumoniae* BAA-2470 | 8 | 4 | 4 | | |
| *K. pneumoniae* BAA-2472 | >32 | 16 | 16 | | |
| *K. pneumoniae* BAA-2473 | >32 | 16 | 16 | | |
| *K. pneumoniae* M14723 | >32 | 16 | 16 | | |
| *K. pneumoniae* M67198 | >32 | 32 | 32 | | |
| *K. pneumoniae* M67297 | >32 | 32 | 32 | | |
| *K. pneumoniae* S20595 | >32 | 16 | 16 | | |
| *K. pneumoniae* S47889 | >32 | 8 | 8 | | >32 |
| *A. baumannii* W41979 | >32 | 4 | 16 | | >32 |
| *A. baumannii* F19521 | >32 | 4 | 16 | | |
| *A. baumannii* KB304 | >32 | 64 | 64 | | |
| *A. baumannii* KB343 | >32 | 64 | >64 | | |
| *A. baumannii* KB357 | >32 | 64 | >64 | | |
| *A. baumannii* M13100 | >32 | 16 | 16 | | |

TABLE 2-continued

Antimicrobial susceptibility of clinical isolates to Debio-1452 and derivatives.

| Bacterial Strain | MIC (µg/mL) | | | | |
| --- | --- | --- | --- | --- | --- |
| | Debio-1452 | Debio-1452-NH3 | 2 | 3 | 8 |
| A. baumannii WO22 | >32 | 64 | >64 | | |
| P. aeruginosa PA01 | >32 | >64 | | | >32 |
| Mammalian | | | | | |
| H. sapiens IMR-90 (% inhibition at 30 µM) | 16% | 30% | 48% | 12% | |

Compounds were evaluated against a panel of Gram-positive and Gram-negative organisms. MIC values were determined using the micro-dilution broth method as outlined by the Clinical and Laboratory Standards Institute (clsi.org/) and are listed in µg/mL. All experiments were performed in biological triplicate.

The extreme challenge of identifying novel classes of antibiotics for Gram-negative pathogens is apparent from the well-documented lack of success of large (millions of compounds) high-throughput screening campaigns, and this dearth of leads has directly led to the current situation where no new antibacterial classes for Gram-negative infections have been approved in over 50 years. Although most all Gram-positive-only compounds would kill Gram-negatives if they were not accumulation limited, in many cases even years of effort and the synthesis of hundreds of compounds has not provided Gram-negative active versions of high-value Gram-positive-only antibiotics. Thus, while optimization of bioavailability, solubility, and other important parameters has been a triumph of modern drug discovery, building in Gram-negative activity remains out of reach.

The description herein of eNTRyway should streamline Gram-negative antibiotic discovery efforts through its ability to predict bacterial accumulation in silico, therefore dramatically reducing the number of compounds that need to be synthesized and evaluated. Debio-1452 is an interesting case study, as the original lead was discovered in a high-throughput biochemical screen. The repeated inability to build-in whole cell permeability into lead compounds arising from biochemical screens, coupled with the reality that all classes of approved antibiotics were discovered in whole-cell screening, has led to the sensible suggestion that whole-cell screens be prioritized over target-based biochemical HTS in antibacterial drug discovery. However, the demonstration herein that eNTRyway can be used to rapidly generate FabI inhibitors with Gram-negative activity suggests the intriguing possibility that Gram-negative activity might also be readily built-in for other Gram-positive-only compounds, and also for some of the numerous existing hits from biochemical HTS. Indeed, as shown in FIG. 1B there are dozens of attractive starting points for these efforts, including many compounds that represent novel targets and would thus be less likely to encounter pre-existing resistance.

While appending of an amine onto an otherwise hydrophobic organic compound has the potential to be disruptive to target engagement, known structure-activity relationships and X-ray data can be leveraged to select the proper position for modification. The majority of compounds identified by eNTRyway as possessing good physiochemical properties have well-described SAR, published crystal structures, and target engagement validation (FIG. 1B). This abundance of characterization data engenders optimism that many of these compounds can be converted to versions with activity against Gram-negative pathogens. While the eNTRy rules were developed from studies on E. coli, the successful conversions of deoxynybomycin and now Debio-1452 to compounds that have activity against multiple Gram-negative ESKAPE pathogens suggests overlap in the chemical features required for compound accumulation in problematic Gram-negative organisms.

The dozens of antibiotics that are safe to humans that possess a primary amine demonstrate that there is no general problem with this functional group, but of course toxicity of any new compound will need to be evaluated. As demonstrated herein with Debio-1452-NH3, addition of a primary amine will likely provide a general in vivo pharmacokinetic advantage for an antibiotic (compared to the parent compound lacking an amine) in terms of reducing protein binding and enhancing activity in serum. The availability of eNTRyway allows rapid in silico prediction of compound accumulation in E. coli and subsequent prioritization of compounds to synthesize and evaluate. eNTRyway is one of a growing number of web tools designed to facilitate antibacterial research, and it is anticipated this web application will assist in the development of many antibiotics with activity against Gram-negative pathogens.

Conclusion. Gram-negative bacterial infections are a significant public health concern, and the lack of new drug classes for these pathogens is linked to the inability of most drug leads to accumulate inside Gram-negative bacteria. Herein is reported the development of a web application, called eNTRyway, which predicts compound accumulation (in E. coli) from its structure. eNTRyway was utilized to re-design Debio-1452, a Gram-positive-only antibiotic, into versions that accumulate in E. coli and possess antibacterial activity against high-priority Gram-negative pathogens. The lead compound Debio-1452-NH3 operates as an antibiotic via the same mechanism as Debio-1452, namely potent inhibition of the enoyl-acyl carrier protein reductase FabI. Debio-1452-NH3 reduces bacterial burden and rescues mice from lethal infections with clinical isolates of Acinetobacter baumannii, Klebsiella pneumonia, and Escherichia coli. This work provides tools for the facile discovery and development of antibiotics against Gram-negative bacteria, and a general blueprint for the conversion of Gram-positive-only compounds into broad-spectrum antibiotics.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the active compound in the proper medium. Absorption enhancers can also be used to increase the flux of the compound across the skin. The rate of such flux can be controlled by providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) *Harrison's Principles of Internal Medicine* 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent, concurrently or sequentially.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of solvates can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The invention now being generally described, it will be more readily understood by reference to the following examples which are included merely for purposes of illustration of certain aspects and embodiments of the present invention and are not intended to limit the invention.

Example 1-1: Materials and Methods

Bacterial strains. *S. aureus* ATCC 29213, *E. coli* MG1655, *E. coli* BAA-2340, *E. coli* BAA-2469, *E. coli* BAA-2471, *E. cloacae* BAA-2341, *E. cloacae* BAA-2468, *K. pneumoniae* BAA-1705, *K. pneumoniae* BAA-2342, *K. pneumoniae* BAA-2470, *K. pneumoniae* BAA-2472, and *K. pneumoniae* BAA-2473 were obtained from ATCC. *E. coli* JW5503 and *E. coli* JW3596 were obtained from the KEIO Collection. *E. cloacae* ATCC 29893 was provided by W. van der Donk (UIUC). *E. coli* AR-0346, *E. coli* AR-0349, *E. coli* AR-0493, *E. coli* AR-0495, and *K. pneumoniae* AR-0347 were obtained from the CDC and FDA AR Isolate Bank. *E. coli* F20987, *E. coli* M66623, *E. cloacae* S28901.1, *K. pneumoniae* M14723, *K. pneumoniae* M67198, *K. pneumoniae* M67297, *K. pneumoniae* S20595, *K. pneumoniae* S47889, *A. baumannii* W41979, *A. baumannii* F19521, *A. baumannii* M13100, and *A. baumannii* W022 were obtained from the University of Illinois Chicago Medical School. *A. baumannii* KB304, *A. baumannii* KB343, and *A. baumannii* KB357 were provided by J. Quale.

Antimicrobial susceptibility tests. Susceptibility testing was performed in biological triplicate, using the microdilution broth method as outlined by the Clinical and Laboratory Standards Institute. Bacteria were cultured with cation-adjusted Muller-Hinton broth (Sigma-Aldrich, Cat #90922) in round-bottom 96-well plates (Corning, Cat #3788). Human serum (pooled gender, 0.2 µm filtered) was purchased from BioIVT (Hicksville, N.Y.).

Accumulation assay. The accumulation assay was performed in triplicate in batches of twelve samples [4 compounds total, 3-time points, 1 sample/time point], with each batch containing tetracycline as a positive control. *E. coli* MG1655 was used for these experiments. For each replicate, 2.5 mL of an overnight culture of *E. coli* was diluted into 250 mL of fresh Luria Bertani (LB) broth (Lennox) and grown at 37° C. with shaking to an optical density ($OD_{600}$) of 0.70. The bacteria were pelleted at 3,220 r.c.f. for 10 min at 4° C. and the supernatant was discarded. The pellets were re-suspended in 40 ml of phosphate buffered saline (PBS) and pelleted as before, and the supernatant was discarded. The pellets were resuspended in 10.8 mL of fresh PBS and aliquoted into twelve 1.7 mL Eppendorf tubes (890 µL each). The number of colony-forming units (CFUs) was determined by a calibration curve. The samples were equilibrated at 37° C. with shaking for 5 min, compound was added (final concentration=50 µM), and then samples were incubated at 37° C. with shaking for either 10 min, 30 min, 1 hour, or 2 hours. These time points are short enough to minimize metabolic and growth changes (no changes in $OD_{600}$ or CFU count observed). After incubation, 800 µL of the cultures were carefully layered on 700 µL of silicone oil [9:1 AR20 (Acros, Cat #174665000)/Sigma High Temperature (Sigma-Aldrich, Cat #175633), cooled to −78° C.]. Bacteria were pelleted through the oil by centrifuging at 13,000 r.c.f. for 2 min at room temperature (supernatant remains above the oil); the supernatant and oil were then removed by pipetting. To lyse the samples, each pellet was re-suspended in 200 µL of water, and then they were subjected to three freeze-thaw cycle of three minutes in liquid nitrogen followed by three minutes in a water bath at 65° C. The lysates were pelleted at 13,000 r.c.f. for 2 min at room temperature and the supernatant was collected (180 µL). The debris was re-suspended in 100 µL of methanol and pelleted as before. The supernatants were removed and combined with the previous supernatants collected. Finally, remaining debris was removed by centrifuging at 20,000 r.c.f. for 10 min at room temperature. Supernatants were analyzed by LC-MS/MS.

Cell culture. IMR90 cells were obtained from ATCC. IMR90 cells were grown in EMEM with 10% fetal bovine serum (Gemini Benchmark, Cat #100-106), 100 U/mL penicillin, and 100 µg/mL streptomycin. All cells were cultured at 37° C. in a 5% $CO_2$ environment. Media was prepared by the Univeristy of Illinois School of Chemical Sciences Cell Media Facility. Sex and age of cell lines: IMR90 (Female, 16 weeks gestation).

Cell viability. Cells seeded (IMR90: 5,000 cells/well) a 96-well plate (Greiner Bio-One, Cat #655180) and were allowed to attach overnight. Cells were treated with investigational compounds in DMSO (30 µM, 1% DMSO final, 100 µL/well). Raptinal (100 µM) was used as a dead control. After 24 h post-treatment, media was exchanged with compound-free media. After 72 h post-treatment, cell viability was assessed using the Alamar Blue method. Stock Alamar Blue solution [10 µL, 440 µM resazurin (Sigma-Aldrich, Cat #R7017) in sterile 1×PBS] was added to each well, and plate was incubated for 3-4. Conversion of Alamar Blue was measured with plate reader (SpectraMax M3, Molecular Devices) by fluorescence (ex 555 nm, em 585 nm, cutoff 570 nm, autogain). Percent death was determined by normalizing to DMSO-treated cells and raptinal-treated cells.

Molecular docking. Docking of Debio-1452 derivatives into FabI crystal structures was performed with the Small-Molecule Drug Discovery Suite 2018-4 (Schrodinger, New York, N.Y.). Co-crystal structures of Debio-1452 bound to *E. coli* FabI (PDB: 4JQC) and *S. aureus* FabI (PDB: 4FS3)

were prepared using the Protein Prep Wizard with default settings and used to build receptor grids. For *S. aureus* FabI allowed rotation for Tyr157 and NADP hydroxyls. For *E. coli* FabI allowed rotation for Tyr156 and NAD hydroxyls. Positional constraints were applied on the benzofuran ring (center of mass must be within 2 Å of initial position). H-bonding constraints were applied to Tyr156 and Ala95 (*E. coli* numbering). Ligands were prepared with LigPrep and amines were protonated. Both enantiomers of each ligands were docked with Glide XP. The poses of higher scoring enantiomers were refined and $\Delta\Delta G_{bind}$ was calculated using Prime MM-GBSA. Protein residues within 5 Å of the ligand were sampled using the hierarchical sampling procedure in Prime MM-GBSA.

Selection of resistant mutants. Resistant mutants were selected via the large inoculum method. Briefly, *E. coli* MG1655 ($1.8 \times 10^9$ CFU) were plated on 100 mm plates of LB agar containing 64, 32, and 16 μg/mL Debio-1452-NH3. Colonies were visible after incubating at 37° C. for 48 h. Resistant colonies were confirmed by streaking on selective media with the same concentration of Debio-1452-NH3.

Sequencing of fabI. FabI was amplified by colony PCR. Colonies were picked and diluted in 100 μL sterile H$_2$O. PCR reactions are setup by combining 25 μL MiFi Mix (Bioline, London, UK), 1 μL 20 μM primer mix (EcFabI-PCR-FOR and EcFabI-PCR-REV), 10 μL template, and 14 μL H$_2$O. Reaction was performed on C1000 Thermal Cycler (Bio-Rad, Hercules, Calif.) with the following conditions: initial denature 95° C., 3 min; denature 95° C., 15 s; anneal 57° C., 15 s; extend 72° C., 30 s; final extend 3 min; 35 cycles. 5 μL portion of PCR reaction mixture was analyzed by agarose gel to confirm single 1.4 kbp product. PCR reaction was purified using GeneJET PCR Purification Kit (Thermo Scientific). PCR amplicons were submitted to the Core DNA Sequencing Facility at the University of Illinois at Urbana-Champaign for Sanger sequencing with overlapping internal primers (EcFabI-Seq-REV and EcFabI-Seq-REV). All primers were obtained from Integrated DNA Technologies (Coralville, Iowa).

TABLE 3

FabI Sequences.

| Primer | Sequence |
| --- | --- |
| EcFabI-PCR-FOR | 5'-GGGGCCAGCGTTTCTTTTTC-3' (SEQ ID NO: 1) |
| EcFabI-PCR-REV | 5'-AAACATGGAGACGGTGCTGG-3' (SEQ ID NO: 2) |
| EcFabI-Seq-FOR | 5'-ATAGCTACTCACAGCCAGGT-3' (SEQ ID NO: 3) |
| EcFabI-Seq-REV | 5'-GAAGGGGAGAAAGACGGATC-3' (SEQ ID NO: 4) |

Plasmids. Expression vectors for FabI were a generous gift from Peter Tonge (Stonybrook University, N.Y.). Site directed mutagenesis was performed with NEB Q5 Site Directed Mutagenesis Kit according to kit instructions with the primers and annealing temperatures listed below. Mutations were confirmed by Sanger sequencing using T7 promoter and T7 terminator primers.

TABLE 4

Species Mutations.

| Species | Mutation | Forward Primer | Reverse Primer | Ta |
| --- | --- | --- | --- | --- |
| *E. coli* | A116V | 5'-TTCAAAATTGT CCACGACATCAGCT C-3' (SEQ ID NO: 5) | 5'-GCCTTCACGGG TAACGGC-3' (SEQ ID NO: 6) | 67 |
| *E. coli* | G148S | 5'-TTCCTACCTTA GCGCTGAGCG-3' (SEQ ID NO: 7) | 5'-AGGGTCAGCAG GGCAGAA-3' (SEQ ID NO: 8) | 67 |

Expression and purification of *E. coli* FabI. *E. coli* BL21 (DE3) pLysS (Novagen) were transformed with pET15-ecFabI. Overnight culture (10 mL) in LB supplemented with 50 μg/mL ampicillin from single colony was diluted into 1 L LB+50 μg/mL ampicillin. Cells were grown at 37° C., 250 rpm until OD$_{600}$ reached 0.8. Culture was cooled to 18° C. and induced with 0.5 mM IPTG for 18 h at 18° C. Cells were harvested by centrifugation (5,000×g, 10 min, 4° C.). Cell pellets were flash frozen and store at −20° C. pending purification. Frozen cell pellets were thawed on ice and resuspended (5 mL per gram wet pellet, typically 20-30 mL) with 0.5% CHAPS, 1 mM PMSF, 1 μg/mL leupeptin, 1 μg/mL pepstatin A, and 2 μg/mL aprotinin in binding buffer [20 mM Tris (pH 7.9), 500 mM NaCl, 5 mM imidazole]. Cells were lysed by sonication on ice (30%, 10 s pulse, 20 s rest, 5 min total). Lysate was clarified by centrifugation (35,000×g, 1 h, 4° C.) and filtration through 0.2 μm syringe filter. Lysate was incubated with 5 mL Co-NTA agarose (HisPur cobalt resin, Thermo-Fisher Scientific Cat #89965, pre-equilibrated with binding buffer) for 30 min at 4° C. with gentle rocking. Agarose-containing lysate was transferred to column and flow through discarded. Column was washed with 2 column volumes of binding buffer followed by 10 column volumes of wash buffer [20 mM Tris (pH 7.9), 500 mM NaCl, 60 mM imidazole]. Protein was eluted with 15 mL elution buffer [20 mM Tris (pH 7.9), 500 mM NaCl, 300 mM imidazole]. Fractions containing protein were identified by SDS-PAGE, subjected to dialysis against FabI storage buffer [60 mM PIPES (pH 8.0), 150 mM NaCl, 1 mM EDTA], and concentrated with Amicon spin filter. Protein solution was aliquoted, flash frozen in liquid nitrogen, and stored at −80° C. Protein concentration was determined by BCA assay (ThermoFisher Cat #23227).

In vitro FabI inhibition assay. NADH (Sigma-Aldrich, Cat #N8129) and crotonoyl-CoA (Sigma-Aldrich, Cat #28007) were both diluted into activity buffer [100 mM potassium glutamate (pH 7.8)], and working solution was dispensed into two columns of round-bottom 96-well plate (330 μL per well). Inhibitors, dissolved in DMSO at 200× final concentration, were added to each well via multichannel pipette (2.48 μL per well). After thorough mixing, this mixture was transferred to UV-transparent plate (UV-STAR half-area 96-well plate, Greiner Bio-One, Cat #675801, 100 μL per well, three technical replicates per inhibitor concentration). Plate was placed in plate-reader (SpectraMax 190, Molecular Devices) under temperature control (25° C.), and temperature was allowed to equilibrate. Fresh aliquot of enzyme from −80° C. was thawed on ice and diluted in activity buffer. Enzyme working solution was added to plate (50 µL per well, 20 nM enzyme final). After shaking for 5 s, reaction progress was monitored by absorbance at 340 nm every 15 s for 90 min. Linear portion of reaction progress curve was fit using plate-reader software (SoftMax Pro 7.0). Percent activity was calculated relative to DMSO-only and no-enzyme controls in each plate. Percent activity curves were fit to Morrison's quadratic using Graphpad Prism 6.0 to obtain apparent K.

Mouse MTD of Debio-1452-NH3. The protocol was approved by the IACUC at the University of Illinois at Urbana-Champaign (Protocol Number:16144). In these studies, 10- to 12-week-old female C57BL/6 mice purchased from Charles River were used. The maximum tolerate dose (MTD) of single compound was determined first. Debio-1452 amine analogues were formulated in 20% sulfobutyl ether β-cyclodextrin in sterile water. Debio-1452-NH3 (1), and compounds 2 and 3 were given by IP injection and mice were monitored for signs of toxicity for 2 weeks (single dose). For multiple dose, the compound was given by daily IP for 5 consecutive days and mice were monitored for signs of toxicity for 1 month. MTD was the highest dosage with acceptable toxicity (e.g. <20% weight loss). Single dose MTDs were initially determined. Debio-1452-NH3 (1) was well tolerated at a single dose of 50 mg kg$^{-1}$ and compound 3 was well tolerated at a single dose of 100 mg kg$^{-1}$. Further analysis showed that Debio-1452-NH3 (1) was well tolerated with daily dosing of 50 mg kg$^{-1}$ for 5 consecutive days. The MTD of Debio-1452-NH3 (1) was used to inform the dosing schedule used in subsequent efficacy studies.

Bacterial sepsis survival model. The protocol was approved by the IACUC at the University of Illinois at Urbana-Champaign (Protocol Number: 17271). Six-week-old CD-1 mice were purchased from Charles River and acclimated for 4-7 days. All animals were housed in a pathogen-free environment and received sterile food and water. For the preparation of each inoculum, overnight cultures of clinical isolates were diluted into LB broth and grown to log-phase growth at 37° C. Infection was established via 100 µL retro-orbital injection of bacteria: *A. baumannii* (W41979) 2.6×10$^8$ CFU/mouse, *K. pneumoniae* (BAA-1705) 1.08×10$^8$ CFU/mouse, or *E. coli* (AR-0493) 1.6×10$^8$ CFU/mouse. Mice were treated once-a-day for four days with either Debio-1452 Tosylate or Debio-1452-NH3 (retro-orbital, 50 mg/kg). Drugs were formulated in 20% sulfobutyl ether β-cyclodextrin from solid before treatment. For survival analyses, a Kaplan-Meier Log Rank Survival Test was performed using GraphPad Prism 6.0.

Acute pneumonia bacterial burden model. The protocol was approved by the IACUC at the University of Illinois at Urbana-Champaign (Protocol Number: 17271). Six-week-old CD-1 mice were purchased from Charles River and acclimated for 4-7 days. All animals were housed in a pathogen-free environment and received sterile food and water. For the preparation of each inoculum, overnight cultures of clinical isolates were diluted into LB broth and grown to log-phase growth at 37° C. Lung infection was established via intranasal inoculation of bacteria: *A. baumannii* (W41979) 2.1×10$^8$ CFU/mouse, *K. pneumoniae* (BAA-1705) 4.4×10$^8$ CFU/mouse, or *E. coli* (AR-0493) 1.73×10$^8$ CFU/mouse. Infected mice were then treated once daily for three days with either vehicle, Debio-1452 Tosylate, or Debio-1452-NH3 (retro-orbital, 50 mg/kg). Drugs were formulated in 20% sulfobutyl ether β-cyclodextrin from solid immediately before treatment. At 48 h post-infection (*E. coli*) or 72 h post-infection (*A. baumannii* and *K. pneumoniae*), CFU were determined in the lungs through serial dilutions. Statistical significance was determined by two-way ANOVA with Tukey's multiple comparison tests.

Statistical analyses. GraphPad Prism 6.0 was used for data analysis and figure generation. Data are shown as the mean±s.e.m. Statistical significance was determined by t-tests (two-tailed) for two groups or two-way ANOVA (with Tukey's multiple comparisons tests) for three or more groups. Survival curves were compared using the log-rank test. P<0.05 was considered statistically significant. In this study, no statistical methods were used to predetermine sample size. The experiments were not randomized, and the investigators were not blinded to allocation during the experiments and outcome assessments.

Code availability. Source code for eNTRyway for local use is available on Github: (github.com/HergenrotherLab/entry-cli).

Materials and Methods for Chemical Synthesis. All reactions were performed under inert atmosphere using nitrogen gas unless otherwise specified. Chemical reagents were purchased from commercial sources and used without further purification. Debio-1452 used for in vitro and cell-based studies was purchased from MedChemExpress. Anhydrous solvents were either purchased from commercial suppliers or dried after being passed through columns packed with activated alumina under positive pressure of nitrogen using a PureSolv MD-5 (Inert previously Innovative Technology inc.) solvent purification system. Final compounds were dried in an Abderhalden drying pistol to remove any residual solvents. $^1$H NMR, $^{13}$C NMR, and 2D NMR experiments for prepared intermediates and products were recorded on a Varian Unity Inova 600 MHz NMR system equipped with an autoX broadband probe and/or a Bruker Avance III HD 500 MHz NMR system equipped with a CryoProbe. Spectra were obtained in the following solvents (reference peaks also included for $^1$H and $^{13}$C NMRs: Deuterated Chloroform-d ($^1$H NMR 7.26 ppm; $^{13}$C NMR 77.16 ppm), DMSO-d$_6$ ($^1$H NMR 2.50 ppm; $^{13}$C NMR 39.52 ppm). All the chemical shifts are expressed in ppm (δ), coupling constants (J, Hz) and peak patterns are reported as broad (br), singlet (s), doublet (d), triplet (t), quartet (q) and multiplet (m). High resolution mass spectra (HRMS) were obtained in the School of Chemical Sciences Mass Spectrometry Laboratory on a Waters Q-TOF Ultima quadrupole time of flight spectrometer using electrospray ionization ESI. Purity of the final compounds were purified to >95% as assessed by an Agilent Technologies 1290 Infinity II UHPLC equipped with a Phenomenex Kinetex column (2.1 mm ID×50 mm, 1.7 µm particle size, 100 Å pore size).

Scheme B. Synthesis of Naphthyridinone Presursors and Debio-1452 Amine Containing Analouges.

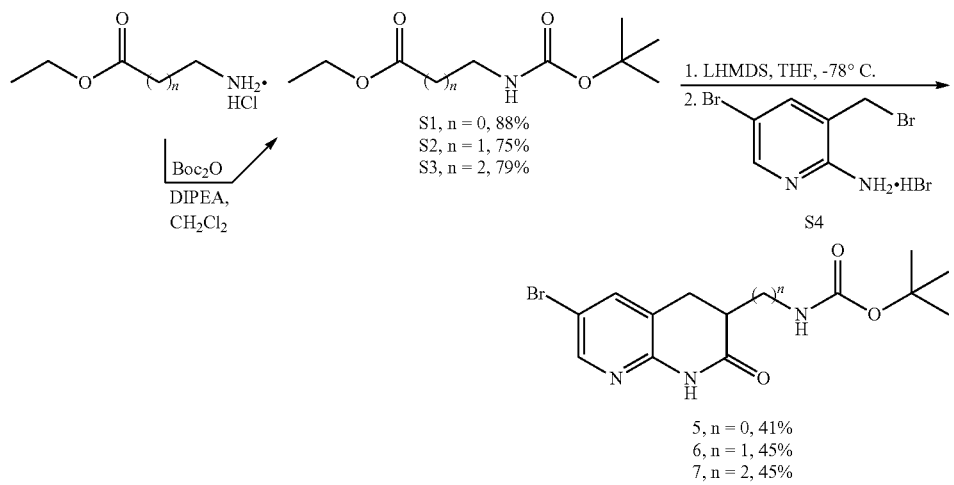

S1, n = 0, 88%
S2, n = 1, 75%
S3, n = 2, 79%

5, n = 0, 41%
6, n = 1, 45%
7, n = 2, 45%

Boc$_2$O, di-tert-butyl dicarbonate; DIPEA, N.N-diisopropylethylamne; LHMDS, lithium bis(trimethylsulyl)amide; THF, tetrahydrofuran.

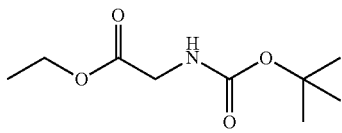

S1 ethyl (tert-butoxycarbonyl)glycinate (S1)-N,N-diisopropylethylamine (2.2 eq, 44 mmol) was added dropwise to a solution of glycine ethyl ester hydrochloride (1 eq, 20 mmol) in CH$_2$Cl$_2$ (80 mL) at 0° C. followed by the dropwise addition of di-tert-butyl dicarbonate (1.1 eq, 22 mmol). The reaction mixture was allowed to warm to room temperature and stirred for 1.5 h. The reaction was quenched with saturated aqueous ammonium chloride and extracted with dichloromethane. The combined organic extracts were washed with saturated aqueous sodium bicarbonate, dried over sodium sulfate, and concentrated under reduced pressure. Purification by flash purification column chromatography (10:40:50, EtOAc:CH$_2$Cl$_2$:Hexanes) yielded ethyl (tert-butoxycarbonyl)glycinate (S1, 3.58 g, 17.6 mmol, 88%) as a colorless oil. $^1$H NMR (500 MHz, Chloroform-d): δ 5.00 (s, 1H), 4.21 (q, J=7.1 Hz, 2H), 3.90 (d, J=5.6 Hz, 2H), 1.45 (s, 9H), 1.28 (t, J=7.2 Hz, 3H). $^{13}$C NMR (126 MHz, Chloroform-d): 170.49, 155.83, 80.11, 61.48, 42.62, 28.47, 14.31.

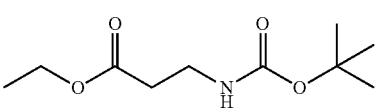

S2 ethyl 3-((tert-butoxycarbonyl)amino)propanoate (S2)-N,N-diisopropylethylamine (2.2 eq, 44 mmol) was added dropwise to a solution of β-alanine ethyl ester hydrochloride (1 eq, 20 mmol) in CH$_2$Cl$_2$ (80 mL) at 0° C. followed by the dropwise addition of di-tert-butyl dicarbonate (1.1 eq, 22 mmol). The reaction mixture was allowed to warm to room temperature and stirred for 1.5 h. The reaction was quenched with saturated aqueous ammonium chloride and extracted with dichloromethane. The combined organic extracts were washed with saturated aqueous sodium bicarbonate, dried over sodium sulfate, and concentrated under reduced pressure. Purification by flash purification column chromatography (10:40:50, EtOAc:CH$_2$Cl$_2$:Hexanes) yielded ethyl 3-((tert-butoxycarbonyl)amino)propanoate (S2, 3.25 g, 15.0 mmol, 75%) as a colorless oil. $^1$H NMR (500 MHz, Chloroform-d): δ 5.01 (s, 1H), 4.15 (q, J=7.2 Hz, 2H), 3.48-3.27 (m, 2H), 2.51 (t, J=6.1 Hz, 2H), 1.43 (s, 9H), 1.26 (t, J=7.1 Hz, 3H). $^{13}$C NMR (126 MHz, Chloroform-d): δ 172.64, 155.92, 79.48, 60.78, 36.26, 34.81, 28.54, 14.35.

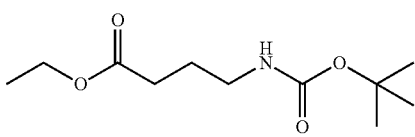

S3 ethyl 4-((tert-butoxycarbonyl)amino)butanoate (S3)-N,N-diisopropylethylamine (2.2 eq, 44 mmol) was added dropwise to a solution of ethyl 4-aminobutyrate hydrochloride (1 eq, 20 mmol) in CH$_2$Cl$_2$ (80 mL) at 0° C. followed by the dropwise addition of di-tert-butyl dicarbonate (1.1 eq, 22 mmol). The reaction mixture was allowed to warm to room temperature and stirred for 1.5 h. The reaction was quenched with saturated aqueous ammonium chloride and extracted with dichloromethane. The combined organic extracts were washed with saturated aqueous sodium bicarbonate, dried over sodium sulfate, and concentrated under reduced pressure. Purification by flash purification column chromatography (10:40:50, EtOAc:CH$_2$Cl$_2$:Hexanes) yielded ethyl 4-((tert-butoxycarbonyl)amino)butanoate (S3, 3.66 g, 15.8 mmol, 79%) as a colorless oil. $^1$H NMR (500 MHz, Chloroform-d): δ 4.62 (s, 1H), 4.13 (q, J=7.2 Hz, 2H), 3.25-3.06 (m, 2H), 2.34 (t, J=7.3 Hz, 2H), 1.81 (p, J=7.2 Hz, 2H), 1.43 (s, 9H), 1.25 (t, J=7.1 Hz, 3H). $^{13}$C NMR (126 MHz, Chloroform-d): δ 173.42, 156.06, 79.34, 60.59, 40.11, 31.77, 28.55, 25.45, 14.37.

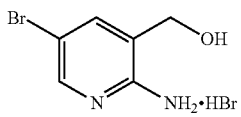

S4 Precursor (2-amino-5-bromopyridin-3-yl)methanol hydrobromide (S4 Precursor)—Bromine (1.01 eq, 39.02 mmol) was added dropwise to a solution of 2-amino-3-(hydroxymethyl)pyridine (1 eq, 38.6 mmol) in glacial acetic acid (60 mL) cooled in an ice bath. After the addition of bromine was complete, the reaction mixture was returned to room temperature. After stirring overnight, the reaction mixture was filtered and washed several times with ether to yield (2-amino-5-bromopyridin-3-yl)methanol hydrobromide (S4 Precursor, 10.01 g, 35.5 mmol, 92% yield) as a yellow solid. (HBr Salt)$^1$H NMR (500 MHz, DMSO-$d_6$): δ 8.17 (d, J=2.3 Hz, 1H), 7.97-7.93 (m, 1H), 4.41 (s, 2H). $^{13}$C NMR (126 MHz, DMSO-$d_6$): δ 151.39, 141.11, 135.60, 127.72, 104.27, 57.98.

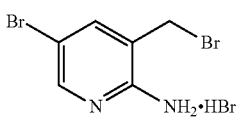

S4

5-bromo-3-(bromomethyl)pyridin-2-amine hydrobromide (S4)—A suspension of (2-amino-5-bromopyridin-3-yl)methanol hydrobromide (1 eq, 35.47 mmol) in 48% hydrobromic acid (70 mL) was refluxed for 10 h. After 10 h, the reaction mixture was allowed to slowly cool to room with stirring, filtered, and rinsed with ethyl acetate. The solid was triturated with ethyl acetate to yield 5-bromo-3-(bromomethyl)pyridin-2-amine hydrobromide (S4, 10.226 g, 29.7 mmol, 84%) as a light beige solid. $^1$H NMR (500 MHz, DMSO-$d_6$): δ 8.18 (d, J=2.4 Hz, 1H), 8.15 (d, J=2.4 Hz, 1H), 4.72 (s, 2H). $^{13}$C NMR (126 MHz, DMSO): δ 153.04, 144.29, 141.01, 121.66, 104.11, 29.13.

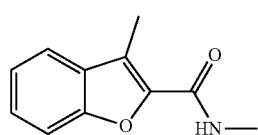

4 Precursor A

N,3-dimethylbenzofuran-2-carboxamide (4 Precursor a)—To a solution of 3-methylbenzo[b]furan-2-carboxylic acid (1 eq, 52 mmol), methylamine hydrochloride (1.1 eq, 57.52 mmol), N,N-diisopropylethylamine (2.2 eq, 114.4 mmol), and HOBt (1.1 eq, 57.52 mmol) in DMF (150 mL) was added EDC (1.1 eq, 57.52 mmol). The reaction mixture was heated to 70° C. overnight. The solvent was reduced to a few mL. The crude reaction mixture was diluted with $CH_2Cl_2$ and washed with saturated aqueous sodium bicarbonate. The organic extracts were dried over sodium sulfate and concentrated under reduced pressure. Purification by flash column chromatography (4 Precursor a, 20:50:30, EtOAc:$CH_2Cl_2$:hexanes) yielded N,3-dimethylbenzofuran-2-carboxamide (9.24 g, 48.9 mmol, 94%) as a white solid. $^1$H NMR (500 MHz, Chloroform-d): δ 7.61 (dt, J=7.8, 1.0 Hz, 1H), 7.45-7.36 (m, 2H), 7.29 (ddd, J=8.0, 6.4, 1.7 Hz, 1H), 6.64 (s, 1H), 3.03 (d, J=5.0 Hz, 3H), 2.63 (s, 3H). $^{13}$C NMR (126 MHz, Chloroform-d): δ 161.10, 153.35, 142.96, 129.95, 127.04, 123.19, 122.19, 121.07, 111.55, 25.86, 9.00.

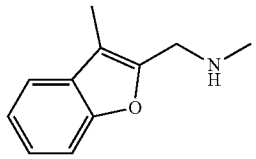

4 Precursor b

N-methyl-1-(3-methylbenzofuran-2-yl)methanamine (4 Precursor b)—Lithium aluminum hydride (3 eq, 47.6 mmol) was added portionwise to a solution of N,3-dimethylbenzofuran-2-carboxamide (1 eq, 15.86 mmol) in THF (75 mL) at room temperature. The reaction mixture was refluxed for 11 h. After reaction completion, the reaction mixture was cooled to 0° C. and slowly quenched by the sequential addition of 2 mL water, 2 mL 15% sodium hydroxide, 6 mL water at 15-30 min intervals. The mixture was filtered through a pad of celite rinsed several times with ethyl acetate. Purification by flash column chromatography (5:95, MeOH:$CH_2Cl_2$) yielded N-methyl-1-(3-methylbenzofuran-2-yl)methanamine (4 Precursor b, 2.513 g, 14.3 mmol, 91%). $^1$H NMR (500 MHz, Chloroform-d): δ 7.49-7.44 (m, 1H), 7.43-7.37 (m, 1H), 7.27-7.23 (m, 1H), 7.22 (td, J=7.3, 1.3 Hz, 1H), 3.87 (s, 2H), 2.45 (s, 3H), 2.23 (s, 3H). $^{13}$C NMR (126 MHz, Chloroform-d): δ 154.25, 151.34, 130.08, 124.01, 122.26, 119.28, 112.33, 111.04, 46.23, 35.80, 8.07.

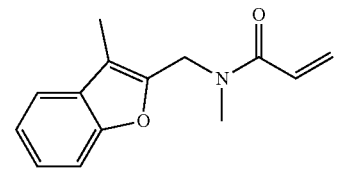

4

N-methyl-N-((3-methylbenzofuran-2-yl)methyl)acrylamide (4)—N,N-diisopropylethylamine (1.5 eq, 15.4 mmol) was added dropwise to a solution of N-methyl-1-(3-methylbenzofuran-2-yl)methanamine (1 eq, 10.3 mmol) in $CH_2Cl_2$ (75 mL) at room temperature. After 10 min, acryloyl chloride (2 eq, 20.6 mmol) was added dropwise and the reaction mixture was stirred overnight. The solvent was removed under reduced pressure and purification by flash column chromatography (1:99 to 3:97, MeOH:$CH_2Cl_2$) yielded N-methyl-N-((3-methylbenzofuran-2-yl)methyl)acrylamide (4, 1.861 g, 8.12 mmol, 79%) as a colorless oil. Note: Tabulated NMR data for acrylamide derivatives consist of two rotamers that exist at room temperature in a ratio of 35:65 and is reflected in the reported integral values. $^1$H NMR (500 MHz, Chloroform-d): 7.51-7.45 (m, 1H), 7.43-7.36 (m, 1H), 7.32-7.18 (m, 2H), 6.85 (dd, J=16.8, 10.6 Hz, 0.35H), 6.59 (dd, J=16.7, 10.4 Hz, 0.65H), 6.42-6.33 (m, 1H), 5.80-5.67 (m, 1H), 4.77 (s, 1.3H), 4.62 (s, 0.7H), 3.13 (s, 1.95H), 3.02 (s, 1.05H), 2.29 (s, 1.95H), 2.25 (s, 1.05H). Note: Tabulated NMR data for acrylamide derivatives consist of two rotamers that exist at room temperature which results in doubling of signals for most $^{13}$C nuclei. $^{13}$C NMR (126 MHz, Chloroform-d): 167.07, 166.29, 154.26, 154.23, 148.93, 147.52, 129.84, 129.48, 128.48, 128.22, 128.04, 127.54, 124.75, 124.30, 122.59, 122.37, 119.49, 113.74, 113.36, 111.20, 111.07, 45.21, 42.26, 35.36, 33.64, 7.95.

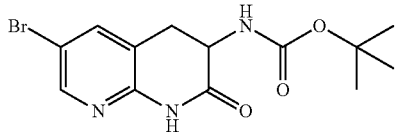

tert-butyl (6-bromo-2-oxo-1,2,3,4-tetrahydro-1,8-naphthyridin-3-yl)carbamate (5). To a solution of LHMDS (1 M in THF, 4 eq, 33.4 mmol) cooled to −78° C. was added a solution of ethyl (tert-butoxycarbonyl)glycinate (S1, 2 eq, 16.72 mmol) in THF (34 mL) dropwise. The reaction mixture was stirred for 1 h followed by the portionwise addition (3 portions at 15 min intervals) of 5-bromo-3-(bromomethyl)pyridin-2-amine hydrobromide (S4, 1 eq, 8.36 mmol) via a solid addition tube kept under $N_2$. The reaction mixture was kept at −78° C. for several hours and allowed to warm to −40° C. overnight. The reaction mixture was quenched with 0.5M HCl(aq) and extracted with ethyl acetate. The combined organic extracts were dried over sodium sulfate and concentrated under reduced pressure. Purification by flash purification column chromatography (01:99 to 10:90, THF:$CH_2Cl_2$) followed by trituration with ether/n-pentane yielded tert-butyl (6-bromo-2-oxo-1,2,3,4-tetrahydro-1,8-naphthyridin-3-yl)carbamate (5, 1.48 g, 3.46 mmol, 41%) as a white solid. $^1$H NMR (500 MHz, Chloroform-d): δ 9.68 (s, 1H), 8.32 (s, 1H), 7.65 (s, 1H), 5.63 (s, 1H), 4.42-4.30 (m, 1H), 3.52 (dd, J=16.4, 6.4 Hz, 1H), 2.83 (t, J=14.9 Hz, 1H), 1.48 (s, 9H). $^{13}$C NMR (126 MHz, Chloroform-d): δ 169.16, 155.72, 148.68, 147.95, 139.50, 119.83, 114.37, 80.54, 49.85, 31.17, 28.48. HRMS (ESI): m/z calc for $C_{13}H_{16}BrN_3O_3[M+H]^+$: 342.0448, found: 342.0451.

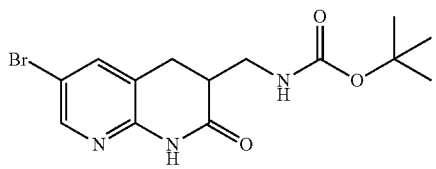

tert-butyl ((6-bromo-2-oxo-1,2,3,4-tetrahydro-1,8-naphthyridin-3-yl)methyl)carbamate (6). To a solution of LHMDS (1 M in THF, 4 eq, 36 mmol) cooled to −78° C. was added a solution ethyl 3-((tert-butoxycarbonyl)amino)propanoate (S2, 2 eq, 18 mmol) in THF (36 mL) dropwise. The reaction mixture was stirred for 1.5 h followed by the portionwise addition (3 portions at 15 min intervals) of 5-bromo-3-(bromomethyl)pyridin-2-amine hydrobromide (S4, 1 eq, 9 mmol) via a solid addition tube kept under $N_2$. The reaction mixture was kept at −78° C. for several hours and allowed to warm to −40° C. overnight. The reaction mixture was quenched with 0.5M HCl(aq) and extracted with ethyl acetate. The combined organic extracts were dried over sodium sulfate and concentrated under reduced pressure. Purification by flash purification column chromatography (01:99 to 10:90, THF:$CH_2Cl_2$) followed by trituration with ether/n-pentane yielded tert-butyl ((6-bromo-2-oxo-1,2,3,4-tetrahydro-1,8-naphthyridin-3-yl)methyl)carbamate (6, 1.431 g, 4.02 mmol, 45%) as a white solid. $^1$H NMR (500 MHz, Chloroform-d): δ 9.38 (s, 1H), 8.28 (s, 1H), 7.63 (s, 1H), 5.31 (d, J=6.9 Hz, 1H), 3.71-3.55 (m, 1H), 3.48 (dt, J=13.7, 6.3 Hz, 1H), 2.95 (dd, J=16.1, 6.9 Hz, 1H), 2.89 (t, J=14.5 Hz, 1H), 2.74 (ddt, J=13.0, 6.7, 3.4 Hz, 1H), 1.43 (s, 9H). $^{13}$C NMR (126 MHz, Chloroform-d): δ 172.23, 156.45, 149.34, 147.35, 138.99, 120.65, 113.89, 79.69, 40.77, 40.01, 28.53, 27.84. HRMS (ESI): m/z calc for $C_{14}H_{18}BrN_3O_3$ $[M+H]^+$: 356.0604, found: 356.0609.

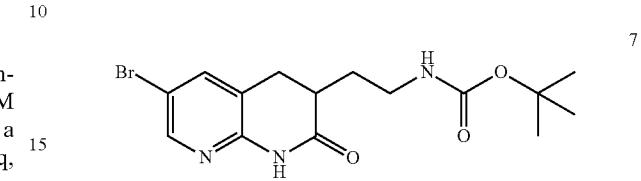

tert-butyl (2-(6-bromo-2-oxo-1,2,3,4-tetrahydro-1,8-naphthyridin-3-yl)ethyl)carbamate (7). To a solution of LHMDS (1 M in THF, 4 eq, 18 mmol) cooled to −78° C. was added a solution ethyl 4-((tert-butoxycarbonyl)amino)butanoate (S3, 2 eq, 9 mmol) in THF (18 mL) dropwise. The reaction mixture was stirred for 1.5 h followed by the portionwise addition (2 portions at 15 min intervals) of 5-bromo-3-(bromomethyl)pyridin-2-amine hydrobromide (S4, 1 eq, 4.5 mmol) via a solid addition tube kept under $N_2$. The reaction mixture was kept at −78° C. for several hours and allowed to warm to −40° C. overnight. The reaction mixture was quenched with 0.5M HCl (aq) and extracted with ethyl acetate. The combined organic extracts were dried over sodium sulfate and concentrated under reduced pressure. Purification by flash purification column chromatography (01:99 to 10:90, THF:$CH_2Cl_2$) followed by trituration with ether/n-pentane yielded tert-butyl (2-(6-bromo-2-oxo-1,2,3,4-tetrahydro-1,8-naphthyridin-3-yl)ethyl)carbamate (7, 0.740 g, 2.01 mmol, 45%) as a white solid. $^1$H NMR (500 MHz, Chloroform-d): δ 8.73 (s, 1H), 8.25 (d, J=2.2 Hz, 1H), 7.62 (d, J=2.1 Hz, 1H), 4.81 (s, 1H), 3.44-3.29 (m, 1H), 3.28-3.17 (m, 1H), 3.08 (dd, J=16.0, 6.1 Hz, 1H), 2.78 (dd, J=16.0, 9.8 Hz, 1H), 2.65 (dq, J=9.8, 6.6 Hz, 1H), 2.00 (dq, J=13.8, 6.9 Hz, 1H), 1.82-1.67 (m, 1H), 1.43 (s, 9H). $^{13}$C NMR (126 MHz, Chloroform-d): δ 172.83, 156.19, 149.31, 147.47, 138.98, 120.11, 113.80, 79.53, 38.23, 37.37, 30.33, 29.67, 28.55. HRMS (ESI): m/z calc for $C_{15}H_{20}BrN_3O_3$ $[M+H]^+$: 370.0761, found: 370.0766.

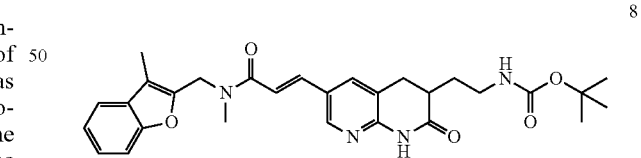

tert-butyl(E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (8). Anhydrous DMA (10 mL, sparged with $N_2$ before using) was added to a flask containing 4 (1.5 eq, 1.875 mmol), 5 (1 eq, 1.25 mmol), palladium(II) acetate (0.2 eq, 0.25 mmol), and tricyclohexylphosphine tetrafluoroborate (0.4 eq, 0.5 mmol) followed by the addition of N,N-diisopropylethylamine (2 eq, 2.5 mmol, distilled and sparged with $N_2$ before using). The reaction mixture was heated to 90-100° C. for 24 h. After reaction completion, the reaction mixture was diluted with ethyl acetate and filtered through a pad of celite and the filtrate was washed with saturated sodium bicarbonate. The combined organic extracts were dried over sodium sulfate and concentrated under reduced pressure. Purification by flash purification column chromatography (10:90 to 20:00, THF:CH$_2$Cl$_2$) followed by trituration with ether/n-pentane yielded tert-butyl (E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (8, 0.374 g, 0.762 mmol, 61%) as a white solid. Note: Tabulated NMR data for acrylamide derivatives consist of two rotamers that exist at room temperature in a ratio of 40:60 and is reflected in the reported integral values. $^1$H NMR (600 MHz, DMSO-d$_6$, 25° C.): δ 10.82 (s, 1H), 8.48-8.33 (m, 1H), 8.17-8.02 (m, 1H), 7.60-7.54 (m, 1H), 7.54-7.44 (m, 2.4H), 7.30-7.22 (m, 2H), 7.20 (d, J=15.4 Hz, 0.6H), 7.12-6.97 (m, 1H), 4.98 (s, 0.8H), 4.79 (s, 1.2H), 4.40-4.17 (m, 1H), 3.18 (s, 1.8H), 3.08-2.91 (m, 3.2H), 2.26 (s, 3H), 1.41 (s, 9H). $^1$H NMR (600 MHz, DMSO-d$_6$, 115° C.): δ 10.33 (s, 1H), 8.36 (d, J=2.1 Hz, 1H), 7.97 (s, 1H), 7.55 (d, J=7.5 Hz, 1H), 7.49 (d, J=15.4 Hz, 1H), 7.45 (d, J=8.1 Hz, 1H), 7.28 (t, J=7.6 Hz, 1H), 7.24 (t, J=7.5 Hz, 1H), 7.22-7.16 (m, 1H), 6.57 (d, J=7.8 Hz, 1H), 4.85 (s, 2H), 4.26 (dt, J=13.9, 7.2 Hz, 1H), 3.16-3.06 (m, 4H), 3.05-2.98 (m, 1H), 2.27 (s, 3H), 1.44 (s, 9H). $^{13}$C NMR (151 MHz, DMSO-d$_6$, 115° C.): δ 168.63, 165.20, 154.67, 153.13, 150.96, 148.64, 146.37, 137.28, 133.72, 128.96, 125.41, 123.61, 121.76, 118.74, 117.92, 117.39, 112.12, 110.10, 77.93, 49.08, 42.28 (brs, see HSQC) 33.72 (brs), 29.87, 27.66, 6.61. HRMS (ESI): m/z calc for C$_{27}$H$_{30}$N$_4$O$_5$ [M+H]$^+$:491.2289, found: 491.2302.

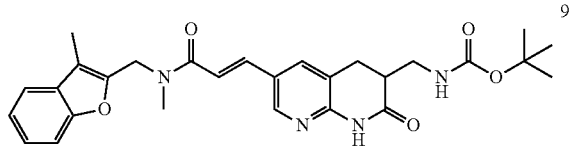 [SMILES: Cc1c(CN(C)C(=O)/C=C/c2cnc3c(c2)CC(CNC(=O)OC(C)(C)C)C(=O)N3)oc2ccccc12]

9 tert-butyl(E)-((6-(3-(methyl((3-methylbenzofuran-2-yl)methyl)amino)-3-oxoprop-1-en-1-yl)-2-oxo-1,2,3,4-tetrahydro-1,8-naphthyridin-3-yl)methyl)carbamate (9). Anhydrous DMA (32 mL, sparged with N$_2$ before using) was added to a flask containing 4 (1.5 eq, 6 mmol), 6 (1 eq, 4 mmol), palladium(II) acetate (0.2 eq, 0.8 mmol), and tricyclohexylphosphine tetrafluoroborate (0.4 eq, 1.6 mmol) followed by the addition of N,N-diisopropylethylamine (2 eq, 8 mmol, distilled and sparged with N$_2$ before using). The reaction mixture was heated to 90-100° C. for 24 h. After reaction completion, the reaction mixture was diluted with ethyl acetate and filtered through a pad of celite and the filtrate was washed with saturated sodium bicarbonate. The combined organic extracts were dried over sodium sulfate and concentrated under reduced pressure. Purification by flash purification column chromatography (10:90 to 20:00, THF:CH$_2$Cl$_2$) followed by trituration with ether/n-pentane yielded tert-butyl (E)-((6-(3-(methyl((3-methylbenzofuran-2-yl)methyl)amino)-3-oxoprop-1-en-1-yl)-2-oxo-1,2,3,4-tetrahydro-1,8-naphthyridin-3-yl)methyl)carbamate (9, 1.285 g, 2.55 mmol, 64%) as a white solid. Note: Tabulated NMR data for acrylamide derivatives consist of two rotamers that exist at room temperature in a ratio of 40:60 and is reflected in the reported integral values. $^1$H NMR (600 MHz, DMSO-d$_6$, 25° C.): δ 10.72 (s, 1H), 8.47-8.32 (m, 1H), 8.15-8.02 (m, 1H), 7.59-7.54 (m, 1H), 7.54-7.43 (m, 2.4H), 7.31-7.26 (m, 1H), 7.26-7.17 (m, 1.6H), 6.91-6.81 (m, 1H), 4.99 (s, 0.8H), 4.79 (s, 1.2H), 3.51-3.36 (m, 1H), 3.18 (s, 1.8H), 3.12-2.96 (m, 2H), 2.93 (s, 1.2H), 2.81-2.70 (m, 1H), 2.69-2.59 (m, 1H), 2.26 (s, 3H), 1.45-1.28 (m, 9H). $^1$H NMR (600 MHz, DMSO-d$_6$, 120° C.): δ 10.12 (s, 1H), 8.34 (s, 1H), 7.93 (s, 1H), 7.55 (d, J=7.4 Hz, 1H), 7.49 (d, J=15.5 Hz, 1H), 7.45 (d, J=8.1 Hz, 1H), 7.28 (td, J=8.1, 7.6, 1.5 Hz, 1H), 7.24 (td, J=7.4, 1.1 Hz, 1H), 7.19 (d, J=15.4 Hz, 1H), 6.27 (s, 1H), 4.85 (s, 2H), 3.43 (dt, J=13.6, 5.5 Hz, 1H), 3.18-3.08 (m, 4H), 3.04 (dd, J=15.9, 6.1 Hz, 1H), 2.79 (dd, J=15.8, 10.4 Hz, 1H), 2.75-2.68 (m, 1H), 2.27 (s, 3H), 1.40 (s, 9H). $^{13}$C NMR (151 MHz, DMSO-d$_6$, 120° C.): δ 170.73, 165.23, 155.00, 153.12, 151.17, 148.62, 146.07, 137.33, 133.52, 128.94, 125.39, 123.55, 121.71, 118.68, 117.74, 117.70, 112.05, 110.04, 77.38, 43.32 (brs, see HSQC), 39.58, 39.29 (solvent overlap, see HSQC), 33.69 (brs), 27.66, 26.66, 6.54. HRMS (ESI): m/z calc for C$_{28}$H$_{32}$N$_4$O$_5$ [M+H]$^+$: 505.2445, found: 505.2443.

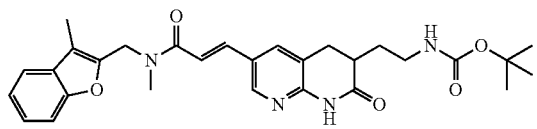

10 tert-butyl (E)-(2-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)ethyl)carbamate (10). Anhydrous DMA (10 mL, sparged with N$_2$ before using) was added to a flask containing 4 (1.5 eq, 1.875 mmol), 7 (1 eq, 1.25 mmol), palladium(II) acetate (0.2 eq, 0.25 mmol), and tricyclohexylphosphine tetrafluoroborate (0.4 eq, 0.5 mmol) followed by the addition of N,N-diisopropylethylamine (2 eq, 2.5 mmol, distilled and sparged with N$_2$ before using). The reaction mixture was heated to 90-100° C. for 24 h. After reaction completion, the reaction mixture was diluted with ethyl acetate and filtered through a pad of celite and the filtrate was washed with saturated sodium bicarbonate. The combined organic extracts were dried over sodium sulfate and concentrated under reduced pressure. Purification by flash purification column chromatography (10:90 to 20:80, THF:CH$_2$Cl$_2$) followed by trituration with ether/n-pentane yielded tert-butyl (E)-(2-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)ethyl)carbamate (10, 0.364 g, 0.702 mmol, 56%) as a white solid. Note: Tabulated NMR data for acrylamide derivatives consist of two rotamers that exist at room temperature in a ratio of 40:60 and is reflected in the reported integral values. $^1$H NMR (600 MHz, DMSO-d$_6$, 25° C.): δ 10.70 (s, 1H), 8.52-8.29 (m, 1H), 8.21-8.01 (m, 1H), 7.60-7.55 (m, 1H), 7.54-7.43 (m, 2.4H), 7.33-7.26 (m, 1H), 7.26-7.22 (m, 1H), 7.21 (d, J=16.4 Hz, 0.6H), 6.87 (t, J=5.8 Hz, 1H), 5.00 (s, 0.8H), 4.79 (s, 1.2H), 3.18 (s, 1.8H), 3.12-2.95 (m, 4H), 2.92 (s, 1.2H), 2.78-2.67 (m, 1H), 2.33-2.22 (m, 3H), 1.94-1.84 (m, 1H), 1.47-1.39 (m, 1H), 1.38-1.28 (m, 9H). $^1$H NMR (600 MHz, DMSO-d$_6$, 120° C.): δ 10.05 (s, 1H), 8.34 (s, 1H), 7.93 (s, 1H), 7.55 (d, J=7.6 Hz, 1H), 7.49 (d, J=15.5 Hz, 1H), 7.45 (d, J=8.0 Hz, 1H), 7.32-7.26 (m, 1H), 7.24 (t, J=7.3 Hz, 1H), 7.19 (d, J=15.4 Hz, 1H), 6.29 (s, 1H), 4.85 (s, 2H), 3.14-3.08 (m, 2H), 3.05 (dd, J=15.9, 6.1 Hz, 1H), 2.88 (s, 3H), 2.75 (dd, J=15.9, 10.1 Hz, 1H), 2.63-2.53 (m, 1H), 2.27 (s, 3H), 1.94 (dq, J=13.6, 7.0 Hz, 1H), 1.51 (dq, J=13.9, 6.9 Hz, 1H), 1.39 (s, 9H). $^{13}$C NMR (151 MHz, DMSO-d$_6$, 120° C.):): δ 171.96, 165.22, 154.95, 153.11, 151.32, 148.62, 146.10, 137.34, 133.32, 128.94, 125.28, 123.55, 121.71, 118.68, 117.92, 117.68, 112.05, 110.04, 77.01, 42.26, (brs, see HSQC) 37.59, 36.76, 33.66 (brs), 29.37, 28.53, 27.68, 6.54. HRMS (ESI): m/z calc for $C_{29}H_{34}N_4O_5$ [M+H]$^+$: 519.2602, found: 519.2616.

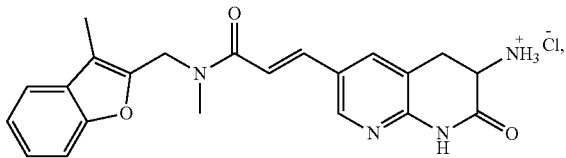

Debio-1452-NH3

(E)-3-(6-amino-7-oxo-5,6,7,8-tetrahydro-1,8-naphthyridin-3-yl)-N-methyl-N-((3-methylbenzofuran-2-yl)methyl) acrylamide hydrochloride (Debio-1452-NH3, 1). Anhydrous 4M HCl in dioxane (1 mL) was added dropwise to a solution of 8 (1 eq, 0.652 mmol) in dioxane (3 mL). The reaction mixture was stirred at room temperature. After 4 h, the reaction mixture was concentrated from $CH_2Cl_2$ several times followed by trituration with ether/n-pentane to afford (E)-3-(6-amino-7-oxo-5,6,7,8-tetrahydro-1,8-naphthyridin-3-yl)-N-methyl-N-((3-methylbenzofuran-2-yl)methyl)acrylamide hydrochloride (Debio-1452-NH3, 1, 244 mg, 0.571 mmol, 88%) as a white solid. Note: Tabulated NMR data for acrylamide derivatives consist of two rotamers that exist at room temperature in a ratio of 40:60 and is reflected in the reported integral values. $^1$H NMR (600 MHz, DMSO-$d_6$, 25° C.): δ 11.33 (s, 1H), 8.79-8.66 (m, 3H), 8.55-8.43 (m, 1H), 8.31-8.20 (m, 1H), 7.62-7.55 (m, 1H), 7.55-7.45 (m, 2.4H), 7.33-7.26 (m, 1.6H), 7.26-7.21 (m, 1H), 5.01 (s, 0.8H), 4.79 (s, 1.2H), 4.44-4.28 (m, 1H), 3.35-3.24 (m, 1H), 3.24-3.06 (m, 2.8H), 2.92 (s, 1.2H), 2.26 (s, 3H). $^1$H NMR (600 MHz, DMSO-$d_6$, 120° C.): δ 10.90 (s, 1H), 8.63 (s, 3H), 8.44 (s, 1H), 8.08 (s, 1H), 7.55 (d, J=7.9 Hz, 1H), 7.51 (d, J=15.4 Hz, 1H), 7.45 (d, J=8.2 Hz, 1H), 7.36-7.18 (m, 3H), 4.86 (s, 2H), 4.28 (dd, J=14.1, 6.9 Hz, 1H), 3.38 (dd, J=15.6, 6.7 Hz, 1H), 3.21 (t, J=14.7 Hz, 1H), 3.11 (s, 3H), 2.27 (d, J=2.3 Hz, 3H). $^{13}$C NMR (151 MHz, DMSO, 120° C.): δ 166.20, 165.14, 153.13, 150.23, 148.61, 146.69, 136.90, 134.20, 128.95, 126.14, 123.61, 121.76, 118.74, 118.63, 115.77, 112.13, 110.07, 47.37, 42.37 (brs, see HSQC), 33.54 (brs, see HSQC), 27.44, 6.59. HRMS (ESI): m/z calc for $C_{22}H_{22}N_4O_3$ [M+H]$^+$ (Note: hydrochloride salt not observed): 391.1765, found: 391.1773.

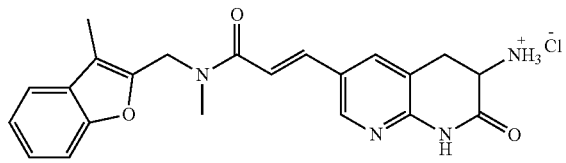

(E)-3-(6-(aminomethyl)-7-oxo-5,6,7,8-tetrahydro-1,8-naphthyridin-3-yl)-N-methyl-N-((3-methylbenzofuran-2-yl) methyl)acrylamide hydrochloride (2)—Anhydrous 4M HCl in dioxane (1 mL) was added dropwise to a solution of 9 (1 eq, 0.6 mmol) in dioxane (3 mL). The reaction mixture was stirred at room temperature. After 4 h, the reaction mixture was concentrated from $CH_2Cl_2$ several times followed by trituration with ether/n-pentane to afford (E)-3-(6-(aminomethyl)-7-oxo-5,6,7,8-tetrahydro-1,8-naphthyridin-3-yl)-N-methyl-N-((3-methylbenzofuran-2-yl)methyl)acrylamide hydrochloride (2, 256 mg, 0.581 mmol, 97%) as a white solid. Note: Tabulated NMR data for acrylamide derivatives consist of two rotamers that exist at room temperature in a ratio of 40:60 and is reflected in the reported integral values. $^1$H NMR (600 MHz, DMSO-$d_6$, 25° C.): δ 11.03 (s, 1H), 8.49-8.40 (m, 1H), 8.21-8.04 (m, 4H), 7.59-7.55 (m, 1H), 7.55-7.46 (m, 2.4H), 7.31-7.21 (m, 2.6H), 5.01 (s, 0.8H), 4.79 (s, 1.2H), 3.29-3.21 (m, 1H), 3.19 (s, 1.8H), 3.08-2.97 (m, 3H), 2.95-2.85 (m, 2.2H), 2.32-2.19 (m, 3H). $^1$H NMR (600 MHz, DMSO-$d_6$, 120° C.): δ 10.49 (s, 1H), 8.40 (d, J=2.2 Hz, 1H), 8.15 (s, 3H), 7.96 (s, 1H), 7.55 (d, J=7.6 Hz, 1H), 7.50 (d, J=15.5 Hz, 1H), 7.45 (d, J=8.0 Hz, 1H), 7.28 (td, J=8.1, 7.7, 1.5 Hz, 1H), 7.26-7.12 (m, 2H), 4.85 (s, 2H), 3.31-3.27 (m, 1H), 3.14-3.02 (m, 6H), 2.96-2.90 (m, 1H), 2.27 (s, 3H). $^{13}$C NMR (151 MHz, DMSO-$d_6$, 120° C.): δ 170.24, 165.20, 153.12, 150.80, 148.63, 146.25, 137.15, 133.57, 128.94, 125.74, 123.59, 121.74, 118.72, 118.20, 117.47, 112.10, 110.06, 42.40 (brs, see HSQC), 38.34, 36.80, 33.73 (brs), 26.66, 6.58. HRMS (ESI): m/z calc for $C_{23}H_{24}N_4O_3$ [M+H]$^+$ (Note: hydrochloride salt not observed): 405.1921, found: 405.1927.

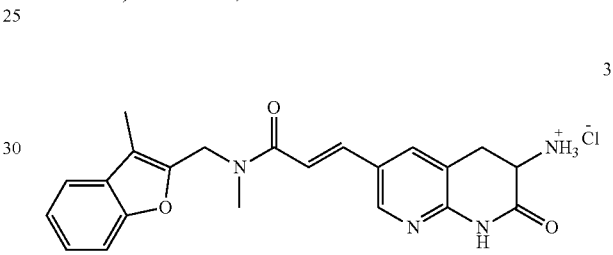

(E)-3-(6-(aminoethyl)-7-oxo-5,6,7,N-tetrahydro-1,N-naphthyridin-3-yl)-N-methyl-N-((3-methylbenzofuran-2-yl) methyl)acrylamide hydrochloride (3). Anhydrous 4M HCl in dioxane (1 mL) was added dropwise to a solution of 10 (1 eq, 0.6 mmol) in dioxane (3 mL). The reaction mixture was stirred at room temperature. After 4 h, the reaction mixture was concentrated from $CH_2Cl_2$ several times followed by trituration with ether/pentane to afford (E)-3-(6-(aminoethyl)-7-oxo-5,6,7,8-tetrahydro-1,8-naphthyridin-3-yl)-N-methyl-N-((3-methylbenzofuran-2-yl)methyl)acrylamide hydrochloride (3, 244 mg, 0.536 mmol, 89%) as a white solid. Note: Tabulated NMR data for acrylamide derivatives consist of two rotamers that exist at room temperature in a ratio of 40:60 and is reflected in the reported integral values. $^1$H NMR (600 MHz, DMSO-$d_6$, 25° C.): δ 10.80 (s, 1H), 8.47-8.37 (m, 1H), 8.17-8.09 (m, 1H), 8.06-7.95 (m, 3H), 7.60-7.54 (m, 1H), 7.54-7.43 (m, 2.4H), 7.30-7.26 (m, 1H), 7.26-7.17 (m, 1.6H), 4.99 (s, 0.8H), 4.79 (s, 1.2H), 3.18 (s, 1.8H), 3.03-2.97 (m, 1H), 2.96-2.89 (m, 3.2H), 2.80-2.67 (m, 2H), 2.30-2.22 (m, 3H), 2.10-2.00 (m, 1H), 1.71-1.63 (m, 1H). $^1$H NMR (600 MHz, DMSO-$d_6$, 115° C.): δ 10.27 (s, 1H), 8.38 (s, 1H), 7.96 (s, 1H), 7.83 (s, 3H), 7.55 (d, J=7.6 Hz, 1H), 7.50 (d, J=15.4 Hz, 1H), 7.45 (d, J=8.1 Hz, 1H), 7.28 (t, J=7.7 Hz, 1H), 7.24 (t, J=7.4 Hz, 1H), 7.20 (d, J=15.4 Hz, 1H), 4.85 (s, 2H), 3.11 (s, 3H), 3.05 (dd, J=15.4, 5.7 Hz, 1H), 3.03-2.89 (m, 2H), 2.79 (dd, J=15.4, 11.3 Hz, 1H), 2.76-2.69 (m, 1H), 2.27 (s, 3H), 2.10 (dq, J=14.4, 7.4 Hz, 1H), 1.77 (dq, J=13.8, 7.0 Hz, 1H). $^{13}$C NMR (151 MHz, DMSO-$d_6$, 115° C.): δ 171.63, 165.22, 153.13, 151.19, 148.64, 146.21, 137.35, 133.50, 128.96, 125.46, 123.63, 121.78, 118.76, 117.92, 117.85, 112.13, 110.09, 42.25 (brs, see HSQC), 36.76, 36.57, 33.71 (brs), 28.73, 27.07, 6.62.

HRMS (ESI): m/z calc for $C_{24}H_{26}N_4O_3$ [M+H]$^+$ (Note: hydrochloride salt not observed): 419.2078, found: 419.2071.

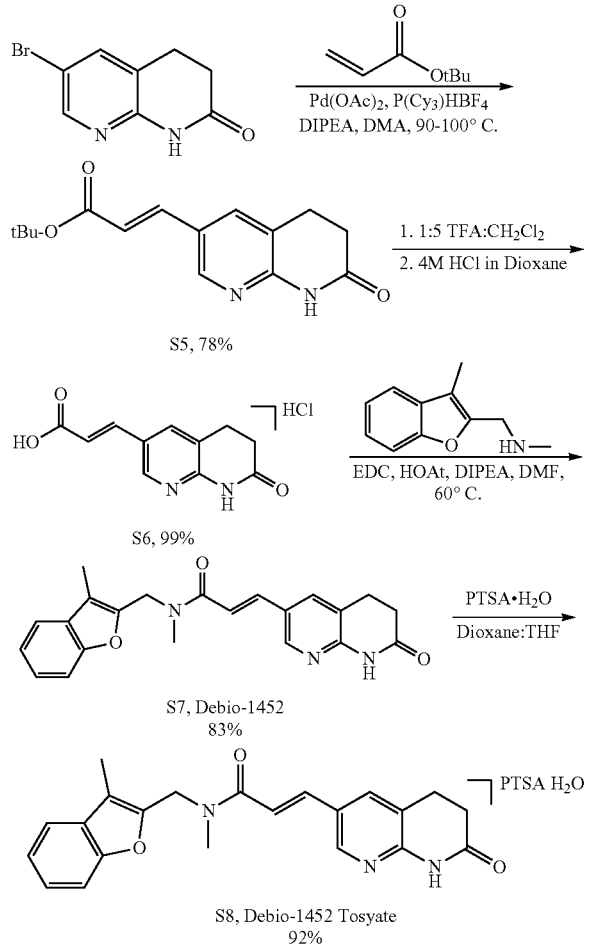

Scheme C. Synthesis of Debio-1452 Tosylate.

Cy, cyclohexyl; DIPEA, N,N-diisopropyl ethylamine; TFA, trifluoroacetic acid; EDC, 1-ethyl-3-(3-dimethylaminopropyl)carbodiimide; HOAt, 1-hydroxy-7-azabenzotriazole; DMF, N,N-Dimethylformamide; PTSA, p-toluene sulfonic acid; THF, tetrahydrofuran.

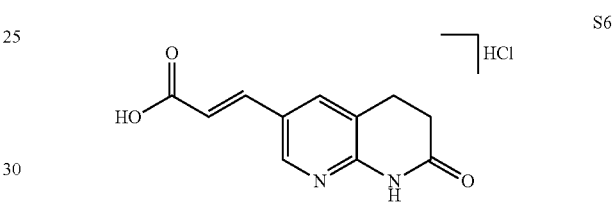

tert-butyl (E)-3-(7-oxo-5,6,7,8-tetrahydro-1,8-naphthyridin-3-yl)acrylate (S5)

Anhydrous DMA (32 mL, sparged with $N_2$ before using) was added to a flask containing 6-bromo-3,4-dihydro-1,8-naphthyridin-2(1H)-one (1 eq, 10 mmol), palladium(II) acetate (0.05 eq, 0.5 mmol), and tricyclohexylphosphine tetrafluoroborate (0.1 eq, 1.0 mmol) followed by the addition of tert-butyl acrylate (1.5 eq, 15 mmol, sparged with $N_2$ before using), N,N-diisopropylethylamine (2 eq, 20 mmol, distilled and sparged with $N_2$ before using). The reaction mixture was heated to 90-100° C. for 24 h. After reaction completion, the reaction mixture was diluted with ethyl acetate and filtered through a pad of celite and the filtrate was washed with saturated sodium bicarbonate. The combined organic extracts were dried over sodium sulfate and concentrated under reduced pressure. Purification by flash purification column chromatography (10:90 to 30:70, EtOAc:$CH_2Cl_2$) followed by trituration with ether/n-pentane yielded tert-butyl (E)-3-(7-oxo-5,6,7,8-tetrahydro-1,8-naphthyridin-3-yl)acrylate (S5, 2.151 g, 7.85 mmol, 78%) as a white solid. $^1$H NMR (500 MHz, Chloroform-d): δ 8.94 (s, 1H), 8.32 (d, J=2.1 Hz, 1H), 7.65 (d, J=1.5 Hz, 1H), 7.51 (d, J=16.0 Hz, 1H), 6.33 (d, J=16.0 Hz, 1H), 2.99 (t, J=7.6 Hz, 2H), 2.71 (dd, J=8.4, 6.8 Hz, 2H), 1.53 (s, 9H). $^{13}$C NMR (126 MHz, Chloroform-d): 170.97, 165.97, 151.95, 147.37, 139.43, 134.05, 126.16, 120.57, 118.84, 80.99, 77.36, 30.40, 28.34, 24.22.

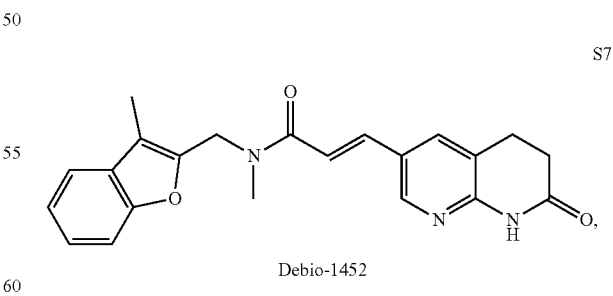

(E)-3-(7-oxo-5,6,7,8-tetrahydro-1,8-naphthyridin-3-yl)acrylic acid hydrochloride (S6). (E)-3-(7-oxo-5,6,7,8-tetrahydro-1,8-naphthyridin-3-yl)acrylate (S5) was dissolved trifluoroacetic acid:$CH_2Cl_2$ (8 mL:40 mL) and stirred at room temperature. After 2 h, the reaction mixture was concentrated several times from $CH_2Cl_2$. The crude material was suspended in 4 M HCl in dioxane (20 mL), stirred for 30 min, filtered, and rinsed with ether to afford (E)-3-(7-oxo-5,6,7,8-tetrahydro-1,8-naphthyridin-3-yl)acrylic acid HCl (S6, 7.67 mmol, 99%) as a white solid. $^1$H NMR (500 MHz, DMSO-$d_6$): δ 10.68 (s, 1H), 8.35 (d, J=2.2 Hz, 1H), 8.02 (d, J=2.1 Hz, 1H), 7.54 (d, J=16.0 Hz, 1H), 6.51 (d, J=16.0 Hz, 1H), 2.91 (t, J=7.6 Hz, 2H), 2.53 (dd, J=8.5, 6.8 Hz, 2H). $^{13}$C NMR (126 MHz, DMSO): δ 171.01, 167.47, 152.77, 147.33, 140.62, 133.78, 124.72, 119.20, 118.34, 29.97, 23.27.

(E)-N-methyl-N-((3-methylbenzofuran-2-yl)methyl)-3-(7-oxo-5,6,7,8-tetrahydro-1,8-naphthyridin-3-yl)acrylamide (S7, Debio-1452)—To a solution of N-methyl-1-(3-methylbenzofuran-2-yl)methanamine (1.1 eq, 6.93 mmol), (E)-3-(7-oxo-5,6,7,8-tetrahydro-1,8-naphthyridin-3-yl)acrylic acid hydrochloride (1 eq, 6.3 mmol), 1-hydroxy-7-azabenzotriazole (1.1 eq, 6.93 mmol), in N,N-Dimethylformamide (32 mL) was added N,N-diisopropylethylamine (2.2 eq, 13.86 mmol) followed by 1-ethyl-3-(3-dimethylaminopropyl)carbodiimide (1.1 eq, 6.93 mmol). The reaction mixture was heated to 60° C. for 6 h. The crude reaction mixture was diluted with water, filtered, rinsed with water, rinsed with ether, and dried to afford (E)-N-methyl-N-((3-methylbenzofuran-2-yl)methyl)-3-(7-oxo-5,6,7,8-tetrahydro-1,8-naphthyridin-3-yl)acrylamide (S7, Debio-1452, 1.970 g, 5.25 mmol, 83%) as a light beige solid. Note: Tabulated NMR data for acrylamide derivatives consist of two rotamers that exist at room temperature in a ratio of 40:60 and is reflected in the reported integral value. $^1$H NMR (500 MHz, DMSO-$d_6$): δ 10.65 (s, 1H), 8.41-8.34 (m, 1H), 8.18-8.00 (m, 1H), 7.59-7.54 (m, 1H), 7.54-7.45 (m, 2.4H), 7.31-7.26 (m, 1H), 7.26-7.22 (m, 1H), 7.22-7.16 (m, 0.6H), 4.99 (s, 0.8H), 4.79 (s, 1.2H), 3.18 (s, 1.8H), 2.92 (s, 1.2H), 2.92-2.87 (m, 2H), 2.57-2.51 (m, 2H), 2.26 (s, 3H).

S8

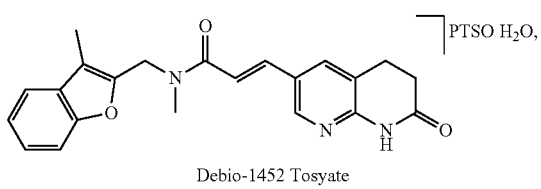

Debio-1452 Tosyate (E)-N-methyl-N-((3-methylbenzofuran-2-yl)methyl)-3-(7-oxo-5,6,7,8-tetrahydro-1,8-naphthyridin-3-yl)acrylamide p-toluenesulfonic acid monohydride (S8, Debio-1452 Tosylate)-S7, Debio-1452 (1 eq, 1.5 mmol) was suspended in THF (120 mL) and heated to reflux. After 30 min, p-toluene sulfonic acid monohydrate (1.05 eq, 1.58 mmol) in dioxane (12 mL) was added to the reaction mixture and stirred for 1 h. The reaction mixture was allowed to cool to room temperature and diluted with a mixture of 1:1 ether:n-pentane (80 mL), filtered, rinsed with 1:1 ether:n-pentane, and dried to afford (E)-N-methyl-N-((3-methylbenzofuran-2-yl)methyl)-3-(7-oxo-5,6,7,8-tetrahydro-1,8-naphthyridin-3-yl)acrylamide p-toluenesulfonic acid (S8, Debio-1452 Tosylate, 0.756 g, 1.38 mmol, 92%) as a white solid. The product was further processed for in vivo efficacy studies to improve solubility. For these studies, Debio-1452 Tosylate was ground in a mortar and pestle and then sieved through a 75 μM mesh. Note: Tabulated NMR data for acrylamide derivatives consist of two rotamers that exist at room temperature in a ratio of 40:60 and is reflected in the reported integral values. $^1$H NMR (500 MHz, DMSO-$d_6$): δ 10.69 (s, 1H), 9.49 (brs, 1H), 8.42-8.32 (m, 1H), 8.17-8.05 (m, 1H), 7.59-7.54 (m, 1H), 7.54-7.43 (m, 4.4H), 7.31-7.22 (m, 2H), 7.21 (d, J=12.6 Hz, 0.6H), 7.15-7.09 (m, 2H), 4.99 (s, 0.8H), 4.79 (s, 1.2H), 3.18 (s, 1.8H), 2.96-2.89 (m, 3.2H), 2.57-2.51 (m, 2H), 2.29 (s, 3H), 2.26 (s, 3H).

Example 1-2: Preparation of Naphthyridinone Analogs

General Synthetic Procedures. Note: Tabulated NMR data for acrylamide derivatives consist of two rotamers that exist at room temperature. Final compounds were dried in an Abderhalden drying pistol to remove any residual solvents.

Scheme 1. Synthesis of Napthyridinone Analogs E1-E17 (see Table 5 in Example 4)

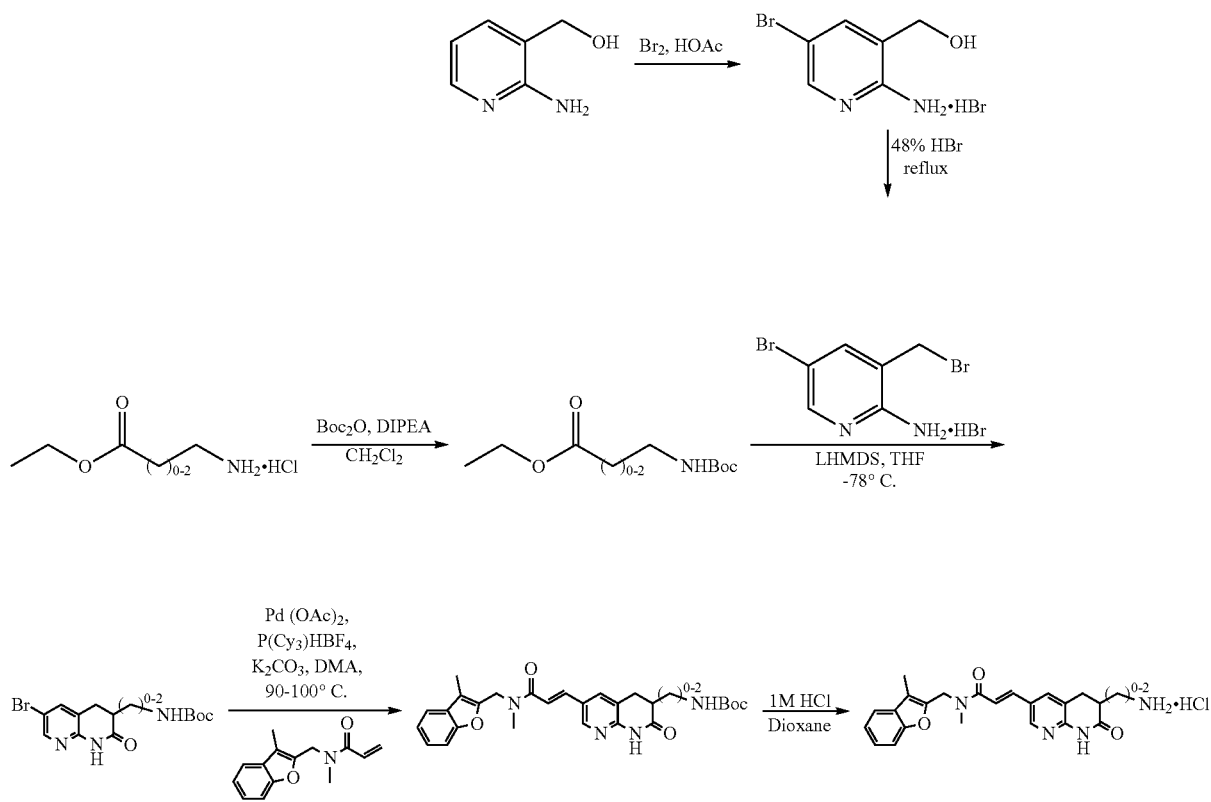

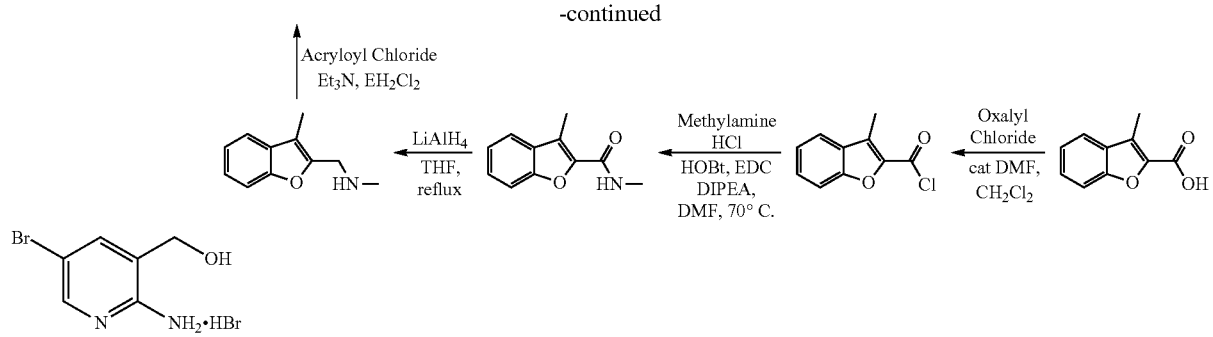

(2-Amino-5-bromopyridin-3-yl)methanol hydrobromide (E-1)

Bromine (1.01 eq, 39.02 mmol) was added dropwise to a solution of 2-amino-3-(hydroxymethyl)pyridine (1 eq, 38.6 mmol) in glacial acetic acid (60 mL) cooled in an ice bath. After the addition of bromine was compete, the reaction mixture was returned to room temperature. After stirring overnight, the reaction mixture was filtered and washed several times with ether to yield (2-amino-5-bromopyridin-3-yl)methanol hydrobromide (10.012 g, 35.5 mmol, 92% yield) as a yellow solid. (HBr Salt)$^1$H NMR (500 MHz, DMSO-d$_6$) δ 8.17 (d, J=2.3 Hz, 1H), 8.01-7.90 (m, 1H), 4.41 (s, 2H). $^{13}$C NMR (126 MHz, DMSO) δ 151.39, 141.11, 135.60, 127.72, 104.27, 57.98. (Free Base)$^1$H NMR (500 MHz, DMSO-d$_6$) δ 7.89 (d, J=2.5 Hz, 1H), 7.52 (dd, J=2.3, 1.1 Hz, 1H), 5.91 (s, 2H), 5.27 (t, J=5.5 Hz, 1H), 4.30 (d, J=5.6 Hz, 2H). $^{13}$C NMR (126 MHz, DMSO) δ 155.75, 145.84, 135.86, 122.65, 105.50, 59.00.

5-Bromo-3-(bromomethyl)pyridin-2-amine hydrobromide (E-2)

A suspension of (2-amino-5-bromopyridin-3-yl)methanol hydrobromide (1 eq, 35.47 mmol) in 48% hydrobromic acid (70 mL) was refluxed for 10 h. After 10 h, the reaction mixture was allowed to slowly cool to room, filtered, and rinsed with ethyl acetate. The solid was triturated with ethyl acetate to yield 5-bromo-3-(bromomethyl)pyridin-2-amine hydrobromide (10.226 g, 29.7 mmol, 84%) as a beige solid. $^1$H NMR (500 MHz, DMSO-d$_6$) δ 8.18 (d, J=2.4 Hz, 1H), 8.15 (d, J=2.4 Hz, 1H), 4.72 (s, 2H). $^{13}$C NMR (126 MHz, DMSO) δ 153.04, 144.29, 141.01, 121.66, 104.11, 29.13.

N, 3-Dimethylbenzofuran-2-carboxamide (E-3)

To a solution of 3-methylbenzo[b]furan-2-carboxylic acid (1 eq, 52 mmol), methylamine hydrochloride (1.1 eq, 57.52 mmol), DIPEA (2.2 eq, 114.4 mmol), and HOBt (1.1 eq, 57.52 mmol) in DMF (150 mL) was added EDC (1.1 eq, 57.52 mmol). The reaction mixture was heated to 70° C. overnight. The solvent was reduced to a few mL. The crude reaction mixture was diluted with CH$_2$Cl$_2$ and washed with saturated aqueous sodium bicarbonate. The organic extracts were dried over sodium sulfate and concentrated under reduced pressure. Purification by flash column chromatography (20:50:30, EtOAc:CH$_2$Cl$_2$:hexanes) yielded N,3-dimethylbenzofuran-2-carboxamide (9.24 g, 48.9 mmol, 94%) as a white solid. $^1$H NMR (500 MHz, Chloroform-d) δ 7.63-7.59 (m, 1H), 7.45-7.38 (m, 2H), 7.29 (ddd, J=8.0, 6.4, 1.7 Hz, 1H), 6.64 (s, 1H), 3.05-3.00 (m, 3H), 2.63 (s, 3H). $^{13}$C NMR (126 MHz, CDCl$_3$) δ 161.10, 153.35, 142.96, 129.95, 127.04, 123.19, 122.19, 121.07, 111.55, 25.86, 9.00.

N-Methyl-1-(3-methylbenzofuran-2-yl)methanamine (E-4)

Lithium aluminum hydride (3 eq, 47.6 mmol) was added portionwise to a solution of N,3-dimethylbenzofuran-2-carboxamide (1 eq, 15.86 mmol) in THF (75 mL) at room temperature. The reaction mixture was refluxed for 11 h. After reaction completion, the reaction mixture was cooled to 0° C. and slowly quenched by the sequential addition of 2 mL water, 2 mL 15% sodium hydroxide, 6 mL water at 15-30 min intervals. The mixture was filtered through a pad of celite rinsed several times with ethyl acetate. Purification by flash column chromatography (5:95, MeOH:CH$_2$Cl$_2$) yielded N-methyl-1-(3-methylbenzofuran-2-yl)methanamine (2.513 g, 14.3 mmol, 91%). $^1$H NMR (500 MHz, Chloroform-d) δ 7.48-7.45 (m, 1H), 7.43-7.39 (m, 1H), 7.27-7.23 (m, 1H), 7.21 (td, J=7.4, 1.3 Hz, 1H), 3.87 (s, 2H), 2.45 (s, 3H), 2.23 (s, 3H). $^{13}$C NMR (126 MHz, CDCl$_3$) δ 154.25, 151.41, 130.09, 124.00, 122.26, 119.28, 112.30, 111.04, 46.25, 35.83, 8.08.

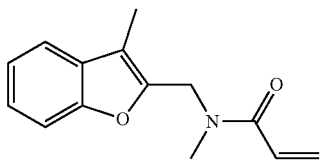 [SMILES: C=CC(=O)N(C)Cc1oc2ccccc2c1C]

N-methyl-N-((3-methylbenzofuran-2-yl)methyl)acrylamide (E-5)

DIPEA (1.5 eq, 4.8 mmol) was added dropwise to a solution of N-methyl-1-(3-methylbenzofuran-2-yl)methanamine (1 eq, 3.2 mmol) in CH$_2$Cl$_2$ (75 mL) at room temperature. After 10 min, acryloyl chloride (2 eq, 6.4 mmol) was added dropwise and the reaction mixture was stirred overnight. The solvent was removed under reduced pressure and purification by flash column chromatography (1:99, MeOH:CH$_2$Cl$_2$) yielded N-methyl-N-((3-methylbenzofuran-2-yl)methyl)acrylamide (0.638 g, 2.78 mmol, 87%) as a colorless oil. $^1$H NMR (500 MHz, Chloroform-d) δ 7.52-7.45 (m, 1H), 7.43-7.37 (m, 1H), 7.34-7.18 (m, 1H), 6.85 (dd, J=16.9, 10.6 Hz, 0.3H), 6.60 (dd, J=16.8, 10.4 Hz, 0.7H), 6.43-6.34 (m, 1H), 5.81-5.67 (m, 1H), 4.78 (s, 1.3H), 4.64 (s, 0.7H), 3.14 (s, 2H), 3.03 (s, 1H), 2.33-2.24 (m, 3H).

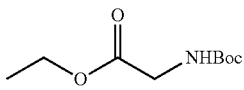

Ethyl (tert-butoxycarbonyl)glycinate (E-6)

DIPEA (2.2 eq, 44 mmol) was added dropwise to a solution of glycine ethyl ester hydrochloride (1 eq, 20 mmol) in CH$_2$Cl$_2$ (80 mL) at 0° C. followed by the dropwise addition of di-tert-butyl dicarbonate (1.1 eq, 22 mmol). The reaction mixture was allowed to warm to room temperature and stirred for 1.5 h. The reaction was quenched with saturated aqueous ammonium chloride and extracted with dichloromethane. The combined organic extracts were washed with saturated aqueous sodium bicarbonate, dried over sodium sulfate, and concentrated under reduced pressure. Purification by flash purification column chromatography (10:40:50, EtOAc:CH$_2$Cl$_2$:Hexanes) yielded ethyl (tert-butoxycarbonyl)glycinate (3.58 g, 17.6 mmol, 88%) as a colorless oil. 1H NMR (500 MHz, Chloroform-d) δ 4.99 (s, 1H), 4.21 (q, J=7.1 Hz, 2H), 3.90 (d, J=5.6 Hz, 2H), 1.45 (s, 10H), 1.28 (t, J=7.2 Hz, 3H). 13C NMR (126 MHz, CDCl$_3$) δ 170.48, 155.82, 80.10, 61.48, 42.62, 28.47, 14.31.

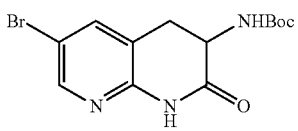 [SMILES: CC(C)(C)OC(=O)NC1Cc2cc(Br)cnc2NC1=O]

Tert-butyl (6-bromo-2-oxo-1,2,3,4-tetrahydro-1,8-naphthyridin-3-yl)carbamate (E-7)

To a solution of LHMDS (1 M in THF, 4 eq, 12 mmol) cooled to −78° C. was added a solution of ethyl (tert-butoxycarbonyl)glycinate (2 eq, 6 mmol) in THF (12 mL) dropwise. The reaction mixture was stirred for 1 h followed by the portionwise addition of 5-bromo-3-(bromomethyl)pyridin-2-amine hydrobromide (1 eq, 3 mmol) via a solid addition tube kept under N$_2$. The reaction mixture was warmed to −40° C. after a few hours. After an additional 4 h, the reaction mixture was allowed to warm to room temperature overnight. The reaction mixture was quenched with water and extracted with ethyl acetate. The combined organic extracts were dried over sodium sulfate and concentrated under reduced pressure. Purification by flash purification column chromatography (01:99 to 10:90, THF:CH$_2$Cl$_2$) followed by trituration with ether/n-heptane yielded tert-butyl (6-bromo-2-oxo-1,2,3,4-tetrahydro-1,8-naphthyridin-3-yl)carbamate (0.343 g, 1.0 mmol, 33%) as a white solid. $^1$H NMR (500 MHz, Chloroform-d) δ 8.75 (s, 1H), 8.32-8.24 (m, 1H), 7.65 (s, 1H), 5.59 (s, 1H), 4.45-4.27 (m, 1H), 3.53 (dd, J=16.3, 6.1 Hz, 1H), 2.83 (t, J=14.9 Hz, 1H), 1.48 (s, 9H).

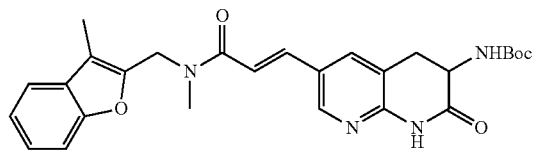 [SMILES: Cc1c(CN(C)C(=O)/C=C/c2cnc3c(c2)CC(NC(=O)OC(C)(C)C)C(=O)N3)oc2ccccc12]

Tert-butyl(E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (E-8)

Anhydrous DMA (4 mL, sparged with N$_2$ before using) was added to a flask containing N-methyl-N-((3-methylbenzofuran-2-yl)methyl)acrylamide (1.1 eq, 1.1 mmol), tert-butyl (6-bromo-2-oxo-1,2,3,4-tetrahydro-1,8-naphthyridin-3-yl)carbamate (1 eq, 1 mmol), palladium(II) acetate (0.2 eq, 0.2 mmol), tricyclohexylphosphine tetrafluoroborate (0.4 eq, 0.4 mmol), and potassium carbonate (2 eq, 2 mmol). The reaction mixture was heated to 90-100° C. for 12 h. After reaction completion, the reaction mixture was diluted with dichloromethane and filtered through a pad of celite and the filtrate was washed with water. The combined organic extracts were dried over sodium sulfate and concentrated under reduced pressure. Purification by flash purification column chromatography (10:90 to 20:00, THF:CH$_2$Cl$_2$) followed by trituration with ether/n-heptane yielded tert-butyl (E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (0.147 g, 0.30 mmol, 30%) as a white solid. $^1$H NMR (500 MHz, Chloroform-d) δ 8.66 (s, 1H), 8.43-8.29 (m, 1H), 7.77-7.61 (m, 2H), 7.53-7.46 (m, 1H), 7.45-7.38 (m, 1H), 7.33-7.20 (m, 2H), 7.15 (d, J=15.5 Hz, 0.3H), 6.86 (d, J=15.4 Hz, 0.7H), 5.61 (s, 1H), 4.84 (s, 1.4H), 4.72 (s, 0.6H), 4.48-4.29 (m, 1H), 3.66-3.51 (m, 1H), 3.24 (s, 2.1H), 3.09 (s, 0.9H), 3.01-2.76 (m, 1H), 2.31 (s, 3H), 1.56 (s, 3H), 1.48 (s, 9H).

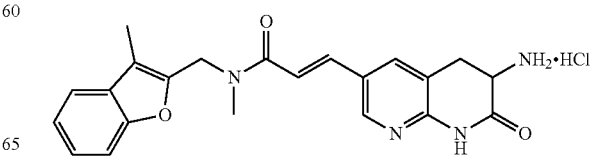

(E)-3-(6-amino-7-oxo-5,6,7,8-tetrahydro-1,8-naphthyridin-3-yl)-N-methyl-N-((3-methylbenzofuran-2-yl)methyl)acrylamide hydrochloride (E-9)

Anhydrous 4M HCl in dioxane (0.5 mL) was added dropwise to a solution of tert-butyl (E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (1 eq, 0.285 mmol) in dioxane (1.5 mL). The reaction mixture was stirred at room temperature. After 4 h, the reaction mixture was concentrated from CH$_2$Cl$_2$ several times followed by trituration with ether/pentane to afford (E)-3-(6-amino-7-oxo-5,6,7,8-tetrahydro-1,8-naphthyridin-3-yl)-N-methyl-N-((3-methylbenzofuran-2-yl)methyl)acrylamide hydrochloride (110 mg, 0.26 mmol, 91%) as a white solid. $^1$H NMR (500 MHz, DMSO-d$_6$) δ 11.09 (s, 1H), 8.52-8.40 (m, 1H), 8.23-8.14 (m, 1H), 7.60-7.44 (m, 3.4H), 7.33-7.19 (m, 3.6H), 6.53 (s, 2H), 5.00 (s, 0.8H), 4.79 (s, 1.2H), 4.12-3.91 (m, 1H), 3.23-3.10 (m, 2.8H), 3.02-2.88 (m, 2.2H), 2.27 (s, 3H).

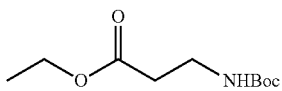

Ethyl 3-((tert-butoxycarbonyl)amino)propanoate (E-10)

DIPEA (2.2 eq, 44 mmol) was added dropwise to a solution of β-alanine ethyl ester hydrochloride (1 eq, 20 mmol) in CH$_2$Cl$_2$ (80 mL) at 0° C. followed by the dropwise addition of di-tert-butyl dicarbonate (1.1 eq, 22 mmol). The reaction mixture was allowed to warm to room temperature and stirred for 1.5 h. The reaction was quenched with saturated aqueous ammonium chloride and extracted with dichloromethane. The combined organic extracts were washed with saturated aqueous sodium bicarbonate, dried over sodium sulfate, and concentrated under reduced pressure. Purification by flash purification column chromatography (10:40:50, EtOAc:CH$_2$Cl$_2$:Hexanes) yielded ethyl 3-((tert-butoxycarbonyl)amino)propanoate (3.25 g, 15.0 mmol, 75%) as a colorless oil. $^1$H NMR (500 MHz, Chloroform-d) δ 5.01 (s, 1H), 4.15 (q, J=7.1 Hz, 2H), 3.39 (q, J=6.1 Hz, 2H), 2.51 (t, J=6.1 Hz, 2H), 1.43 (s, 9H), 1.27 (t, J=7.2 Hz, 3H). $^{13}$C NMR (126 MHz, CDCl$_3$) δ 172.66, 155.91, 79.49, 60.79, 36.25, 34.80, 28.54, 14.35.

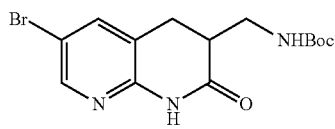 [SMILES: CC(C)(C)OC(=O)NCC1Cc2cc(Br)cnc2NC1=O]

Tert-butyl ((6-bromo-2-oxo-1,2,3,4-tetrahydro-1,8-naphthyridin-3-yl)methyl)carbamate (E-11)

To a solution of LHMDS (1 M in THF, 4 eq, 12 mmol) cooled to −78° C. was added a solution ethyl 3-((tert-butoxycarbonyl)amino)propanoate (2 eq, 6 mmol) in THF (12 mL) dropwise. The reaction mixture was stirred for 1 h followed by the portionwise addition of 5-bromo-3-(bromomethyl)pyridin-2-amine hydrobromide (1 eq, 3 mmol) via a solid addition tube kept under N$_2$. The reaction mixture was warmed to −40° C. after a few hours. After an additional 4 h, the reaction mixture was allowed to warm to room temperature overnight. The reaction mixture was quenched with water and extracted with ethyl acetate. The combined organic extracts were dried over sodium sulfate and concentrated under reduced pressure. Purification by flash purification column chromatography (01:99 to 10:90, THF:CH$_2$Cl$_2$) followed by trituration with ether/n-heptane yielded tert-butyl ((6-bromo-2-oxo-1,2,3,4-tetrahydro-1,8-naphthyridin-3-yl)methyl)carbamate (0.345 g, 0.95 mmol, 32%) as a white solid. $^1$H NMR (500 MHz, Chloroform-d) δ 8.76 (s, 1H), 8.25 (d, J=2.0 Hz, 1H), 7.63 (s, 1H), 5.27 (t, J=6.7 Hz, 1H), 3.62 (ddd, J=14.1, 6.6, 3.8 Hz, 1H), 3.48 (dt, J=14.1, 6.2 Hz, 1H), 2.95 (dd, J=16.1, 6.9 Hz, 1H), 2.92-2.84 (m, 1H), 2.82-2.66 (m, 1H), 1.43 (s, 9H). $^{13}$C NMR (126 MHz, CDCl$_3$) δ 172.23, 156.46, 149.31, 147.35, 138.99, 120.65, 113.90, 79.70, 40.76, 39.99, 28.52, 27.82.

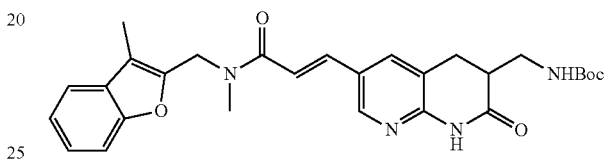

Tert-butyl(E)-((6-(3-(methyl((3-methylbenzofuran-2-yl)methyl)amino)-3-oxoprop-1-en-1-yl)-2-oxo-1,2,3,4-tetrahydro-1,8-naphthyridin-3-yl)methyl)carbamate (E-12)

Anhydrous DMA (4 mL, sparged with N$_2$ before using) was added to a flask containing N-methyl-N-((3-methylbenzofuran-2-yl)methyl)acrylamide (1.1 eq, 0.924 mmol), tert-butyl ((6-bromo-2-oxo-1,2,3,4-tetrahydro-1,8-naphthyridin-3-yl)methyl)carbamate (1 eq, 0.84 mmol), palladium(II) acetate (0.2 eq, 0.168 mmol), tricyclohexylphosphine tetrafluoroborate (0.4 eq, 0.336 mmol), and potassium carbonate (2 eq, 1.68 mmol). The reaction mixture was heated to 90-100° C. for 12 h. After reaction completion, the reaction mixture was diluted with dichloromethane and filtered through a pad of celite and the filtrate was washed with water. The combined organic extracts were dried over sodium sulfate and concentrated under reduced pressure. Purification by flash purification column chromatography (10:90 to 20:00, THF:CH$_2$Cl$_2$) followed by trituration with ether/n-heptane yielded tert-butyl (E)-((6-(3-(methyl((3-methylbenzofuran-2-yl)methyl)amino)-3-oxoprop-1-en-1-yl)-2-oxo-1,2,3,4-tetrahydro-1,8-naphthyridin-3-yl)methyl)carbamate (0.112 g, 0.22 mmol, 26%) as a white solid. $^1$H NMR (500 MHz, Chloroform-d) δ 8.51 (s, 1H), 8.38-8.25 (m, 1H), 7.74-7.60 (m, 2H), 7.55-7.46 (m, 1H), 7.44-7.36 (m, 1H), 7.32-7.20 (m, 2H), 7.13 (d, J=15.5 Hz, 0.3H), 6.86 (d, J=15.4 Hz, 0.7H), 5.27 (s, 1H), 4.84 (s, 1.4H), 4.72 (s, 0.6H), 3.72-3.56 (m, 1H), 3.56-3.42 (m, 1H), 3.24 (s, 2.1H), 3.10 (s, 0.9H), 3.06-2.96 (m, 1H), 2.96-2.85 (m, 1H), 2.84-2.71 (m, 1H), 2.31 (d, J=6.2 Hz, 3H), 1.56 (s, 3H), 1.42 (s, 9H).

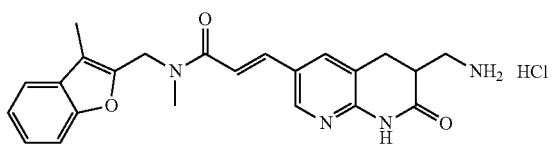 [SMILES: Cc1c(CN(C)C(=O)/C=C/c2cnc3c(c2)CC(CN)C(=O)N3)oc2ccccc12 ; Cl]

(E)-3-(6-(aminomethyl)-7-oxo-5,6,7,8-tetrahydro-1,8-naphthyridin-3-yl)-1V-methyl-N-((3-methylbenzofuran-2-yl)methyl)acrylamide hydrochloride (E-13)

Anhydrous 4M HCl in dioxane (0.5 mL) was added dropwise to a solution of tert-butyl (E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (1 eq, 0.20 mmol) in dioxane (1.5 mL). The reaction mixture was stirred at room temperature. After 4 h, the reaction mixture was concentrated from CH$_2$Cl$_2$ several times followed by trituration with ether/pentane to afford (E)-3-(6-(aminomethyl)-7-oxo-5,6,7,8-tetrahydro-1,8-naphthyridin-3-yl)-N-methyl-N-((3-methylbenzofuran-2-yl)methyl)acrylamide hydrochloride (82 mg, 0.19 mmol, 92%) as a white solid. $^1$H NMR (500 MHz, DMSO-d$_6$) δ 11.02 (s, 1H), 8.55-8.36 (m, 1H), 8.09 (m, 1H), 7.96 (s, 3H), 7.59-7.55 (m, 1H), 7.54 (m, 2.4H), 7.26 (m, 2.6H), 5.00 (s, 0.8H), 4.79 (s, 1.2H), 3.31-3.16 (m, 3H), 3.08-2.84 (m, 5H), 2.27 (m, 3H).

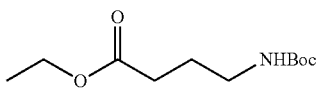 [SMILES: CCOC(=O)CCCNC(=O)OC(C)(C)C]

Ethyl 4-((tert-butoxycarbonyl)amino)butanoate (E-14)

DIPEA (2.2 eq, 44 mmol) was added dropwise to a solution of ethyl 4-aminobutyrate hydrochloride (1 eq, 20 mmol) in CH$_2$Cl$_2$ (80 mL) at 0° C. followed by the dropwise addition of di-tert-butyl dicarbonate (1.1 eq, 22 mmol). The reaction mixture was allowed to warm to room temperature and stirred for 1.5 h. The reaction was quenched with saturated aqueous ammonium chloride and extracted with dichloromethane. The combined organic extracts were washed with saturated aqueous sodium bicarbonate, dried over sodium sulfate, and concentrated under reduced pressure. Purification by flash purification column chromatography (10:40:50, EtOAc:CH$_2$Cl$_2$:Hexanes) yielded ethyl 4-((tert-butoxycarbonyl)amino)butanoate (3.66 g, 15.8 mmol, 79%) as a colorless oil. $^1$H NMR (500 MHz, Chloroform-d) δ 4.61 (s, 1H), 4.13 (q, J=7.1 Hz, 2H), 3.16 (q, J=6.6 Hz, 2H), 2.34 (t, J=7.3 Hz, 2H), 1.81 (p, J=7.1 Hz, 2H), 1.43 (s, 9H), 1.25 (t, J=7.1 Hz, 3H).

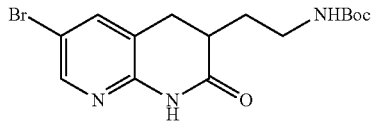 [SMILES: CC(C)(C)OC(=O)NCCC1Cc2cc(Br)cnc2NC1=O]

Tert-butyl (2-(6-bromo-2-oxo-1,2,3,4-tetrahydro-1,8-naphthyridin-3-yl)ethyl)carbamate (E-15)

To a solution of LHMDS (1 M in THF, 4 eq, 12 mmol) cooled to −78° C. was added a solution ethyl 4-((tert-butoxycarbonyl)amino)butanoate (2 eq, 6 mmol) in THF (12 mL) dropwise. The reaction mixture was stirred for 1 h followed by the portionwise addition of 5-bromo-3-(bromomethyl)pyridin-2-amine hydrobromide (1 eq, 3 mmol) via a solid addition tube kept under N$_2$. The reaction mixture was warmed to −40° C. after a few hours. After an additional 4 h, the reaction mixture was allowed to warm to room temperature overnight. The reaction mixture was quenched with water and extracted with ethyl acetate. The combined organic extracts were dried over sodium sulfate and concentrated under reduced pressure. Purification by flash purification column chromatography (01:99 to 10:90, THF:CH$_2$Cl$_2$) followed by trituration with ether/n-heptane yielded tert-butyl (2-(6-bromo-2-oxo-1,2,3,4-tetrahydro-1,8-naphthyridin-3-yl)ethyl)carbamate (0.390 g, 1.06 mmol, 35%) as a white solid. $^1$H NMR (500 MHz, Chloroform-d) δ 8.70 (s, 1H), 8.25 (d, J=2.2 Hz, 1H), 7.62 (dd, J=2.2, 0.9 Hz, 1H), 4.81 (s, 1H), 3.35 (m, 1H), 3.32-3.16 (m, 1H), 3.08 (dd, J=16.0, 6.1 Hz, 1H), 2.78 (dd, J=16.0, 9.8 Hz, 1H), 2.65 (m, 1H), 2.00 (m, 1H), 1.73 (m, 1H), 1.43 (s, 9H). $^{13}$C NMR (126 MHz, CDCl$_3$) δ 172.83, 156.20, 149.29, 147.48, 138.98, 120.10, 113.81, 79.53, 38.22, 37.37, 30.31, 29.66, 28.55.

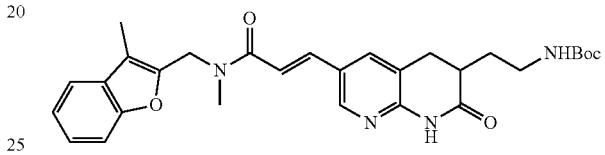

Tert-butyl (E)-(2-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)ethyl)carbamate (E-16)

Anhydrous DMA (4 mL, sparged with N$_2$ before using) was added to a flask containing N-methyl-N-((3-methylbenzofuran-2-yl)methyl)acrylamide (1.1 eq, 0.825 mmol), yielded tert-butyl (2-(6-bromo-2-oxo-1,2,3,4-tetrahydro-1,8-naphthyridin-3-yl)ethyl)carbamate (1 eq, 0.75 mmol), palladium(II) acetate (0.2 eq, 0.15 mmol), tricyclohexylphosphine tetrafluoroborate (0.4 eq, 0.30 mmol), and potassium carbonate (2 eq, 1.5 mmol). The reaction mixture was heated to 90-100° C. for 12 h. After reaction completion, the reaction mixture was diluted with dichloromethane and filtered through a pad of celite and the filtrate was washed with water. The combined organic extracts were dried over sodium sulfate and concentrated under reduced pressure. Purification by flash purification column chromatography (10:90 to 20:80, THF:CH$_2$Cl$_2$) followed by trituration with ether/n-heptane yielded tert-butyl (E)-(2-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)ethyl)carbamate (0.121 g, 0.23 mmol, 31%) as a white solid. $^1$H NMR (500 MHz, Chloroform-d) δ 8.36-8.25 (m, 1H), 8.19 (s, 1H), 7.74-7.60 (m, 2H), 7.54-7.46 (m, 1H), 7.43-7.37 (m, 1H), 7.30-7.2 (s, 2H), 7.13 (d, J=15.4 Hz, 0.4H), 6.86 (d, J=15.4 Hz, 0.6H), 4.91-4.68 (m, 3H), 3.47-3.30 (m, 1H), 3.29-3.03 (m, 5H), 2.89-2.76 (m, 1H), 2.74-2.62 (m, 1H), 2.31 (s, 3H), 2.08-1.93 (m, 1H), 1.82-1.65 (m, 1H), 1.42 (s, 9H).

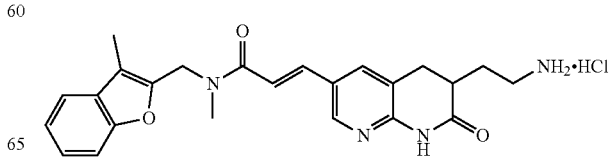

(E)-3-(6-(aminoethyl)-7-oxo-5,6,7,8-tetrahydro-1,8-naphthyridin-3-yl)-N-methyl-N-((3-methylbenzofuran-2-yl)methyl)acrylamide hydrochloride (E-17)

Anhydrous 4M HCl in dioxane (0.5 mL) was added dropwise to a solution of tert-butyl (E)-(6-(3-(methyl((3-methylbenzofuran-2-yl)methyl)amino)-3-oxoprop-1-en-1-yl)-2-oxo-1,2,3,4-tetrahydro-1,8-naphthyridin-3-yl)carbamate (1 eq, 0.233 mmol) in dioxane (1.5 mL). The reaction mixture was stirred at room temperature. After 4 h, the reaction mixture was concentrated from $CH_2Cl_2$ several times followed by trituration with ether/pentane to afford (E)-3-(6-(aminoethyl)-7-oxo-5,6,7,8-tetrahydro-1,8-naphthyridin-3-yl)-N-methyl-N-((3-methylbenzofuran-2-yl)methyl)acrylamide hydrochloride (90 mg, 0.198 mmol, 85%) as a white solid. $^1$H NMR (500 MHz, DMSO-$d_6$) δ 10.80 (s, 1H), 8.49-8.36 (m, 1H), 8.14-8.05 (m, 1H), 7.84 (s, 3H), 7.60-7.55 (m, 1H), 7.53 (d, J=15.3 Hz, 1H), 7.50-7.44 (m, 1.4H), 7.28 (td, J=7.6, 1.5 Hz, 1H), 7.24 (td, J=7.4, 1.2 Hz, 1H), 7.19 (m, 0.6H), 5.00 (s, 0.8H), 4.79 (s, 1.2H), 3.18 (s, 1.8H), 3.03-2.88 (m, 4.2H), 2.82-2.65 (m, 2H), 2.27 (d, J=2.4 Hz, 3H), 2.04 (m, 1H), 1.66 (m, 1H).

ethyl)carbamate (3 eq, 2.61 mmol). The reaction mixture was allowed to stir to room temperature and stirred for 2 h. After reaction completion, water was added to the reaction mixture and the product was extracted with diethyl ether. The combined organic extracts were dried over sodium sulfate and concentrated under reduced pressure. Purification by flash purification column chromatography (00:100 to 05:95, MeOH:$CH_2Cl_2$) yielded tert-butyl (2-(((2-amino-5-bromopyridin-3-yl)methyl)amino)ethyl)carbamate (0.276 g, 0.80 mmol, 92%). $^1$H NMR (500 MHz, Chloroform-d) δ 8.02 (d, J=2.4 Hz, 1H), 7.37 (d, J=2.3 Hz, 1H), 5.50 (s, 2H), 4.65 (s, 1H), 3.73 (s, 2H), 3.25 (q, J=5.9 Hz, 2H), 2.70 (t, J=5.9 Hz, 2H), 1.44 (s, 9H).

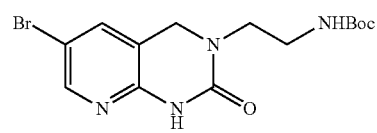 [SMILES: CC(C)(C)OC(=O)NCCN1Cc2cc(Br)cnc2NC1=O]

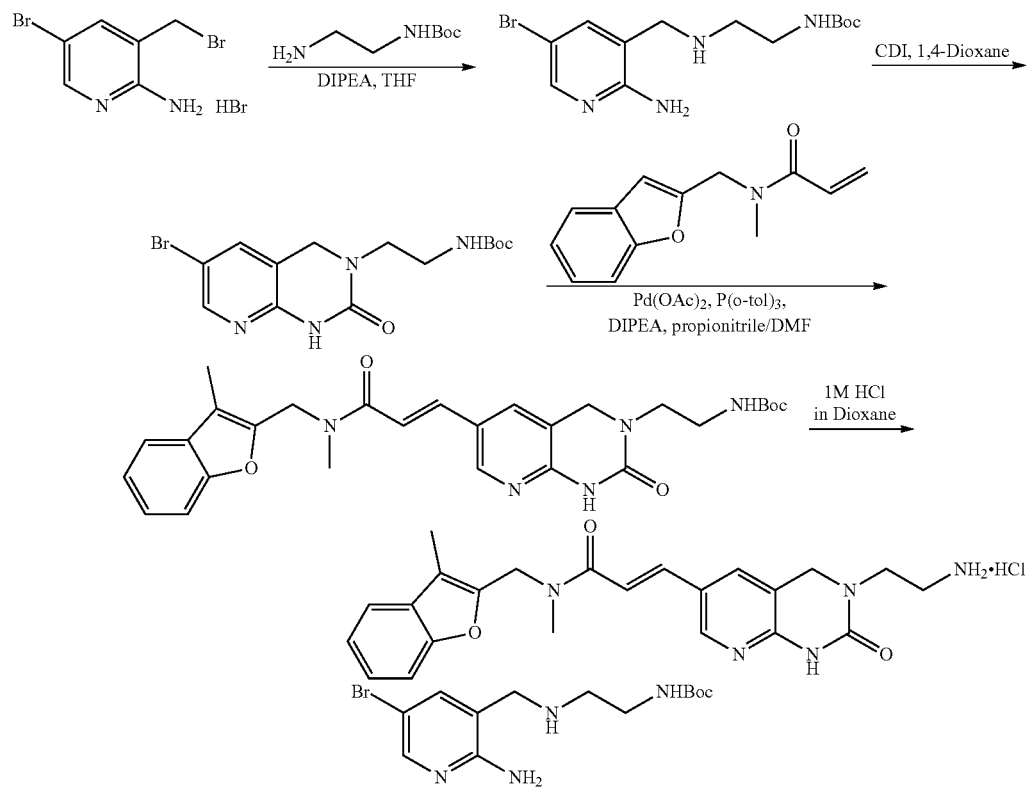

Scheme 2. Synthesis of Napthyridinone Analogs E18-E21 (see Table 5 in Example 4)

Tert-butyl (2-(((2-amino-5-bromopyridin-3-yl)methyl)amino)ethyl)carbamate (E-18)

DIPEA (2, 1.74 mmol) was added to a solution of 5-bromo-3-(bromomethyl)pyridin-2-amine hydrobromide (1 eq, 0.87 mmol) in THF (8 mL) cooled to 0° C. followed by the immediate dropwise addition of tert-butyl(amino-

Tert-butyl (2-(6-bromo-2-oxo-1,4-dihydropyrido[2,3-d]pyrimidin-3(2H)-yl)ethyl)carbamate (E-19)

Carbonyldiimidazole (1.2 eq, 0.96 mmol) was added to a solution of tert-butyl (2-(((2-amino-5-bromopyridin-3-yl)methyl)amino)ethyl)carbamate (1 eq, 0.80 mmol) in 1,4-dioxane (5 mL) and heated to reflux for 12 h. The reaction mixture was cooled to room temperature and concentrated. Purification by flash purification column chromatography (20:80 THF:$CH_2Cl_2$) followed by trituration with hexanes yielded tert-butyl (2-(6-bromo-2-oxo-1,4-dihydropyrido[2,3-d]pyrimidin-3(2H)-yl)ethyl)carbamate (0.193 g, 0.52 mmol, 65%). $^1$H NMR (500 MHz, Chloroform-d) δ 8.20 (d, J=2.3 Hz, 1H), 7.68 (s, 1H), 7.48 (s, 1H), 4.92 (s, 1H), 4.52 (s, 2H), 3.56 (t, J=6.2 Hz, 2H), 3.38 (q, J=6.1 Hz, 2H), 1.39 (s, 9H).

pyrido[2,3-d]pyrimidin-3(2H)-yl)ethyl)carbamate (0.040 g, 0.078 mmol, 29%) as a white solid. $^1$H NMR (500 MHz, DMSO-d$_6$) δ 9.53 (s, 1H), 8.33 (d, J=2.1 Hz, 1H), 7.90 (d, J=2.0 Hz, 1H), 7.55 (d, J=7.9 Hz, 1H), 7.53 (s, 2H), 7.30-7.22 (m, 2H), 6.55 (s, 1H), 4.85 (s, 2H), 4.51 (s, 2H), 3.40 (t, J=6.2 Hz, 2H), 3.18 (q, J=6.2 Hz, 3H), 3.06 (s, 3H), 2.26 (s, 3H), 1.35 (s, 9H).

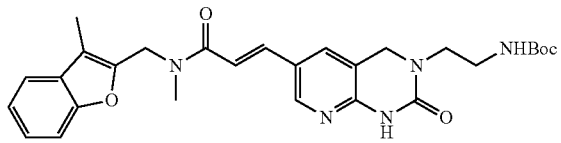 [SMILES: Cc1c(CN(C)C(=O)/C=C/c2cnc3c(c2)CN(CCNC(=O)OC(C)(C)C)C(=O)N3)oc2ccccc12]

Tert-butyl (E)-(2-(6-(3-(methyl((3-methylbenzofuran-2-yl)methyl)amino)-3-oxoprop-1-en-1-yl)-2-oxo-1,4-dihydropyrido[2,3-d]pyrimidin-3(2H)-yl)ethyl)carbamate (E-20)

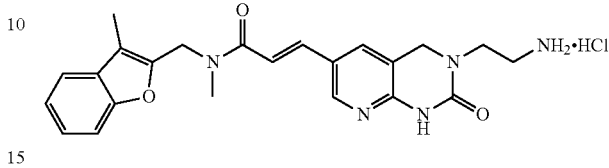

(E)-3-(3-(2-aminoethyl)-2-oxo-1,2,3,4-tetrahydropyrido[2,3-d]pyrimidin-6-yl)-N-methyl-N-((3-methylbenzofuran-2-yl)methyl)acrylamide hydrochloride (E-21)

Propionitrile (4 mL, sparged with N$_2$ before using) was added to a flask containing N-methyl-N-((3-methylbenzofuran-2-yl)methyl)acrylamide (1.1 eq, 0.297 mmol), tert-butyl (2-(6-bromo-2-oxo-1,4-dihydropyrido[2,3-d]pyrimidin-3(2H)-yl)ethyl)carbamate (1 eq, 0.27 mmol), palladium (II) acetate (0.2 eq, 0.054 mmol), tri(o-tolyl)phosphine (0.4 eq, 0.108 mmol), and DIPEA (4 eq, 1.08 mmol). The reaction mixture was heated to 90-100° C. for 1 day. After reaction completion, the reaction mixture was diluted with dichloromethane and filtered through a pad of celite and the filtrate was washed with water. The combined organic extracts were dried over sodium sulfate and concentrated under reduced pressure. Purification by flash purification column chromatography (10:90 to 20:80, THF:CH$_2$Cl$_2$) followed by trituration with ether/n-heptane yielded tert-butyl (E)-(2-(6-(3-(methyl((3-methylbenzofuran-2-yl)methyl)amino)-3-oxoprop-1-en-1-yl)-2-oxo-1,4-dihydro- Anhydrous 4M HCl in dioxane (0.5 mL) was added dropwise to a solution of tert-butyl (E)-(2-(6-(3-(methyl((3-methylbenzofuran-2-yl)methyl)amino)-3-oxoprop-1-en-1-yl)-2-oxo-1,4-dihydropyrido[2,3-d]pyrimidin-3(2H)-yl)ethyl)carbamate (1 eq, 0.058 mmol) in dioxane (1.5 mL). The reaction mixture was stirred at room temperature. After 4 h, the reaction mixture was concentrated from CH$_2$Cl$_2$ several times followed by trituration with ether/pentane to afford ((E)-3-(3-(2-aminoethyl)-2-oxo-1,2,3,4-tetrahydropyrido[2,3-d]pyrimidin-6-yl)-N-methyl-N-((3-methylbenzofuran-2-yl)methyl)acrylamide hydrochloride (23 mg, 0.05 mmol, 87%) as a white solid. $^1$H NMR (500 MHz, DMSO-d$_6$) δ 10.06 (s, 1H), 8.45-8.33 (m, 1H), 8.01-7.94 (m, 1H), 7.88 (s, 3H), 7.59-7.54 (m, 1H), 7.54-7.41 (m, 2.4H), 7.32-7.21 (m, 2H), 7.17 (d, J=15.3 Hz, 0.6H), 4.98 (s, 0.8H), 4.79 (s, 1.2H), 4.53 (s, 2H), 3.66-3.50 (m, 2H), 3.18 (s, 1.8H), 3.10-2.97 (m, 2H), 2.93 (s, 1.2H), 2.26 (s, 3H).

Scheme 3. Synthesis of Napthyridinone Analogs E22-E26 (see Table 5 in Example 4)

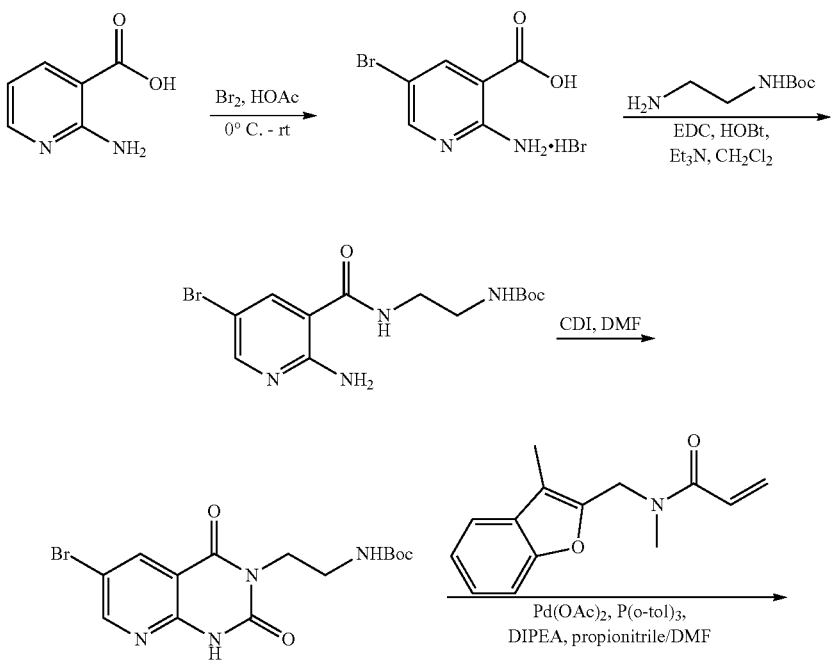

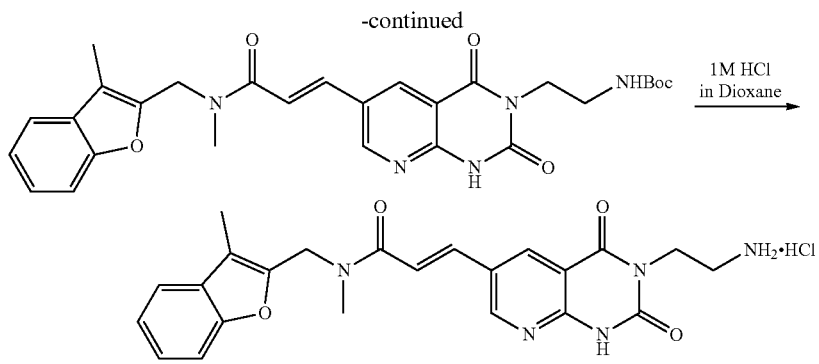

Hz, 1H), 7.82 (d, J=2.3 Hz, 1H), 7.51 (s, 1H), 6.44 (s, 2H), 4.99 (s, 1H), 3.48 (m, 2H), 3.41 (m, 2H), 1.46 (s, 9H).

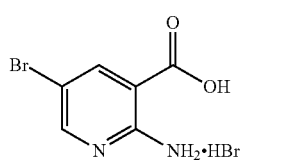

2-Amino-5-bromo-nicotinic acid hydrobromide (E-22)

Bromine (1.01 eq, 36.49 mmol) was added dropwise to a suspension of 2-amino-nicotinic acid (1 eq, 36.13 mmol) in glacial acetic acid (55 mL) cooled in an ice bath. After the addition of bromine was complete, the mixture was stirred at room temperature overnight. The solid was filtered and rinsed with ether to afford 2-amino-5-bromo-nicotinic acid hydrobromide (9.77 g, 33.02, 91%) as a yellow solid. $^1$H NMR (500 MHz, DMSO-d$_6$) δ 8.33 (d, J=2.6 Hz, 1H), 8.21 (d, J=2.5 Hz, 1H). $^{13}$C NMR (126 MHz, DMSO) δ 166.82, 156.91, 150.85, 143.19, 108.72, 103.73.

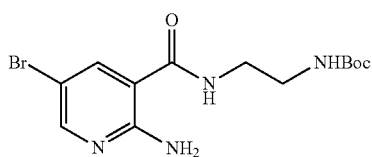

Tert-butyl (2-(2-amino-5-bromonicotinamido)ethyl) carbamate (E-23)

To a suspension of 2-amino-5-bromo-nicotinic acid hydrobromide (1 eq, 3.38 mmol) in CH$_2$Cl$_2$ (35 mL) was added triethylamine (1.5 eq, 5.07 mmol), EDC (1.05 eq, 3.55 mmol), and HOBt (1.05 eq, 3.55 mmol) at 0° C. The mixture was stirred for 10 min followed by the addition of N-Boc-ethylenediamine (1.05 eq, 3.55 mmol). The reaction mixture was allowed to warm to room temperature and stirred overnight. After reaction completion, the mixture was extracted with CH$_2$Cl$_2$ from 2M NaOH (aq). The combined organic extracts were dried over sodium sulfate and concentrated. Purification by flash purification column chromatography (05:95 MeOH:CH$_2$Cl$_2$) followed by trituration with diethyl ether afforded tert-butyl (2-(2-amino-5-bromonicotinamido)ethyl)carbamate (0.844 g, mmol, 70%) as a white solid. $^1$H NMR (500 MHz, CDCl$_3$) δ 8.16 (d, J=2.3

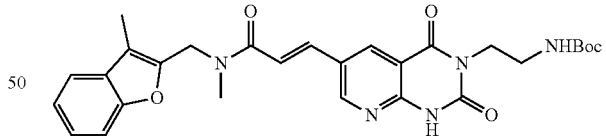

Tert-butyl (2-(6-bromo-2-oxo-1,4-dihydropyrido[2,3-d]pyrimidin-3(2H)-yl)ethyl)carbamate (E-24)

Carbonyldiimidazole (1.2 eq, 0.67 mmol) was added to a solution of tert-butyl (2-(((2-amino-5-bromopyridin-3-yl) methyl)amino)ethyl)carbamate (1 eq, 0.56 mmol) in DMF (5 mL) and heated to 80° C. for 12 h. The reaction mixture was cooled to room temperature and concentrated. Purification by flash purification column chromatography (10:90 to 20:80 THF:CH$_2$Cl$_2$) followed by trituration with ethyl acetate/diethyl ether yielded tert-butyl (2-(6-bromo-2,4-dioxo-1,4-dihydropyrido[2,3-d]pyrimidin-3(2H)-yl)ethyl)carbamate 0.118 g, 0.31 mmol, 55%) as a white solid. $^1$H NMR (500 MHz, DMSO-d$_6$) δ 12.09 (s, 1H), 8.73 (d, J=2.5 Hz, 1H), 8.39 (d, J=2.4 Hz, 1H), 6.84 (t, J=6.2 Hz, 1H), 3.94 (t, J=5.7 Hz, 2H), 3.19 (q, J=6.0 Hz, 2H), 1.28 (s, 9H).

Tert-butyl (E)-(2-(6-(3-(methyl((3-methylbenzo-furan-2-yl)methyl)amino)-3-oxoprop-1-en-1-yl)-2,4-dioxo-1,4-dihydropyrido[2,3-d]pyrimidin-3(2H)-yl) ethyl)carbamate (E-25)

Propionitrile (4 mL, sparged with N$_2$ before using) and DMF (2 mL, sparged with N$_2$ before using) was added to a flask containing N-methyl-N-((3-methylbenzofuran-2-yl) methyl)acrylamide (1.1 eq, 0.29 mmol), yielded tert-butyl (2-(6-bromo-2,4-dioxo-1,4-dihydropyrido[2,3-d]pyrimidin-3(2H)-yl)ethyl)carbamate (1 eq, 0.26 mmol), palladium(II) acetate (0.2 eq, 0.052 mmol), tri(o-tolyl)phosphine (0.4 eq, 0.104 mmol), and DIPEA (4 eq, 1.04 mmol). The reaction mixture was heated to 90-100° C. for 1 day. After reaction completion, the reaction mixture was diluted with dichloromethane and filtered through a pad of celite and the filtrate was washed with water. The combined organic extracts were dried over sodium sulfate and concentrated under reduced pressure. Purification by flash purification column chromatography (10:90 to 20:80, THF:CH$_2$Cl$_2$) followed by trituration with ether/n-heptane yielded tert-butyl (E)-(2-(6-(3-(methyl((3-methylbenzofuran-2-yl)methyl)amino)-3-oxoprop-1-en-1-yl)-2,4-dioxo-1,4-dihydropyrido[2,3-d]pyrimidin-3(2H)-yl)ethyl)carbamate (0.051 g, 0.0955 mmol, 37%) as a white solid. $^1$H NMR (500 MHz, Chloroform-d) δ 8.92 (s, 1H), 8.77-8.66 (m, 1H), 8.66-8.56 (m, 1H), 7.80-7.67 (m, 1H), 7.57-7.46 (m, 1H), 7.46-7.38 (m, 1H), 7.36-7.19 (m, 2H), 7.02 (d, J=15.4 Hz, 1H), 4.85 (s, 2H), 4.74 (s, 1H), 4.35-4.12 (m, 2H), 3.61-3.37 (m, 2H), 3.27 (s, 2H), 3.11 (s, 1H), 2.33 (s, 3H), 1.31 (s, 9H).

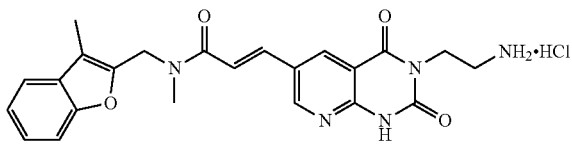

(E)-3-(3-(2-Aminoethyl)-2,4-dioxo-1,2,3,4-tetrahydropyrido[2,3-d]pyrimidin-6-yl)-N-methyl-N-((3-methylbenzofuran-2-yl)methyl)acrylamide hydrochloride (E-26)

Anhydrous 4M HCl in dioxane (0.5 mL) was added dropwise to a solution of tert-butyl (E)-(2-(6-(3-(methyl((3-methylbenzofuran-2-yl)methyl)amino)-3-oxoprop-1-en-1-yl)-2-oxo-1,4-dihydropyrido[2,3-d]pyrimidin-3(2H)-yl)ethyl)carbamate (1 eq, 0.075 mmol) in dioxane (1.5 mL). The reaction mixture was stirred at room temperature. After 4 h, the reaction mixture was concentrated from CH$_2$Cl$_2$ several times followed by trituration with ether to afford (E)-3-(3-(2-aminoethyl)-2,4-dioxo-1,2,3,4-tetrahydropyrido[2,3-d]pyrimidin-6-yl)-N-methyl-N-((3-methylbenzofuran-2-yl)methyl)acrylamide hydrochloride (27 mg, 0.057 mmol, 76%) as a white solid. $^1$H NMR (500 MHz, DMSO-d$_6$) δ 12.33-12.16 (m, 1H), 9.02-8.97 (m, 1H), 8.78 (d, J=2.3 Hz, 0.4H), 8.71 (d, J=2.3 Hz, 0.6H), 7.83 (s, 3H), 7.74-7.62 (m, 1.4H), 7.60-7.54 (m, 1H), 7.52-7.41 (m, 1.6H), 7.33-7.21 (m, 2H), 5.05 (s, 0.8H), 4.80 (s, 1.2H), 4.26-4.06 (m, 2H), 3.18 (s, 1.8H), 3.13-3.03 (m, 2H), 2.95 (s, 1.2H), 2.32-2.25 (m, 3H).

Scheme 4. Synthesis of Analogs with Reduced Rotatable Bonds E27-E29 (see Table 5 in Example 4)

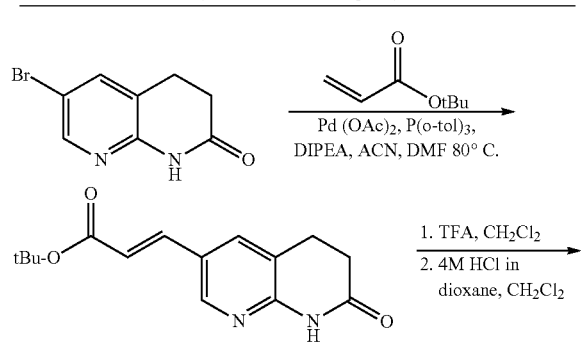

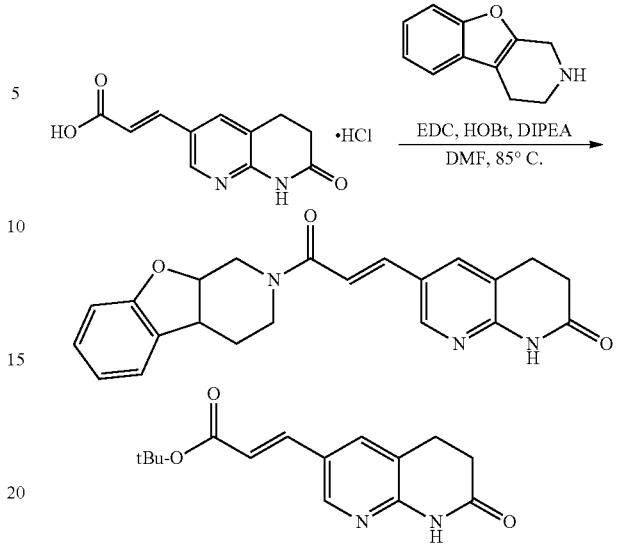

Tert-butyl (E)-3-(7-oxo-5,6,7,8-tetrahydro-1,8-naphthyridin-3-yl)acrylate (E-27)

A solution of 6-bromo-3,4-dihydro-1H-[1,8]napthyridin-2-one (1 eq, 5.285 mmol), tert-butyl acrylate (1.5 eq, 7.93 mmol), and DIPEA (1.5 eq, 7.93 mmol) in acetonitrile (30 mL) and DMF (8 mL) were degassed with N$_2$ for 20 min followed by the addition of palladium(II) acetate (0.05 eq, 0.264 mmol), tri(o-tolyl)phosphine (0.1 eq, 0.529 mmol). The reaction mixture was heated to 80° C. for 12 h. Upon reaction completion, the reaction mixture was concentrated. The residue was taken up in MeOH/CH$_2$Cl$_2$, filtered through a pad of celite and the filtrate was washed with water. The combined organic extracts were dried over sodium sulfate and concentrated under reduced pressure. Purification by flash purification column chromatography (05:95 to 10:90, THF:CH$_2$Cl$_2$) followed by trituration with cold ethanol yielded tert-butyl (E)-3-(7-oxo-5,6,7,8-tetrahydro-1,8-naphthyridin-3-yl)acrylate (0.640 g, 2.33 mmol, 44%). $^1$H NMR (500 MHz, Chloroform-d) δ 8.94 (s, 1H), 8.32 (d, J=2.1 Hz, 1H), 7.65 (s, 1H), 7.51 (d, J=16.0 Hz, 1H), 6.33 (d, J=16.0 Hz, 1H), 2.99 (t, J=7.6 Hz, 2H), 2.71 (dd, J=8.4, 6.8 Hz, 2H), 1.53 (s, 9H). $^{13}$C NMR (126 MHz, CDCl$_3$) δ 170.97, 165.97, 151.95, 147.37, 139.43, 134.05, 126.16, 120.57, 118.84, 80.99, 30.40, 28.34, 24.22.

(E)-3-(7-oxo-5,6,7,8-tetrahydro-1,8-naphthyridin-3-yl)acrylic acid hydrochloride (E-28)

To a suspension of yielded tert-butyl (E)-3-(7-oxo-5,6,7,8-tetrahydro-1,8-naphthyridin-3-yl)acrylate (1 eq, 2.18 mmol) in CH$_2$Cl$_2$ (10 mL) was added trifluoroacetic acid (2 mL). The reaction mixture was stirred for 6 h at room temperature. After reaction completion, the reaction mixture was concentrated several times from CH$_2$Cl$_2$ under reduced pressure. The crude product was suspended in 4M HCl in dioxane (10 mL), sonicated, filtered, and rinsed with diethyl ether to afford—(0.555 g, 2.18 mmol, quantitative) as a white solid. $^1$H NMR (500 MHz, DMSO-d$_6$) δ 10.70 (s, 1H), 8.35 (d, J=2.2 Hz, 1H), 8.03 (d, J=2.1 Hz, 1H), 7.54 (d, J=16.0 Hz, 1H), 6.51 (d, J=16.0 Hz, 1H), 2.91 (t, J=7.6 Hz, 2H), 2.53 (dd, J=8.5, 6.7 Hz, 2H). $^{13}$C NMR (126 MHz, DMSO) δ 171.03, 167.48, 152.74, 147.26, 140.61, 133.85, 124.75, 119.27, 118.40, 29.98, 23.28.

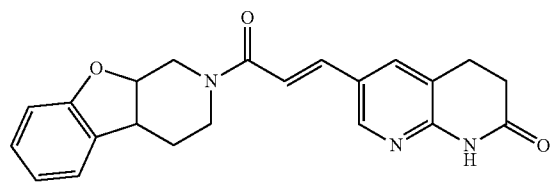 [SMILES: O=C1CCc2cc(/C=C/C(=O)N3CCC4c5ccccc5OC4C3)cnc2N1]

(E)-6-(3-oxo-3-(3,4,4a,9a-tetrahydrobenzofuro[2,3-c]pyridin-2(1H)-yl)prop-1-en-1-yl)-3,4-dihydro-1,8-naphthyridin-2(1H)-one (E-29)

To a solution of 1,2,3,4-tetraydrobenzofuro[2,3-c]pyridine hydrochloride (1 eq, 0.36 mmol), (E)-3-(7-oxo-5,6,7,8-tetrahydro-1,8-naphthyridin-3-yl)acrylic acid hydrochloride (1.2 eq, 0.432 mmol), HOBt (1.2 eq, 0.432 mmol), in DMF (2.5 mL) was added EDC (1.2 eq, 0.432 mmol). The reaction mixture was heated to 85° C. for 6 h. The solvent was reduced to a few mL. The crude reaction mixture was diluted with CH$_2$Cl$_2$ and washed with saturated aqueous sodium bicarbonate. The organic extracts were dried over sodium sulfate and concentrated under reduced pressure. Purification by flash column chromatography (02:98 to 05:95, MeOH:CH$_2$Cl$_2$) yielded (E)-6-(3-oxo-3-(3,4,4a,9a-tetrahydrobenzofuro[2,3-c]pyridin-2(1H)-yl)prop-1-en-1-yl)-3,4-dihydro-1,8-naphthyridin-2(1H)-one (86 g, 0.23 mmol, 64%) as a white solid. $^1$H NMR (500 MHz, Chloroform-d) δ 8.51-8.38 (m, 1H), 8.36 (s, 1H), 7.73-7.62 (m, 2H), 7.54-7.39 (m, 2H), 7.33-7.20 (m, 2H), 7.03-6.84 (m, 1H), 4.99-4.74 (m, 2H), 4.20-3.87 (m, 2H), 3.12-2.95 (m, 2H), 2.96-2.79 (m, 2H), 2.78-2.63 (m, 2H).

Example 1-3: Exemplary Naphthyridinone Analogs

The following naphthyridinone analogs can be prepared using the procedures described herein, including analogs having the (S)- or (R)-configuration.

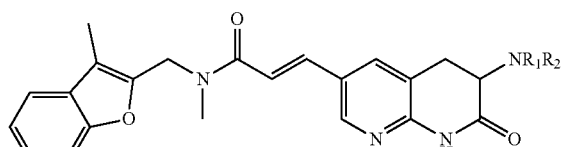

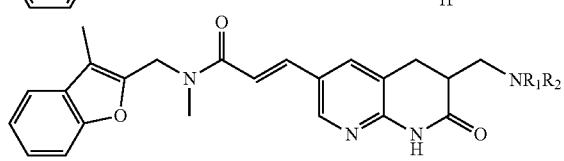

-continued

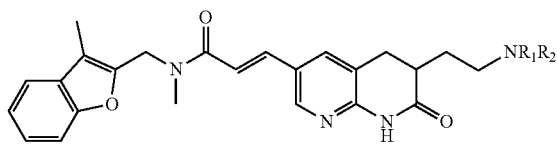

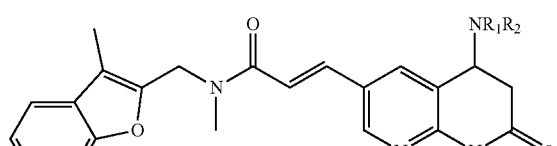

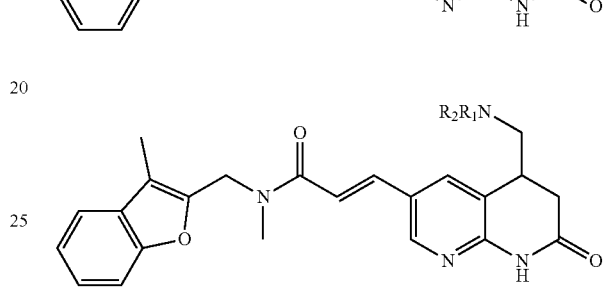

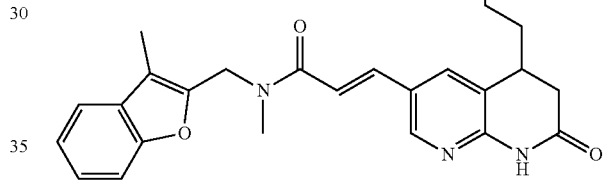

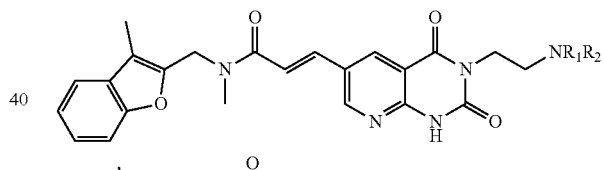

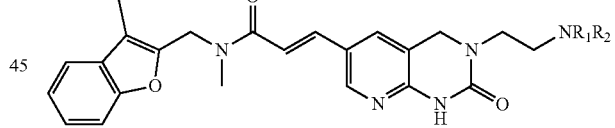

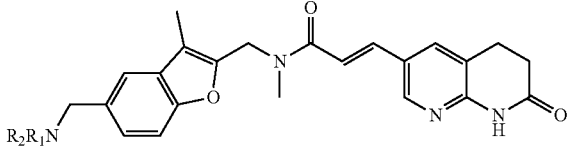

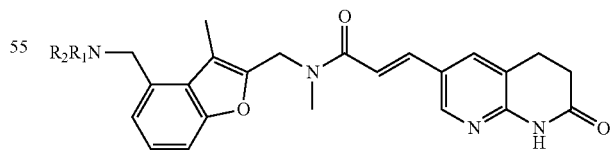

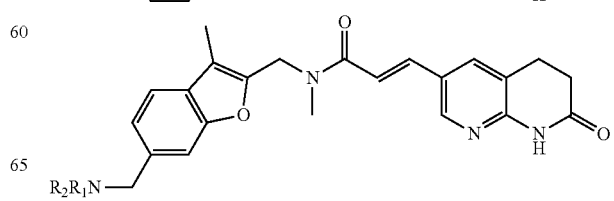

-continued
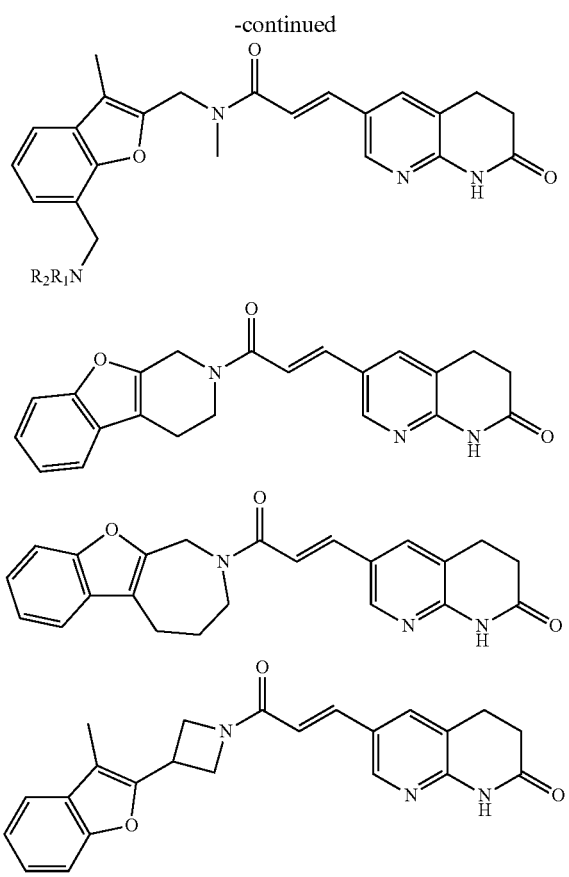
R1 = R2 = H
R1 = H, R2 = CH3
R1 = R2 = CH3
R1 = H, R2 = C(O)CH3
R1 = H, R2 = Boc
Example 1-4: Exemplary Synthesis of Benzofuroazepine Analogs
Benzofuroazepine analogs can be prepared using the procedures described herein.
R=amine substituent
-continued
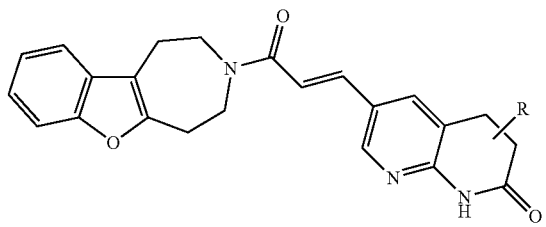
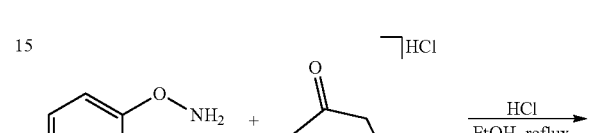
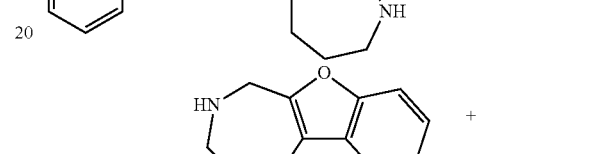
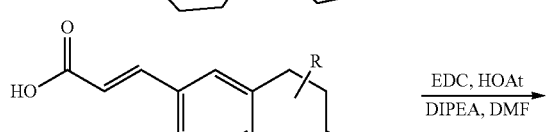
Example 2: Preparation of Exemplary FtsZ Inhibitors (See Table 5 in Example 4)
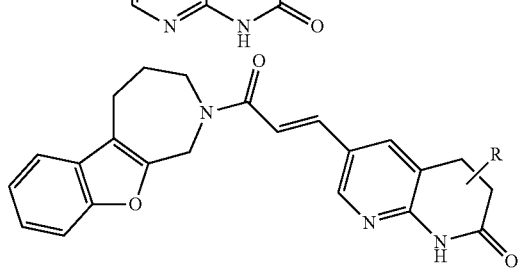
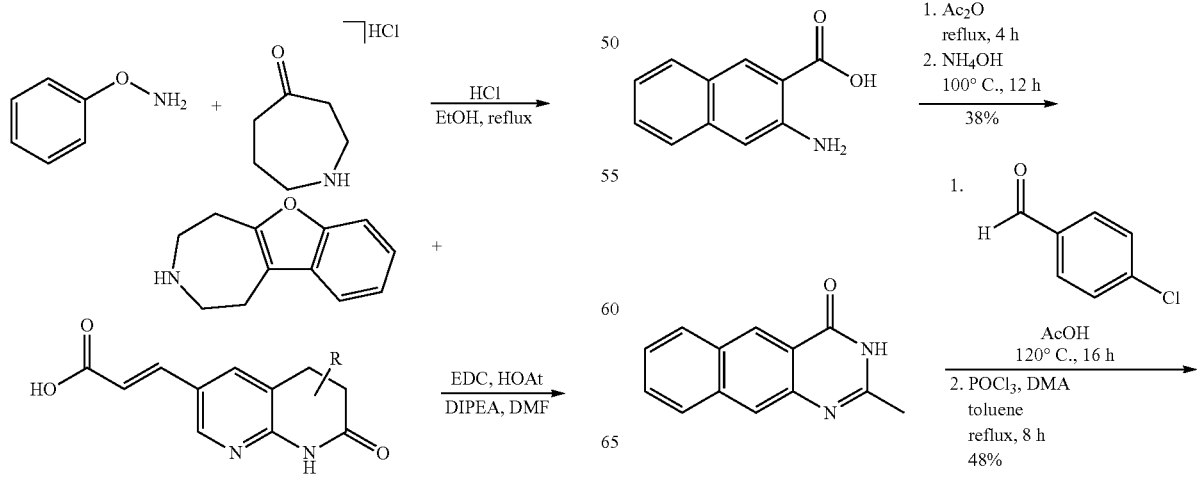

-continued

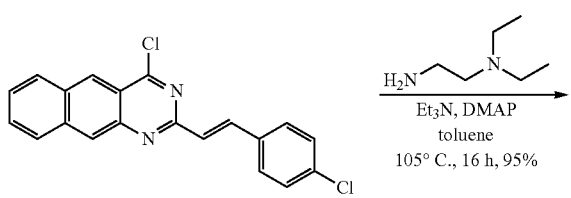

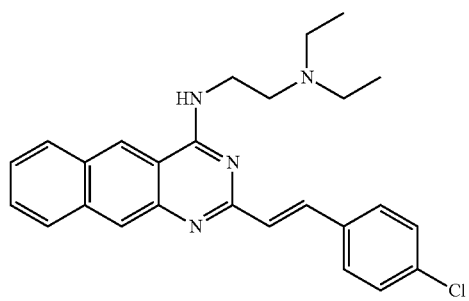

General Method A:

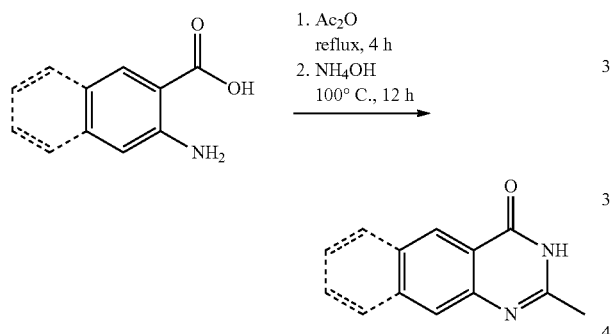

2-Amino-3-naphthoic acid or 2-amino-3-benzoic acid (1 eq) was dissolved in acetic anhydride (0.2 M final) and heated to reflux. After stirring a reflux for 4 h, reaction mixture was cooled to room temperature and solvent was removed by rotary evaporator. Concentrated NH₄OH (0.2 M final) was added to residue and the solution was heated at 100° C. for 12 h. Once cooled to room temperature, the resulting precipitate was collected by filtration and washed with H₂O and methanol yielding a solid (1.72 g, 72%). ¹H and ¹³C NMR were consistent with previous reports.

General Method B:

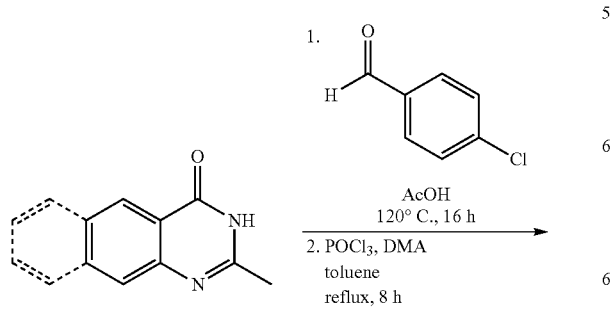

-continued

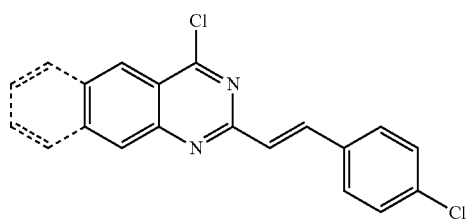

Lactam (1 eq) was dissolved in acetic acid (0.1 M). 4-chlorobenzaldehyde (1.1 eq) was added and mixture was heated to reflux. After stirring at reflux for 16 h, reaction mixture was cooled to room temperature and precipitate was collected by filtration and dried under vacuum. Residue was suspended in toluene (0.04 M). N,N-dimethylaniline (2 eq) was added followed by POCl₃ (2 eq) and mixture was heated to reflux. After stirring at reflux for 8 h, reaction mixture was cooled to room temperature and decanted into separate round-bottom flask. Solvent was removed by rotary evaporator to give a purple residue which was recrystallized from dichloromethane or purified by silica gel chromatography.

General Method C:

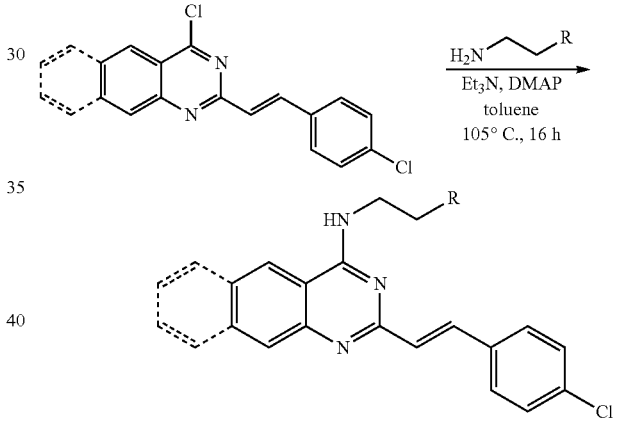

Chloroquinazoline (1 eq) and DMAP (0.2 eq) were dissolved in toluene (0.1 M). Triethylamine (1.5 eq) and primary amine (1.1 eq) were added. Reaction vessel was sealed and heated to 105° C. for 16 h. Reaction mixture was cooled to room temperature, and solvent was removed by rotary evaporator. Residue was purified by silica gel chromatography (1-15% CH₂Cl₂:CH₃OH).

Z1

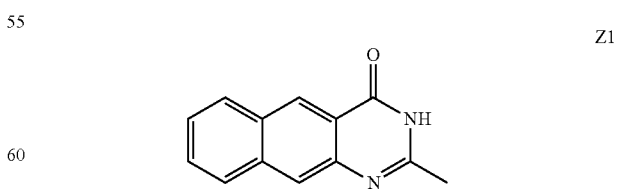

2-Methylbenzo[g]quinazolin-4(3H)-one (Z1)—Synthesized via general method A (1.72 g, 72%). ¹H and ¹³C NMR were consistent with previous reports. ¹ HRMS (ESI) m/z: [M+H]⁺ Calcd for $C_{13}H_{11}N_2O$ 211.0871; Found 211.0869.

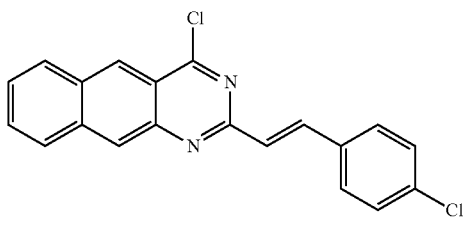

(E)-4-Chloro-2-(4-chlorostyryl)benzo[g]quinazoline (Z2)—Synthesized via general method B (321.6 mg, 48%). $^1$H NMR (500 MHz, CDCl$_3$) δ 8.85 (s, 1H), 8.55 (s, 1H), 8.16-8.07 (m, 3H), 7.67 (dd, J=8.3, 6.6 Hz, 1H), 7.64-7.59 (m, 3H), 7.42-7.38 (m, 2H), 7.33 (d, J=15.8 Hz, 1H). $^{13}$C NMR (126 MHz, CDCl$_3$) δ 163.71, 158.68, 138.78, 137.31, 135.33, 134.60, 132.54, 129.50, 129.28, 129.15, 129.13, 128.45, 127.42, 127.11, 126.56, 120.50. HRMS (ESI) m/z: [M+H]$^+$ Calcd for C$_{20}$H$_{13}$N$_2$Cl$_2$ 351.0456; Found 351.0448.

Zantrin Z3

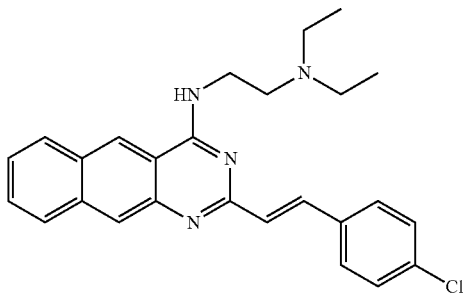

Zantrin Z3—Synthesized via general method C (83.3 mg, 95%). $^1$H NMR (500 MHz, DMSO-d$_6$) δ 8.88 (s, 1H), 8.68 (s, 1H), 8.26 (s, 1H), 8.04 (dd, J=23.7, 8.4 Hz, 2H), 7.95 (d, J=15.9 Hz, 1H), 7.72 (d, J=8.2 Hz, 2H), 7.60 (ddd, J=8.3, 6.7, 1.2 Hz, 1H), 7.54 (ddd, J=8.1, 6.6, 1.2 Hz, 1H), 7.51-7.44 (m, 2H), 7.21 (d, J=15.9 Hz, 1H), 3.83 (s, 2H), 3.36 (s, 5H), 2.88 (s, 2H), 2.72 (s, 4H), 1.07 (t, J=7.2 Hz, 6H). $^{13}$C NMR (126 MHz, DMSO) δ 159.44, 159.42, 145.58, 135.39, 135.06, 134.83, 133.11, 130.48, 129.01, 128.92, 128.68, 127.66, 125.75, 124.30, 122.75, 114.25, 50.50, 47.01. HRMS (ESI) m/z: [M+H]$^+$ Calcd for C$_{26}$H$_{28}$N$_4$Cl 431.2002; Found 431.1984.

Z5

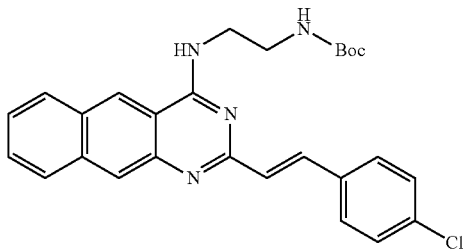

Z5—Synthesized via general method C (29.6 mg, 90%). HRMS (ESI) m/z: [M+H]$^+$ Calcd for C$_{27}$H$_{28}$N$_4$O$_2$Cl 475.1901; Found 475.1899.

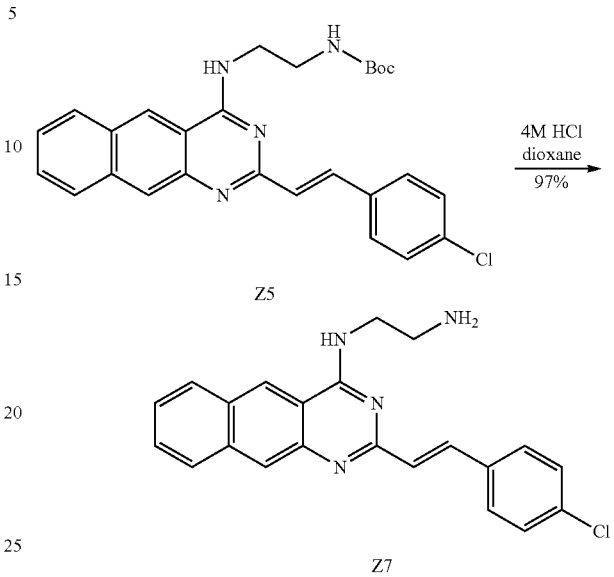

(E)-N$^1$-(2-(4-chlorostyryl)benzo[g]quinazolin-4-yl)ethane-1,2-diamine (Z7)—Z5 (28.2 mg, 0.06 mmol) was dissolved in 4 M HCl in dioxane (1 mL) and heated to 40° C. After stirring for 1 h, reaction was basified with 10% NaOH and extracted with EtOAc. Organic layer was washed with brine, dried over Na$_2$SO$_4$, and evaporated. Residue was purified by silica gel chromatography (95:4.5:0.5 CH$_2$Cl$_2$:CH$_3$OH:NH$_4$OH) to give Z7 as an orange solid (23.6 mg, 96%). $^1$H NMR (500 MHz, Methanol-d$_4$) δ 8.66 (s, 1H), 8.17 (s, 1H), 8.00 (m, 3H) 7.64 (dd, J=8.5, 1.5 Hz, 2H), 7.57 (ddd, J=8.2, 6.6, 1.3 Hz, 1H), 7.49 (ddd, J=8.1, 6.7, 1.2 Hz, 1H), 7.40 (d, J=8.5 Hz, 2H), 7.11 (d, J=15.7 Hz, 1H), 3.92 (t, J=6.3 Hz, 2H), 3.12 (t, J=6.3 Hz, 2H). $^{13}$C NMR (126 MHz, MeOD) δ 161.67, 161.53, 146.05, 137.87, 137.39, 136.48, 135.61, 132.64, 130.01, 129.96, 129.64, 129.03, 128.72, 126.96, 124.50, 123.70, 115.30, 44.39, 41.76. HRMS (ESI) m/z: [M+H]$^+$ Calcd for C$_{22}$H$_{20}$N$_4$Cl 375.1376; Found 375.1368.

Scheme 5. Synthesis of quinazoline derivatives.

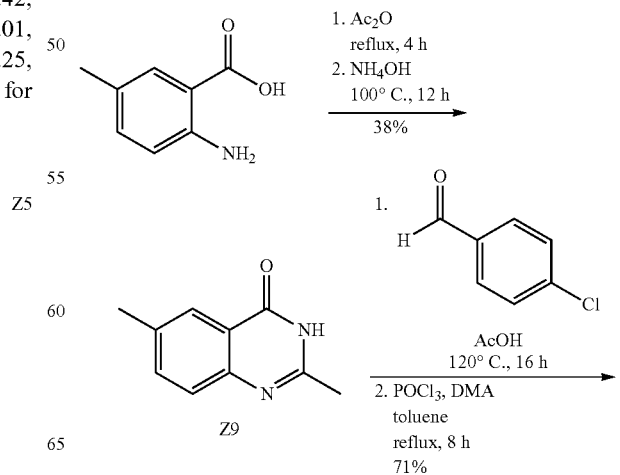

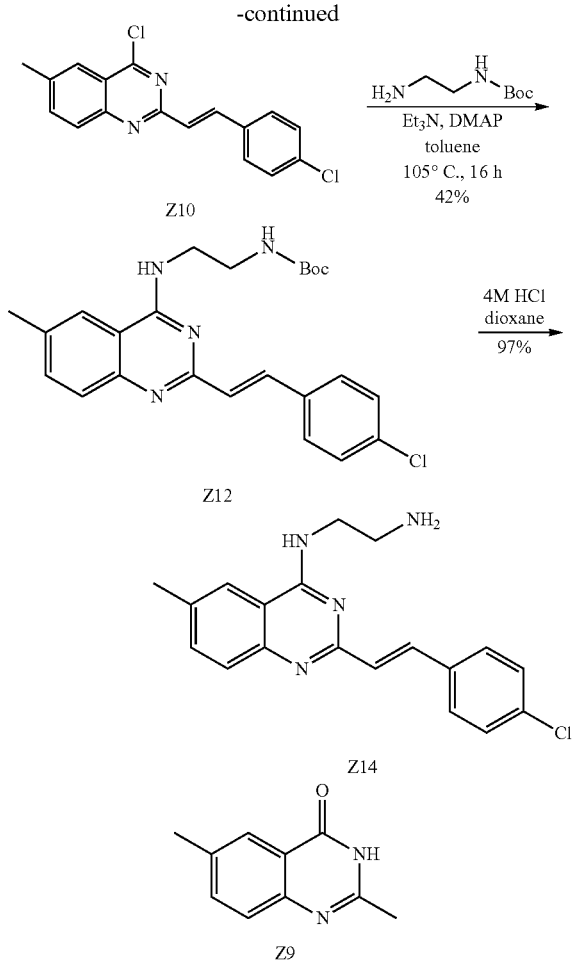

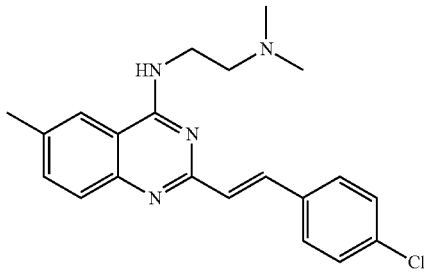

(E)-N$^1$-(2-(4-Chlorostyryl)-6-methylquinazolin-4-yl)-N$^2$,N$^2$-dimethylethane-1,2-diamine Z11—Synthesized via general method C (20.3 mg, 96%). $^1$H NMR (500 MHz, CDCl$_3$) δ 7.90 (d, J=15.8 Hz, 1H), 7.68 (d, J=8.1 Hz, 1H), 7.55-7.45 (m, 4H), 7.34-7.28 (m, 2H), 7.16 (d, J=15.8 Hz, 1H), 6.53 (t, J=4.6 Hz, 1H), 3.77 (q, J=5.5 Hz, 2H), 2.66 (t, J=5.9 Hz, 2H), 2.45 (s, 3H), 2.33 (s, 5H). $^{13}$C NMR (126 MHz, CDCl$_3$) δ 159.81, 158.74, 148.35, 135.49, 135.32, 135.06, 134.43, 134.06, 129.98, 128.90, 128.61, 127.96, 120.36, 113.88, 57.70, 45.33, 38.25, 21.70. HRMS (ESI) m/z: [M+H]$^+$ Calcd for C$_{21}$H$_{24}$N$_4$Cl 367.1689; Found 367.1693.

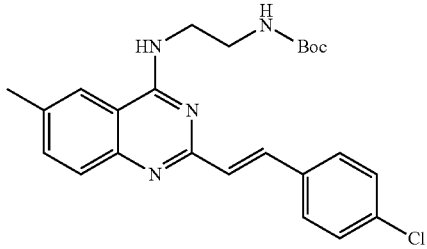

Tert-butyl (E)-(2-((2-(4-chlorostyryl)-6-methylquinazolin-4-yl)amino)ethyl) carbamate (Z12)—Synthesized via general method C (231.4 mg, 42%). $^1$H NMR (500 MHz, CDCl$_3$) δ 7.90 (d, J=15.9 Hz, 1H), 7.70 (d, J=8.4 Hz, 1H), 7.59-7.50 (m, 4H), 7.33 (d, J=8.4 Hz, 2H), 7.16 (d, J=15.8 Hz, 1H), 6.99 (s, 1H), 5.32 (d, J=6.4 Hz, 1H), 3.80 (dd, J=7.0, 3.9 Hz, 2H), 3.57 (q, J=5.8 Hz, 2H), 2.47 (s, 3H), 1.43 (s, 9H). $^{13}$C NMR (126 MHz, CDCl$_3$) δ 159.80, 159.31, 158.17, 135.74, 135.37, 135.28, 134.57, 134.22, 129.84, 128.99, 128.74, 127.91, 120.77, 113.93, 80.30, 43.97, 40.27, 28.48, 21.75. HRMS (ESI) m/z: [M+H]$^+$ Calcd for C$_{24}$H$_{28}$N$_4$O$_2$Cl 439.1901; Found 439.1891.

2,6-Dimethylquinazolin-4(3H)-one (Z9)—Synthesized via general method A (880.4 mg, 38%). $^1$H NMR (500 MHz, DMSO-d$_6$) δ 12.08 (s, 1H), 7.86 (s, 1H), 7.58 (dd, J=8.3, 2.1 Hz, 1H), 7.47 (d, J=8.3 Hz, 1H), 2.41 (s, 3H), 2.32 (s, 3H). HRMS (ESI) m/z: [M+H]$^+$ Calcd for C$_{10}$H$_{11}$N$_2$O 175.0871; Found 175.0872.

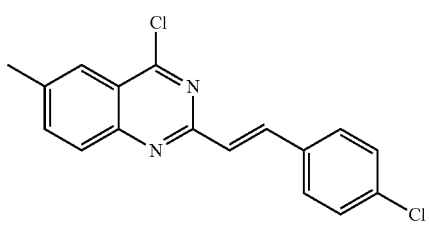

(E)-4-Chloro-2-(4-chlorostyryl)-6-methylquinazoline (Z10)—Synthesized via general method B (1.745 g, 71%). $^1$H NMR (500 MHz, CDCl$_3$) δ 7.95 (d, J=16.0 Hz, 1H), 7.89 (dt, J=1.8, 0.9 Hz, 1H), 7.80 (d, J=8.5 Hz, 1H), 7.66 (dd, J=8.6, 2.0 Hz, 1H), 7.50-7.46 (m, 2H), 7.30-7.26 (m, 2H), 7.17 (d, J=15.9 Hz, 1H), 2.50 (d, J=1.0 Hz, 3H). $^{13}$C NMR (126 MHz, CDCl$_3$) δ 161.52, 159.47, 150.35, 138.94, 137.81, 137.32, 135.10, 134.61, 129.21, 128.98, 128.28, 127.35, 124.87, 122.28, 22.00. HRMS (ESI) m/z: [M+H]$^+$ Calcd for C$_{17}$H$_{13}$N$_2$Cl$_2$ 315.0456; Found 315.0457.

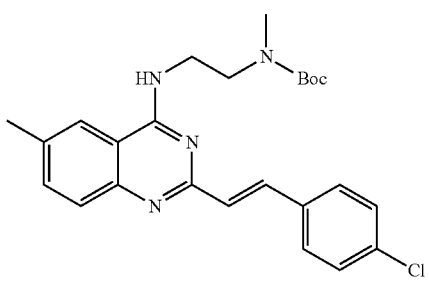

Tert-butyl (E)-(2-((2-(4-chlorostyryl)-6-methylquinazolin-4-yl)amino)ethyl) (methyl)carbamate Z13—Synthesized via general method C (124.5 mg, 86%). $^1$H NMR (500 MHz, Methanol-$d_4$) δ 7.89 (dd, J=42.0, 15.8 Hz, 1H), 7.72 (d, J=49.5 Hz, 1H), 7.53 (t, J=7.1 Hz, 4H), 7.33 (d, J=8.3 Hz, 2H), 7.06-6.97 (m, 1H), 3.78 (t, J=6.1 Hz, 2H), 3.63 (t, J=5.6 Hz, 1.11H major), 3.56 (t, J=6.4 Hz, 0.87H minor), 2.93 (s, 3H), 2.43 (d, J=4.1 Hz, 3H), 1.36 (s, 4H minor), 1.07 (s, 5H major). HRMS (ESI) m/z: [M+H]$^+$ Calcd for $C_{25}H_{30}N_4O_2Cl$ 453.2057: Found 453.2057.

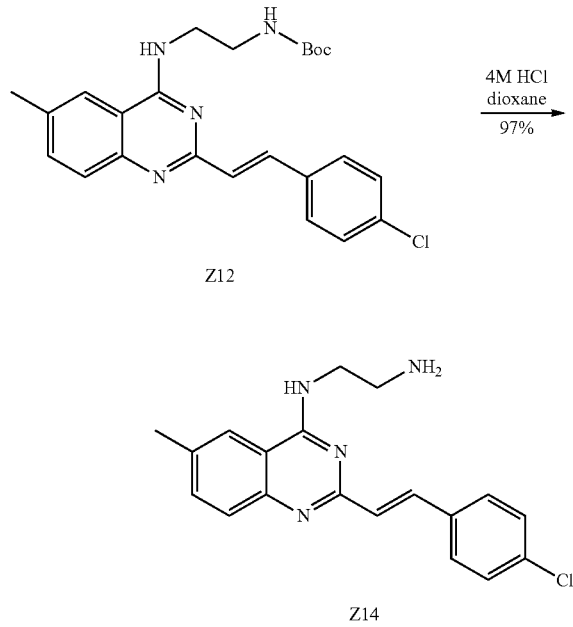

Z12

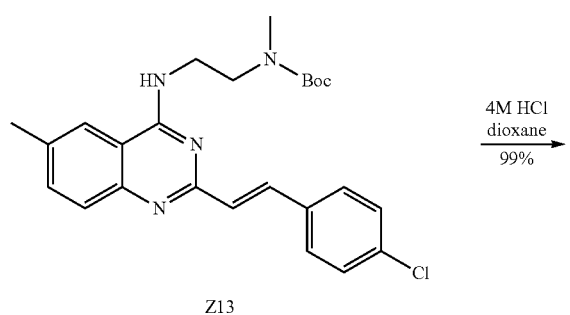

Z13

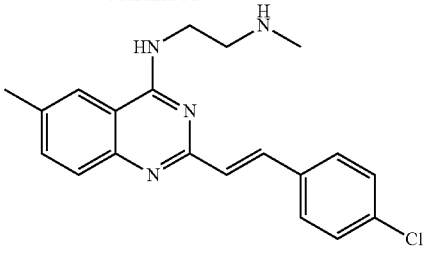

Z15

(E)-N$^1$-(2-(4-chlorostyryl)-6-methylquinazolin-4-yl)-N$^2$-methylethane-1,2-diamine (Z15)—Z13 was dissolved in 4 M HCl in dioxane and heated at 40° C. After stirring for 1 h, the reaction mixture was basified with 10% NaOH and extracted with EtOAc. Organic layer was ashed with brine, dried over Na$_2$SO$_4$, and evaporated. Residue was purified by silica gel chromatography (90:9:1 CH$_2$Cl$_2$:CH$_3$OH:NH$_4$OH) to give Z15 as a white solid (76.4 mg, 99%). $^1$H NMR (500 MHz, Methanol-$d_4$) δ 7.91 (d, J=15.7 Hz, 1H), 7.80 (s, 1H), 7.62-7.51 (m, 4H), 7.35 (d, J=8.5 Hz, 2H), 7.04 (d, J=16.0 Hz, 1H), 3.87 (t, J=6.4 Hz, 2H), 2.97 (t, J=6.3 Hz, 2H), 2.49 (s, 3H), 2.47 (s, 3H). $^{13}$C NMR (126 MHz, CD$_3$OD) δ 161.00, 160.81, 148.67, 137.19, 137.09, 136.46, 135.63, 135.43, 129.95, 129.81, 129.45, 127.35, 122.60, 115.25, 51.39, 40.92, 35.88, 21.64. HRMS (ESI) m/z: [M+H]$^+$ Calcd for $C_{20}H_{22}N_4Cl$ 353.1533; Found 353.1524.

Z14 → (Ac$_2$O, Et$_3$N, CH$_2$Cl$_2$, 76%) → Z16

(E)-N$^1$-(2-(4-chlorostyryl)-6-methylquinazolin-4-yl)ethane-1,2-diamine (Z14)—Z12 was dissolved in 4 M HCl in dioxane and heated to 40° C. After stirring for 1 h, reaction was basified with 10% NaOH and extracted with EtOAc. Organic layer was washed with brine, dried over Na$_2$SO$_4$, and evaporated. Residue was purified by silica gel chromatography (90:9:1 CH$_2$Cl$_2$:CH$_3$OH:NH$_4$OH) to give Z14 as a white solid (52.5 mg, 97%). $^1$H NMR (500 MHz, CD$_3$OD) δ 7.84 (d, J=15.8 Hz, 1H), 7.76 (s, 1H), 7.52 (dd, J=8.6, 6.3 Hz, 4H), 7.30 (d, J=8.1 Hz, 2H), 6.99 (d, J=15.8 Hz, 1H), 3.78 (t, J=6.4 Hz, 2H), 3.01 (t, J=6.4 Hz, 2H), 2.44 (s, 3H). $^{13}$C NMR (126 MHz, CD$_3$OD) δ 160.95, 160.82, 148.61, 137.07, 136.97, 136.41, 135.52, 135.33, 129.87, 129.76, 129.43, 127.30, 122.55, 115.21, 44.30, 41.81, 21.66. HRMS (ESI) m/z: [M+H]$^+$ Calcd for $C_{19}H_{20}N_4Cl$ 339.1376; Found 339.1375.

(E)-N-(2-((2-(4-chlorostyryl)-6-methylquinazolin-4-yl)amino)ethyl)acetamide (Z16)—To a stirring solution of Z14 (27.4 mg, 0.081 mmol) in CH$_2$Cl$_2$ (1.0 mL) was added triethylamine (15 μL, 0.11 mmol) followed by acetic anhydride (10 μL, 0.11 mmol). After stirring at room temperature for 1 h, reaction mixture was quenched with the addition of satd aq NH$_4$C$_1$ and extracted with EtOAc. Organic layer was washed with brine, dried over Na$_2$SO$_4$, and evaporated. Residue was purified by silica gel chromatography (2-5% CH$_3$OH:CH$_2$Cl$_2$) to give Z16 as a white solid (23.9 mg, 76%). $^1$H NMR (500 MHz, CDCl$_3$+MeOD) δ 7.92 (dq, J=14.8, 4.5 Hz, 1H), 7.75-7.68 (m, 1H), 7.64 (dd, J=8.4, 2.2 Hz, 1H), 7.57 (s, 3H), 7.41-7.33 (m, 2H), 7.11 (dd, J=15.8, 2.3 Hz, 1H), 3.91-3.82 (m, 2H), 3.62-3.55 (m, 2H), 2.52 (s, 3H), 1.96 (s, 2H). $^{13}$C NMR (126 MHz, CDCl$_3$+MeOD) δ 172.56, 159.51, 159.30, 147.30, 136.03, 135.78, 134.73, 134.38, 128.84, 128.53, 128.32, 126.54, 121.03, 113.74, 41.25, 40.10, 22.49, 21.34. HRMS (ESI) m/z: [M+H]$^+$ Calcd for C$_{21}$H$_{22}$N$_4$OCl 381.1482; Found 381.1477

The synthesis of analogous compounds is described in Anderson et al., *ACS Chem. Biol.* 7, 1918-1928 (2012); and Epomuceno et al., *ACS Med. Chem. Lett.* 6, 308-312 (2015).

Example 3-1: Preparation of Exemplary Ribocil C Derivatives

General Methods and Materials. All reactions were carried out under an atmosphere of N$_2$ using oven or flame dried glassware and standard syringe/septa techniques. Unless noted, all commercial reagents and solvents were used without further purification. Flash column chromatography was performed on 230-430 mesh silica gel. Analytical thin layer chromatography was performed with pre-coated, glass-baked plates (250μ) and visualized by fluorescence or charring with potassium permanganate stain. $^1$H NMR and $^{13}$C NMR spectra were recorded on Oxford 400 MHz/500 MHz spectrometers. Chemical shifts for starting materials and products were reported relative to tetramethyl silane (0.00 ppm) or D$_2$O (4.79 ppm) for $^1$H-NMR and CDCl$_3$ (77.0 ppm) for $^{13}$C-NMR data. Data are presented as follows: chemical shift (ppm), multiplicity (s=singlet, d=doublet, t=triplet, dd=doublet of doublets, m=multiplet, br=broad), coupling constant J (Hz) and integration. ESI-MS spectra were collected using a Waters GCT premier QTOF in the positive ion mode.

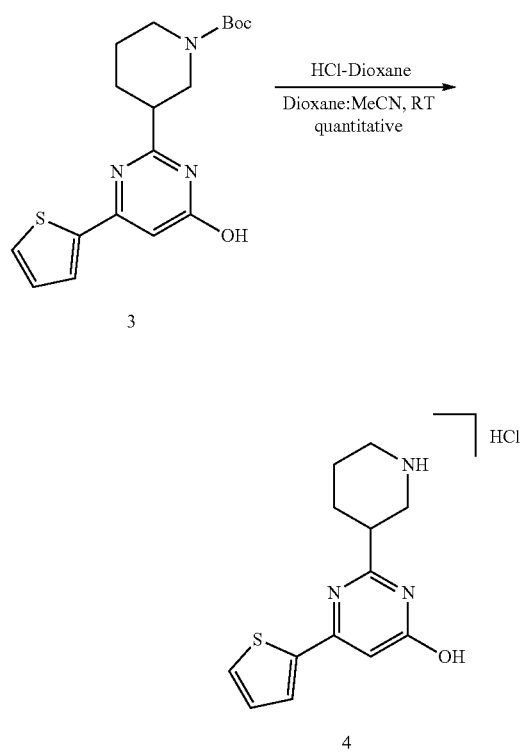

Scheme 6. Synthesis of Fragment 4.

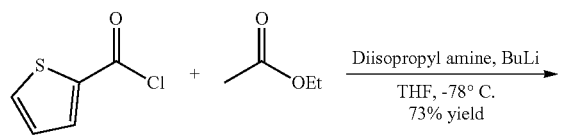

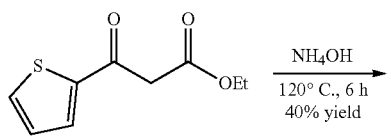

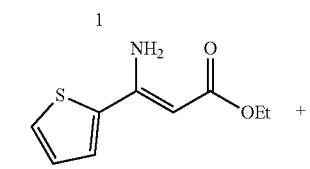

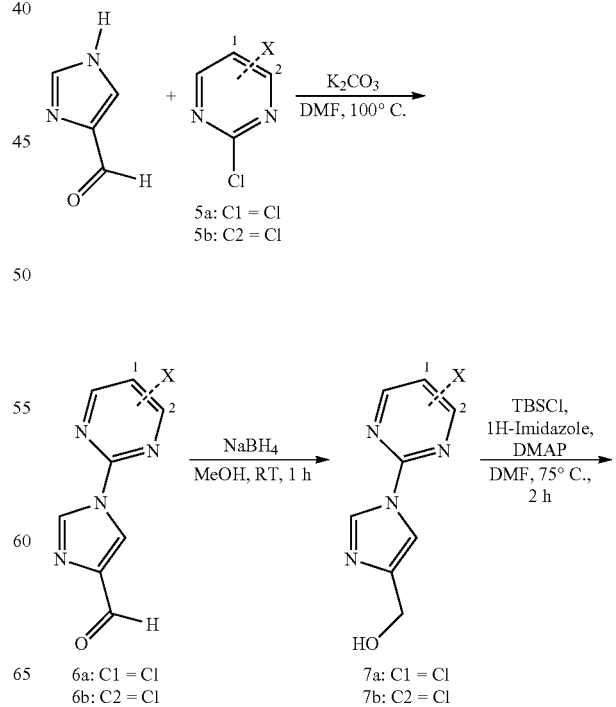

-continued
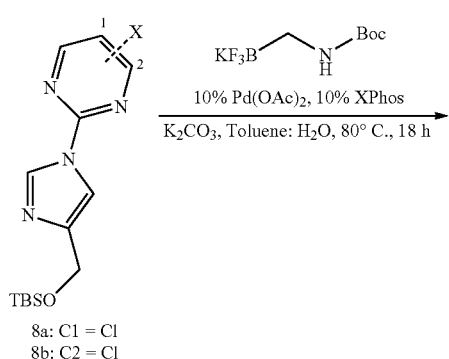
8a: C1 = Cl
8b: C2 = Cl
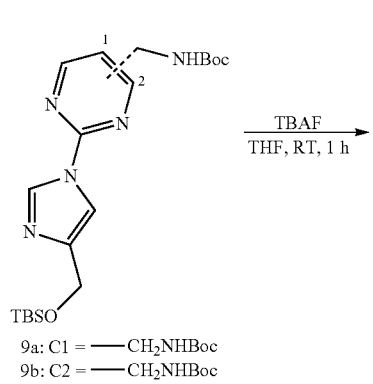
9a: C1 = —CH₂NHBoc
9b: C2 = —CH₂NHBoc
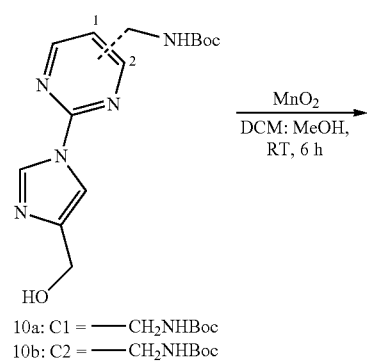
10a: C1 = —CH₂NHBoc
10b: C2 = —CH₂NHBoc
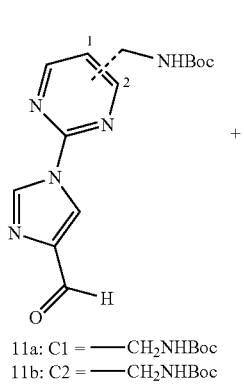 +
11a: C1 = —CH₂NHBoc
11b: C2 = —CH₂NHBoc
-continued
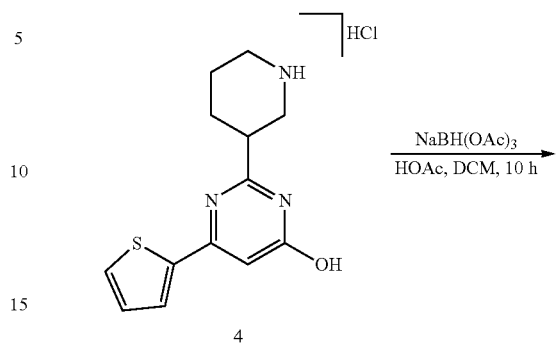
4
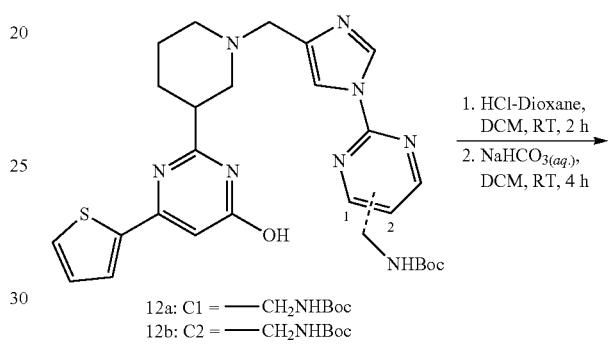
12a: C1 = —CH₂NHBoc
12b: C2 = —CH₂NHBoc
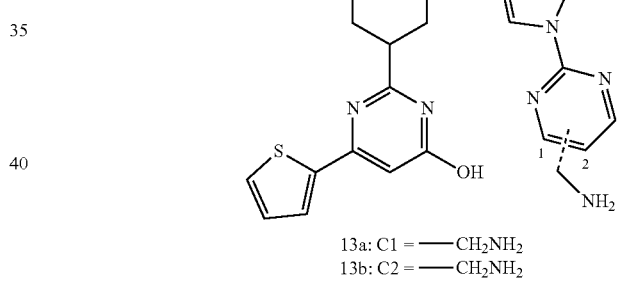
13a: C1 = —CH₂NH₂
13b: C2 = —CH₂NH₂
Scheme 8. Synthesis of Methyl Amine Derivative 18.
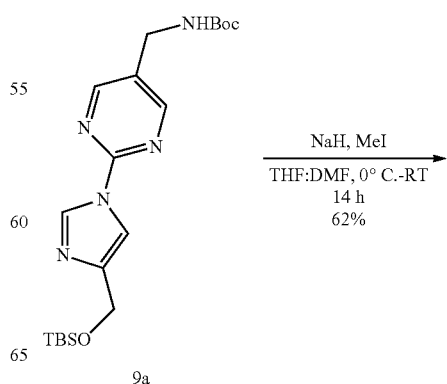
9a

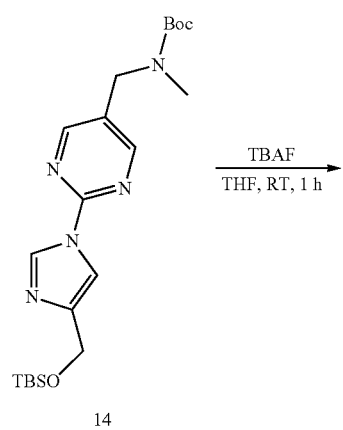

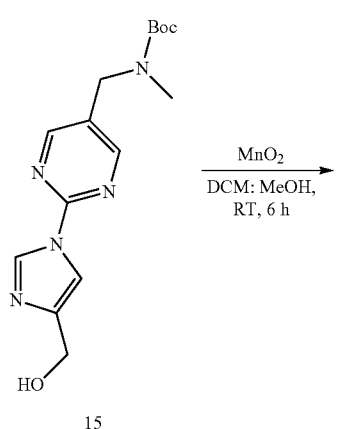

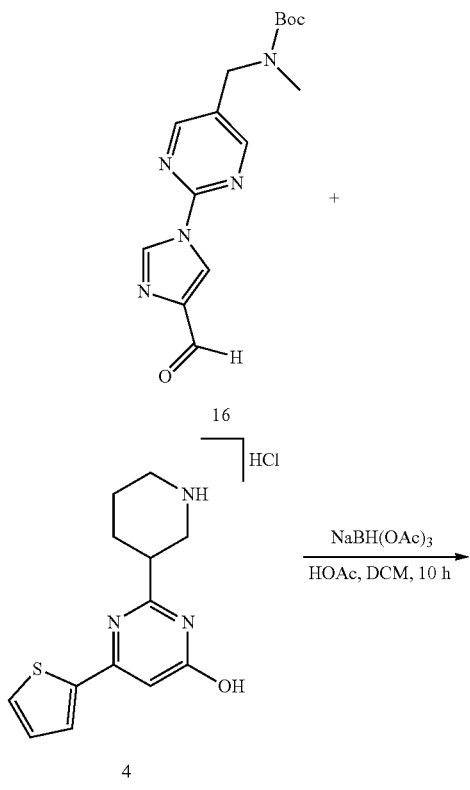

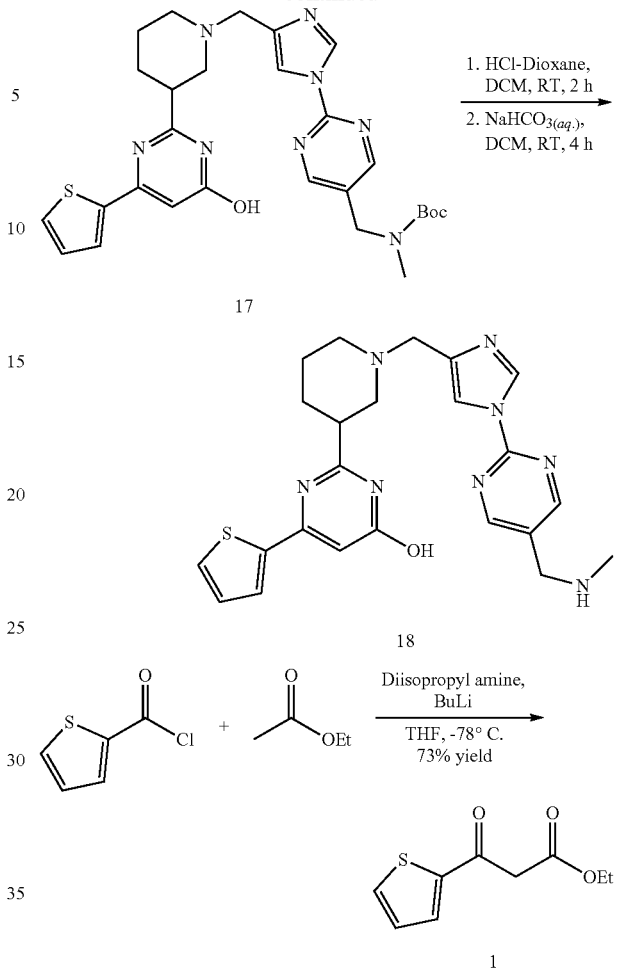

To a flame dried flask containing diisopropyl amine (135 mmol, 2.1 equiv.) in 123 mL THF (0.5 M) at −78° C. was added 76 mL 1.6 M nBuLi (125, 2.0 equiv.) dropwise. After stirring for 30 minutes at this temperature, 6 mL ethyl acetate (75 mmol, 1.15 equiv.) was added to the reaction and stirred at −78° C. for 15 minutes. 9 g of 2-thiphenecarbonyl chloride (65 mmol, 1.0 equiv.) was then added to the reaction mixture and stirred at the same temperature for ~2 hours. Upon completion, aqueous NH$_4$C$_1$ was then added and the crude mixture was extracted using ethyl acetate. The organic layers were then washed with water and brine followed by drying over Na$_2$SO$_4$. The solution was filtered and the organics were concentrated via rotary-evaporation. The crude mixture was then purified using silica gel column chromatography (1:8 Ethyl Acetate:Hexanes to 1:2 Ethyl Acetate:Hexanes) to give 9.5 g (73% yield) of the desired keto-ester as a red oil in.

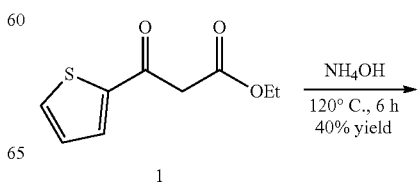

-continued

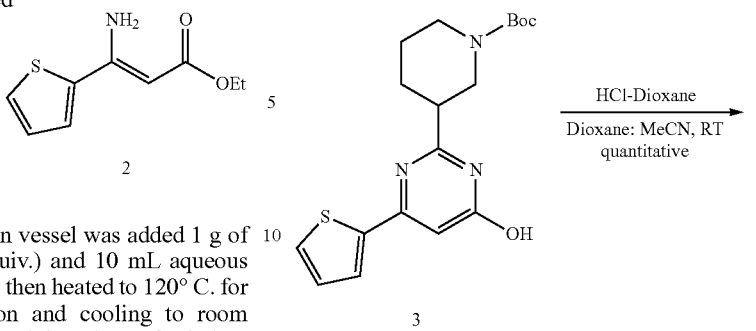

To a high pressure rated reaction vessel was added 1 g of the keto-ester 1 (5 mmol, 1.0 equiv.) and 10 mL aqueous NH₄OH (0.5 M). The reaction was then heated to 120° C. for 6 hours. Upon reaction condition and cooling to room temperature, the desired product precipitated out of solution, at which point it was filtered away and dried under reduced pressure. This provided the desired product in roughly 40% yield. The off-white solid obtained was then submitted to the following reaction conditions without further purification.

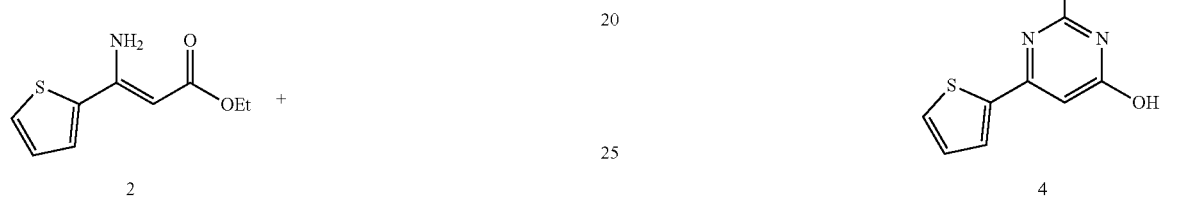

To a flask containing 300 mg of piperidine 3 (0.83 mmol, 1.0 equiv.) in 3.3 mL of a 4:1 mixture of dioxane:acetonitrile (0.25 M) was added 2 mL of 4.0 M HCl-dioxane (8 mmol, 2.0 equiv.). This then stirred for 2 hours at room temperature followed by concentration via rotary-evaporation. The crude product was then directly submitted to the reductive amination reaction to yield the coupled products as described below.

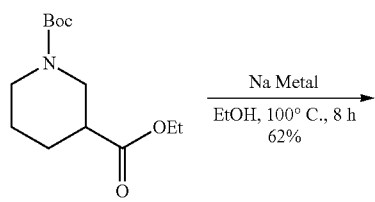

To a high pressure rated reaction vessel was added 670 mg Na metal (30 mmol, 5 equiv.) and 25 mL EtOH (0.25 M). Upon complete consumption of the Na metal (no further gas evolution), 1.2 g enamine 2 (6 mmol, 1.0 equiv.) and 1.45 g of methyl N-Boc-piperidine-3-carboxylate (6 mmol, 1.0 equiv.) were added to the solution which was then heated to 100° C. for 5 hours. The tube was sealed and heated at 100° C. for 5 hr. The reaction was then concentrated and redissolved in water. The aqueous layer was acidified to pH ~4 and extracted with a mixture of EtOAc-THF (1:1) The combined organic layer was dried over Na₂SO₄, filtered and concentrated. The crude material was then purified using silica gel column chromatography (1:2 Ethyl Acetate: Hexanes to 4:1 Ethyl Acetate:Hexanes) to give 650 mg of the desired product as a white solid in 62% yield.

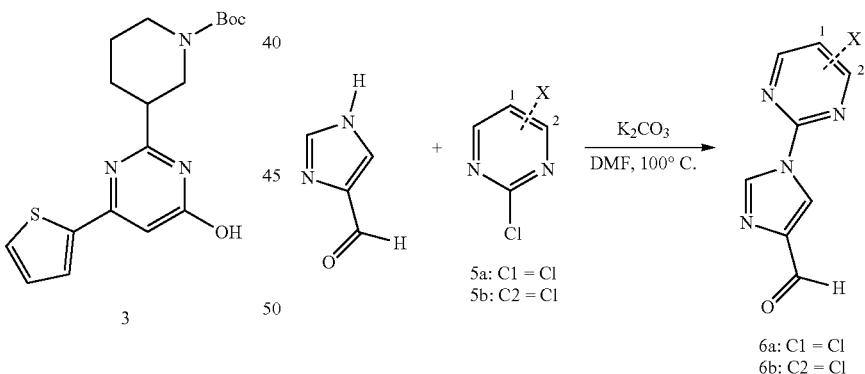

To a flask containing 1H-imidazole-4-carbaldehyde (20 mmol, 1.0 equiv.) and 1,4/1,5-dichloropyrimidine (22 mmol, 1.1 equiv.) was added 40 mL DMF (0.5 M). This solution was then heated to 100° C. and stirred for approximately 2 hours while being monitored by TLC. Upon reaction completion, the reaction mixture was diluted with dichloromethane and washed with water and brine. The organic layers were then combined, dried over Na₂SO₄ and concentrated via rotary-evaporation. The crude mixture was then dissolved in a minimal amount of dichloromethane and hexanes was added to the solution to precipitate the final product. The solid was then filtered and dried under vacuum and submitted to the next reduction reaction without any further purification. Reaction yields for the 1,5-pyrimidine were 85% while the yield for the 1,4-pyrimidine was around 40% due to an undesired regioisomer being formed.

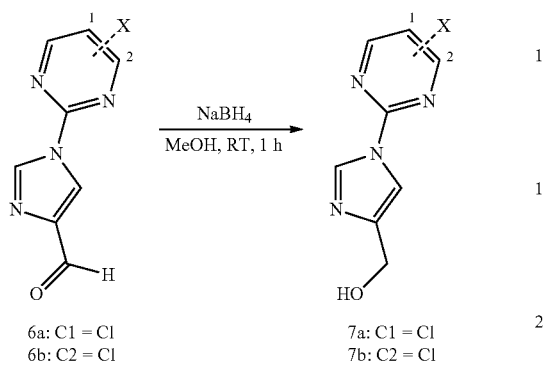

6a: C1 = Cl
6b: C2 = Cl

7a: C1 = Cl
7b: C2 = Cl

To a flask containing imidazole-pyrimidine 6a or 6b (10 mmol, 1.0 equiv.) was added 100 mL methanol (0.1 M). NaBH₄ (3 mmol, 0.3 equiv.) was then added in 3 portions. Upon reaction completion as determined by TLC, the crude reaction mixture was quenched with water. The crude reaction mixture was then extracted using dichloromethane. The organics were collected and dried over Na₂SO₄ followed by concentration via rotary-evaporation. The crude material was then purified using silica gel column chromatography (10% MeOH:Chloroform) to yield the primary alcohol as a white solid. Yields for this reaction were between 70-80%.

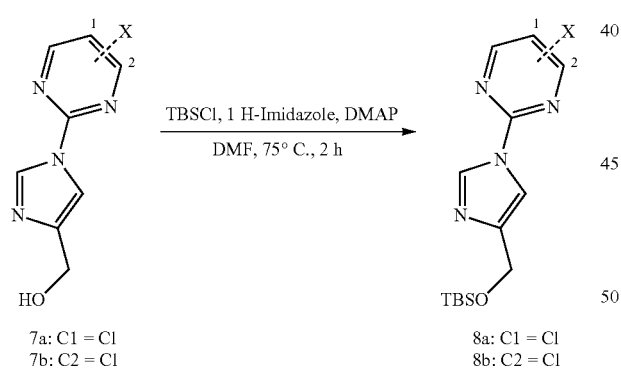

7a: C1 = Cl
7b: C2 = Cl

8a: C1 = Cl
8b: C2 = Cl

To a flask containing imidazole-pyrimidine 7a or 7b (5 mmol, 1.0 equiv.) in 10 mL DMF (0.5 M) was added 1H-imidazole (5 mmol, 1 equiv.) TBSCl (5.5 mmol, equiv.) and DMAP (1 mmol, 0.2 equiv.). This solution was then heated to 75° C. and stirred for 2 hours. Upon completion as determined by TLC, the crude mixture was diluted with ethyl acetate and washed with water and brine. The organic layer was then collected and dried over Na₂SO₄ followed by filtration and concentration via rotary-evaporation. The crude material was then purified using silica gel column chromatography (1:1 Ethyl Acetate:Hexanes to 5:1 Ethyl Acetate:Hexanes) to yield the silyl-protected product as a white solid (70-80% yield).

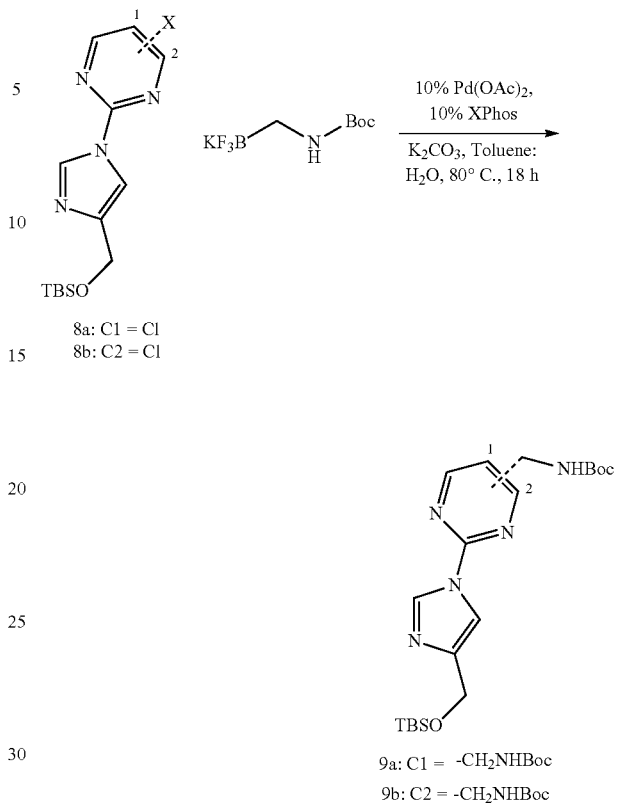

8a: C1 = Cl
8b: C2 = Cl

9a: C1 = -CH₂NHBoc
9b: C2 = -CH₂NHBoc

To a N₂ purged flask containing O-Silyl imidazole 8a or 8b (2.0 mmol, 1.0 equiv.), Pd(OAc)₂ (0.2 mmol, 0.1 eq.), XPhos (0.2 mmol, 0.1 eq.), tert-butoxycarbonyl)amino)methyl) trifluoroborate (2.2 mmol, 1.1 eq.) and K₂CO₃ (6 mmol, 3.0 equiv.) was added 6 mL degassed toluene and 1.5 mL degassed water. The reaction was then heated to 75° C. for 18 hours. Upon completion, the reaction was diluted with ethyl acetate and washed with water and brine. The organic layer was then collected and dried over Na₂SO₄ followed by filtration and concentration via rotary-evaporation. The crude material was then purified using silica gel column chromatography (2:1 Ethyl Acetate:Hexanes to 10:1 Ethyl Acetate:Hexanes) to yield the Boc-protected amino-product as a white solid (50-60% yield).

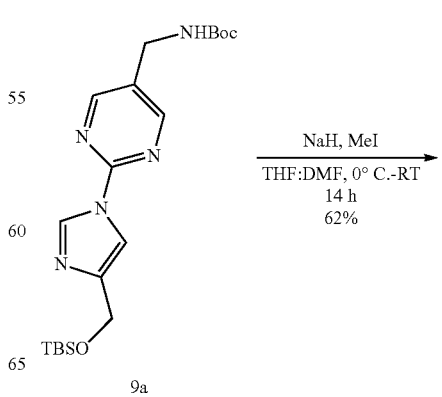

9a

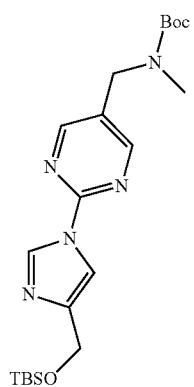

14

To a flame dried flask containing 9a (1 mmol, 1.0 equiv.) in 5 mL DMF (0.2 M) was added NaH (3 mmol, 3 equiv.) at 0° C. This stirred for 1 hour at this temperature followed by the addition of MeI (1.1 mmol, 1.1 equiv.) and DMF (1.0 mmol, 1.0 equiv). This stirred at 0° C. for another 2 hours followed by warming to room temperature and stirring overnight. Upon completion, water was added to the reaction and the mixture was extracted with ethyl acetate. The organic layer was then collected and dried over Na$_2$SO$_4$ followed by filtration and concentration via rotary-evaporation. The crude material was then purified using silica gel column chromatography (1:1 Ethyl Acetate:Hexanes to 5:1 Ethyl Acetate:Hexanes) to yield the N-methylated product 14 in 45% yield as a white solid.

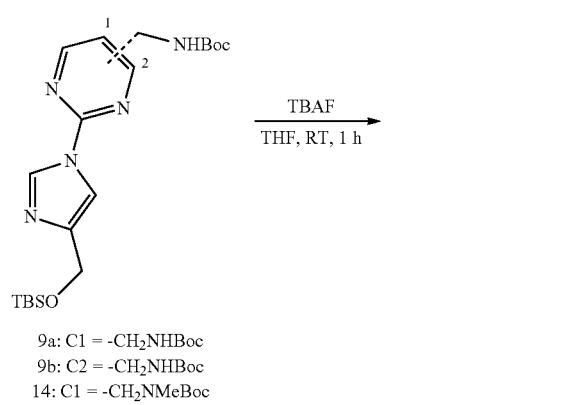

9a: C1 = -CH$_2$NHBoc
9b: C2 = -CH$_2$NHBoc
14: C1 = -CH$_2$NMeBoc

TBAF
THF, RT, 1 h

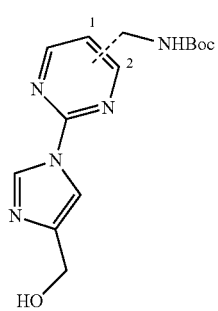

10a: C1 = -CH$_2$NHBoc
10b: C2 = -CH$_2$NHBoc
15: C1 = -CH$_2$NMeBoc

To a flask containing imidazole 9a, 9b or 14 (1.0 mmol, 1.0 equiv.) in 5 mL THF (0.2 M) was added tetrabutylammoniumfluroide (1.1 mmol, 1.1 equiv.). The reaction stirred at room temperature and monitored using TLC. Upon reaction completion, the crude mixture was washed with water and brined. The organic layer was then collected and dried over Na$_2$SO$_4$ followed by filtration and concentration via rotary-evaporation. The crude material was then directly submitted to the following oxidation reaction.

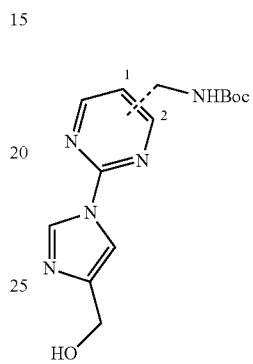

MnO$_2$
DCM:MeOH, RT, 6 h

10a: C1 = -CH$_2$NHBoc
10b: C2 = -CH$_2$NHBoc
15: C1 = -CH$_2$NMeBoc

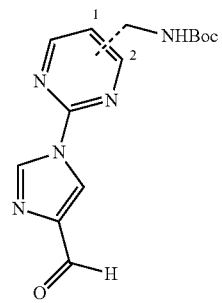

11a: C1 = -CH$_2$NHBoc
11b: C2 = -CH$_2$NHBoc
16: C1 = -CH$_2$NMeBoc

To a flask containing imidazole 10a, 10b or 15 (0.5 mmol, 1.0 equiv.) in 5 mL of a mixture of 1:1 dichloromethane: methanol (0.1 M) was added MnO$_2$ (5 mmol, 10 equiv.). The reaction stirred at room temperature for 6 hours, at which point all starting material was consumed by TLC analysis. Upon reaction completion, the crude mixture was filtered through a pad of celite and concentrated via rotary-evaporation. The crude material was then purified using silica gel column chromatography (1:4 Ethyl Acetate:Hexanes to 1:1 Ethyl Acetate:Hexanes) to yield the desired aldehyde as a white solid (70-80% yield).

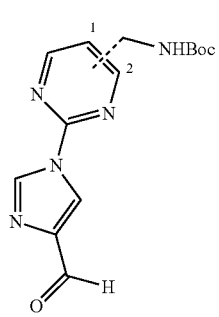

11a: C1 = -CH₂NHBoc
11b: C2 = -CH₂NHBoc
16: C1 = -CH₂NMeBoc

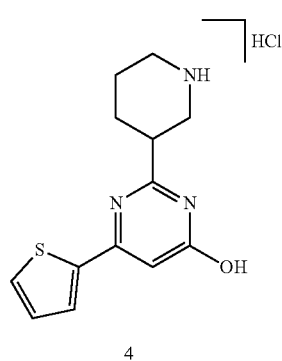

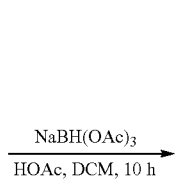

4

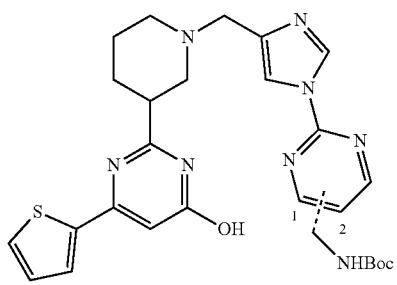

12a: C1 = -CH₂NHBoc
12b: C2 = -CH₂NHBoc
17: C1 = -CH₂NMeBoc

To a flask containing imidazole 11a, 11b or 16 (0.25 mmol, 1.1 equiv.) and fragment X (0.22 mmol, 1.0 equiv.) in 1 mL of dichloromethane (0.2 M) was added acetic acid (pH-5). This stirred for 2 hours at room temperature followed by the addition of NaBH(OAc)₃ (0.3 mmol, 1.35 equiv.). The reaction was then run overnight followed by being quenched with NaHCO₃ upon completion. The crude mixture was extracted with dichloromethane and the organic layers were collected and dried over NaSO₄. The solution was then filtered and the organics were concentrated via rotary evaporation. The crude reaction material was then submitted to the next reaction conditions without further purification.

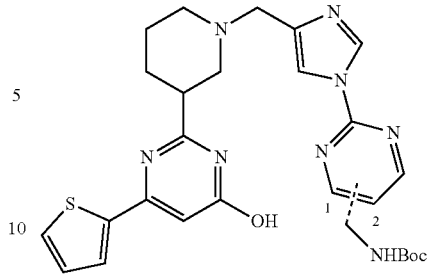

12a: C1 = -CH₂NHBoc
12b: C2 = -CH₂NHBoc
17: C1 = -CH₂NMeBoc

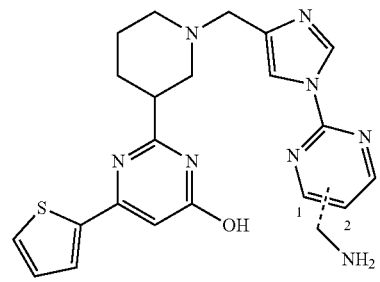

13a: C1 = -CH₂NH₂
13b: C2 = -CH₂NH₂
18: C1 = -CH₂NHME

To a flask containing Boc-protected amino-imidazole 12a, 12b or 17 (0.1 mmol, 1 equiv.) in 1 mL dichloromethane (0.1 M) was added a solution of 4.0 M HCl-dioxane. This stirred at room temperature for 2 hours. Upon completion dichloromethane was added to the solution followed by the addition of aqueous NaHCO₃. This stirred for 4 hours at room temperature followed by extraction with dichloromethane. The organic layer was dried over Na₂SO₄ and concentrated using rotary-evaporation. The crude reaction mixtures were then purified using reverse phase preparative HPLC to give the desired products as a white solid.

NMR Data

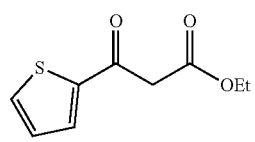

1

¹H-NMR (500 MHz, CDCl₃): δ (ppm) 1.26 (3H, t, J=7.1 Hz), 3.92 (2H, s), 4.21 (2H, q, J=7.1 Hz), 7.15 (1H, dd, J=5.0, 3.8 Hz), 7.74-7.69 (2H, m).

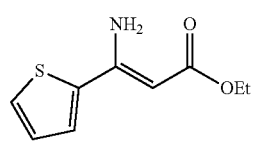

2

¹H-NMR (500 MHz, DMSO-d₆): δ (ppm) 4.94 (1H, s), 7.10 (1H, dd, J=5.0, 3.7 Hz), 7.48 (1H, dd, J=3.7, 1.2 Hz), 7.57 (1H, dd, J=5.0, 1.2 Hz).

107
3
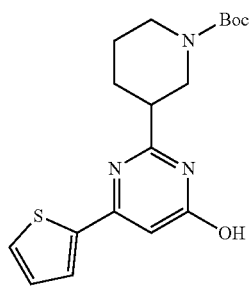
¹H-NMR (500 MHz, CDCl₃): δ 1.45 (9H, s), 1.76-1.56 (3H, m), 1.91-1.78 (1H, m), 2.18-2 (1H, m), 2.43-2.54 (2H, m), 2.7-2.96 (2H, m), 6.63 (1H, s), 7.14 (1H, dd, J=5.0, 3.8 Hz), 7.52 (1H, d, J=5.0 Hz), 7.68 (1H, dd, J=3.8, 1.2 Hz)
6a
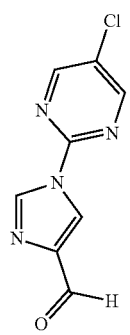
¹H NMR (500 MHz, DMSO-d₆) δ 9.87 (s, 1H), 9.08 (s, 2H), 8.73 (s, 2H).
6b
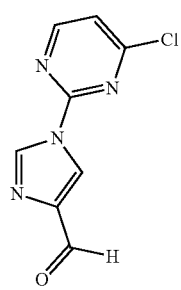
¹H NMR (500 MHz, DMSO-d₆) δ 9.86 (s, 1H), 8.97 (d, J=5.6 Hz, 1H), 8.90 (d, J=1.2 Hz, 1H), 8.85 (d, J=1.3 Hz, 1H), 8.13 (d, J=5.6 Hz, 1H).
108
7a
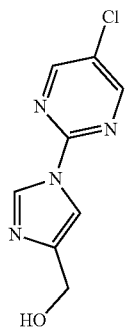
¹H NMR (500 MHz, DMSO-d₆) δ 8.98 (s, 2H), 8.48 (s, 1H), 7.70 (s, 1H), 5.09 (t, J=5.6 Hz, 1H), 4.42 (d, J=5.5 Hz, 2H).
7b
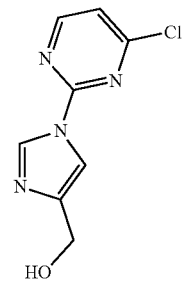
¹H NMR (500 MHz, DMSO-d₆) δ 8.84 (d, J=5.6 Hz, 1H), 8.62 (s, 1H), 7.97 (d, J=5.7 Hz, 1H), 7.83 (s, 1H), 4.46-4.37 (s, 2H).
8a
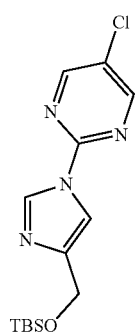
¹H NMR (500 MHz, CDCl₃) δ 8.62 (s, 2H), 8.49 (d, J=1.4 Hz, 1H), 7.72 (q, J=1.2 Hz, 1H), 4.74 (s, 2H), 0.95 (s, 9H), 0.13 (s, 6H).

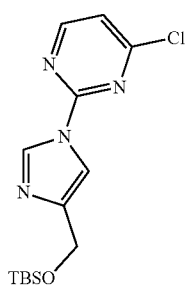
8b
¹H NMR (500 MHz, CDCl₃) δ 8.64 (d, J=5.5, 0.7 Hz, 1H), 8.41 (s, 1H), 7.49 (s, 1H), 7.21 (d, J=5.6 Hz, 1H), 4.74 (s, 2H), 0.94 (s, 9H), 0.13 (s, 6H).
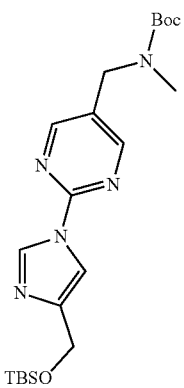
14
¹H NMR (500 MHz, CDCl₃) δ 8.58 (s, 2H), 8.54 (s, 1H), 7.76 (s, 1H), 4.75 (s, 1H), 2.87 (s, 3H), 0.95 (s, 9H), 0.13 (s, 6H).
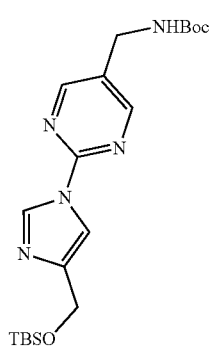
9a
¹H NMR (500 MHz, CDCl₃) δ 8.60 (s, 2H), 8.52 (s, 1H), 7.75 (s, 1H), 4.74 (s, 2H), 4.31 (s, 2H), 1.45 (s, 9H), 0.95 (s, 9H), 0.16-0.11 (s, 6H).
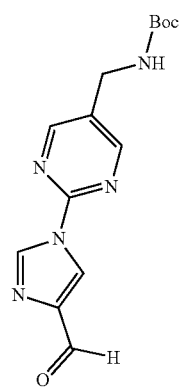
11a
¹H NMR (400 MHz, CDCl₃) δ 9.98 (s, 1H), 8.70 (s, 2H), 8.68 (s, 1H), 8.54 (s, 1H), 4.36 (d, J=6.2 Hz, 2H), 1.46 (s, 9H),
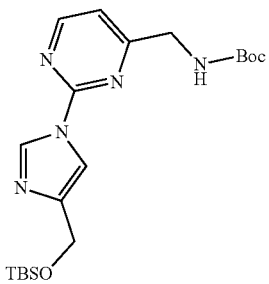
9b
¹H NMR (500 MHz, CDCl₃) δ 8.75 (d, J=5.1, 0.7 Hz, 1H), 8.52 (s, 1H), 7.49 (s, 1H), 7.28 (d, J=5.1 Hz, 1H), 4.74 (s, 2H), 4.34 (s, 2H), 1.43 (s, 9H), 0.93 (s, 9H), 0.14 (s, 6H).
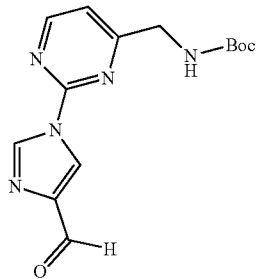
11b
¹H NMR (500 MHz, CDCl₃) δ 9.99 (s, 1H), 8.86 (d, J=5.5 Hz, 1H), 8.54 (s, 1H), 8.38 (s, 1H), 7.30 (d, J=5.5 Hz, 1H), 4.63 (d, J=5.8 Hz, 2H), 1.49 (s, 9H).

111

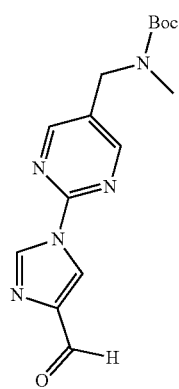

16

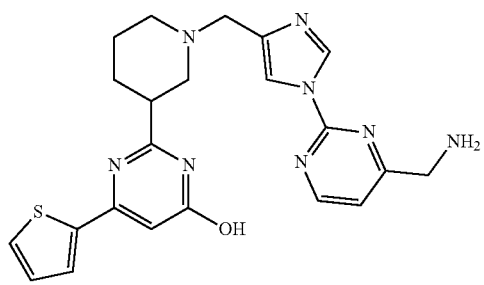

¹H NMR (500 MHz, DMSO-d₆) δ 8.82 (d, J=5.7 Hz, 1H), 8.68 (d, J=1.9 Hz, 1H), 7.94 (s, 1H), 7.82 (d, J=3.6 Hz, 1H), 7.75-7.70 (m, 2H), 7.17-7.13 (m, 1H), 6.64 (d, J=1.9 Hz, 1H), 3.86 (s, 2H), 3.49 (s, 2H), 2.98 (d, J=10.5 Hz, 1H), 2.85-2.76 (m, 2H), 2.36-2.30 (m, 1H), 2.10 (s, 1H), 1.87 (d, J=11.2 Hz, 1H), 1.70 (d, J=12.0 Hz, 1H), 1.58-1.52 (m, 2H). HRMS Calculated for $C_{22}H_{24}N_8OS$ [M+H]⁺: 449.1867, Found: 449.1874.

¹H NMR (400 MHz, CDCl₃) δ 9.93 (s, 1H), 8.67-8.59 (m, 3H), 8.53 (d, J=1.2 Hz, 1H), 4.43 (s, 2H), 2.88 (s, 3H), 1.45 (s, 9H).

12a

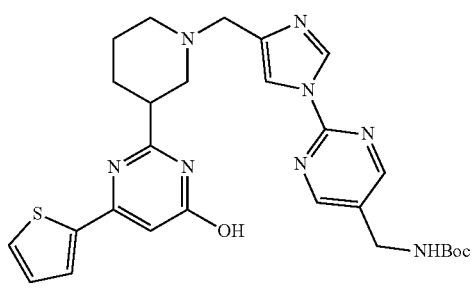

18

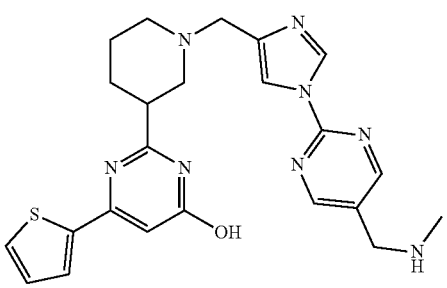

1H NMR (500 MHz, DMSO-d₆) δ 8.69 (s, 2H), 8.48 (s, 1H), 7.82 (d, J=3.6 Hz, 1H), 7.74-7.70 (d, J=3.6 Hz, 1H), 7.50 (t, J=5.9 Hz, 1H), 7.15 (t, J=3.7 Hz, 1H), 6.64 (s, 1H), 4.16 (d, J=5.9 Hz, 2H), 3.56 (s, 2H), 3.02 (d, J=10.9 Hz, 1H), 2.90-2.71 (m, 2H), 2.31 (d, J=11.0 Hz, 1H), 2.10 (m, 1H), 1.87 (d, J=9.6 Hz, 1H), 1.75-1.63 (m, 1H), 1.53 (m, 2H), 1.37 (s, 9H). HRMS Calculated for $C_{27}H_{32}N_8O_3S$ [M+H]⁺: 549.2391, Found: 549.2376.

¹H NMR (500 MHz, DMSO-d₆) δ 8.74 (s, 2H), 8.48 (s, 1H), 7.82 (d, J=3.8 Hz, 1H), 7.77 (s, 1H), 7.72 (d, J=5.1 Hz, 1H), 7.15 (t, J=4.7 Hz, 1H), 6.64 (s, 1H), 3.66 (s, 2H), 3.50 (d, J=5.5 Hz, 2H), 3.01 (d, J=11.1 Hz, 1H), 2.84-2.77 (m, 2H), 2.32 (d, J=13.9 Hz, 1H), 2.25 (s 3H), 2.11 (d, J=10.5 Hz, 1H), 1.88 (d, J=11.1 Hz 1H), 1.71 (d, J=10.5 Hz 1H), 1.53 (m, J=9.8 Hz, 2H). HRMS Calculated for $C_{23}H_{26}N_8OS$ [M+H]⁺: 463.2023, Found: 463.2018.

13a

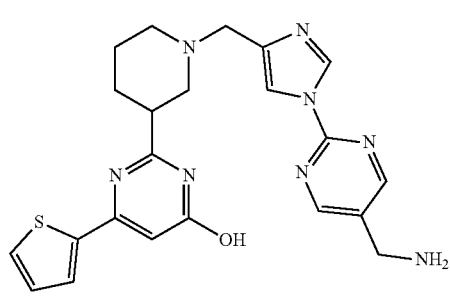

Ribocil C

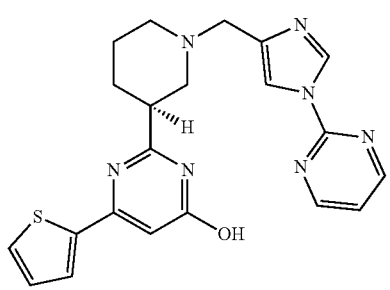

¹H NMR (500 MHz, DMSO-d₆) δ 8.78 (s, 2H), 8.49 (s, 1H), 7.83 (d, J=3.7 Hz, 1H), 7.79 (s, 1H), 7.73 (d, J=5.0 Hz, 1H), 7.17 (t, J=4.4 Hz, 1H), 6.65 (s, 1H), 3.77 (s, 2H), 3.51 (d, J=5.7 Hz, 2H), 3.03 (d, J=10.7 Hz, 1H), 2.93-2.72 (m, 2H), 2.33 (t, J=11.3 Hz, 1H), 2.10 (d, J=10.7 Hz, 1H), 1.88 (d, J=11.2 Hz, 1H), 1.71 (d, J=11.2 Hz, 1H), 1.61-1.48 (m, 2H). HRMS Calculated for $C_{22}H_{24}N_8OS$ [M+H]⁺: 449.1867, Found: 449.1865.

¹H-NMR (500 MHz, DMSO-d₆): δ (ppm) 1.56-1.50 (2H, m), 1.72 (1H, m), 1.86 (1H, d, J=8.4 Hz), 2.11 (1H, m), 2.33 (1H, m), 2.79 (1H, m), 2.83 (1H, d, J=12 Hz), 3.02 (1H, d, J=11 Hz), 3.54-3.47 (2H, m), 6.63 (1H, s), 7.16 (1H, dd, J=5.0, 3.7 Hz), 7.46 (1H, t, J=4.9 Hz), 7.71 (1H, dd, J=5.0, 1.1 Hz), 7.84-7.80 (2H, m), 8.50 (1H, d, J=1.3 Hz), 8.85 (2H, d, J=4.9 Hz), 12.34 (1H, s). HRMS Calculated for $C_{22}H_{24}N_8OS$ [M+H]⁺: 420.1601, Found: 420.1611

Example 3-2: Exemplary Ribocil C Derivatives

The following Ribocil C derivatives were or can be prepared using the procedures described herein, including derivatives having the (S)- or (R)-configuration.

1

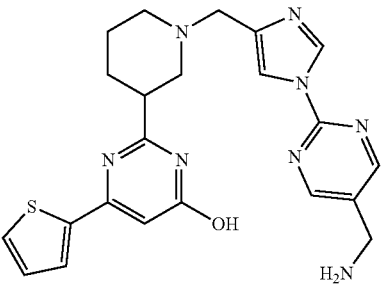

MIC DATA (g/mL)
S. aureus ATCC 29213: 16
E. coli MC-1655: 16
E. Coli TolC: 2
E. Coli. rfaC: 8

2

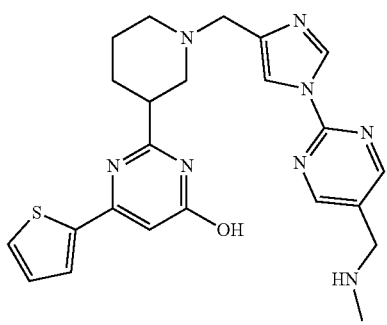

MIC DATA (g/mL)
S. aureus ATCC 29213: 4
E. coli MC-1655: 16
E. Coli TolC: 2
E. Coli. rfaC: 8

3

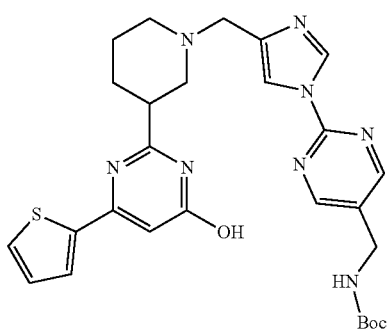

MIC DATA (g/mL)
S. aureus ATCC 29213: >256
E. coli MC-1655: >256

4

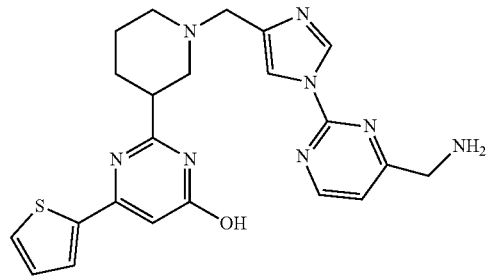

MIC DATA (g/mL)
S. aureus ATCC 29213: 64
E. coli MC-1655: 64

High Accumulator(nmols/1012 CFUs):
3435 470

5

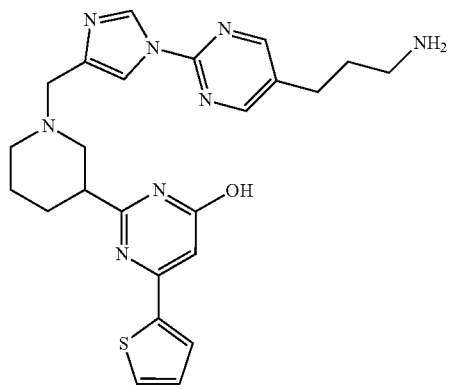

2
64

6

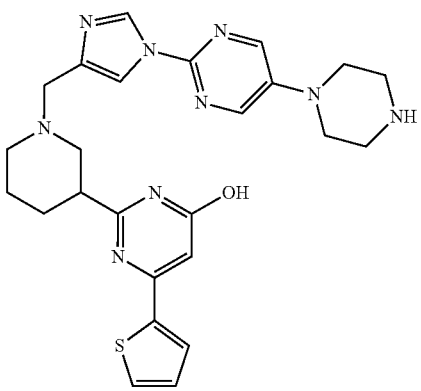

0.5
64

115
-continued
116
-continued
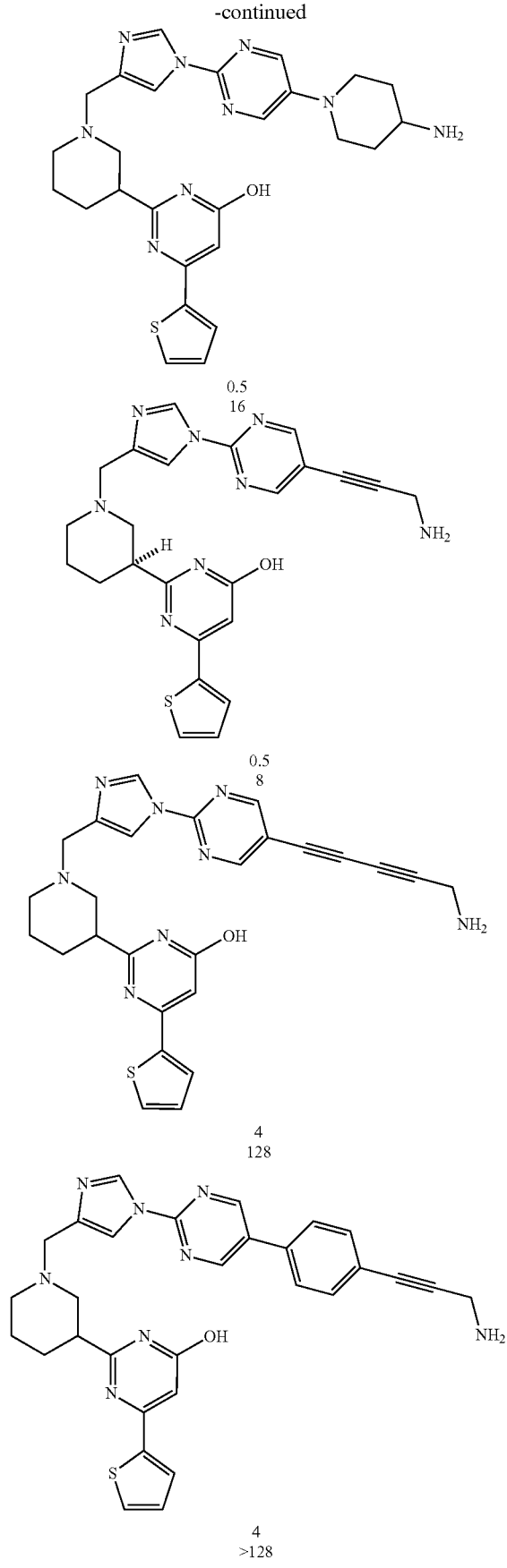
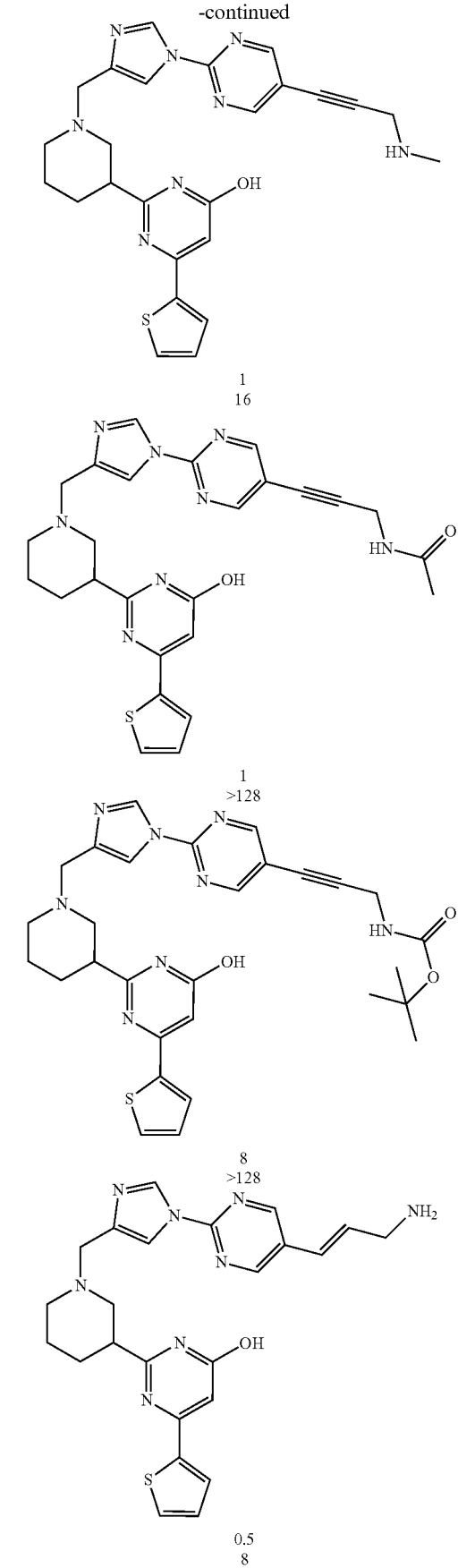

117
-continued
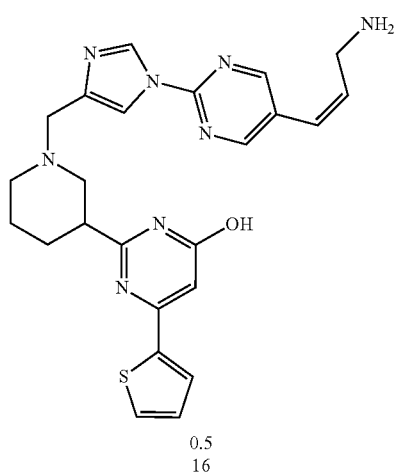
0.5
16
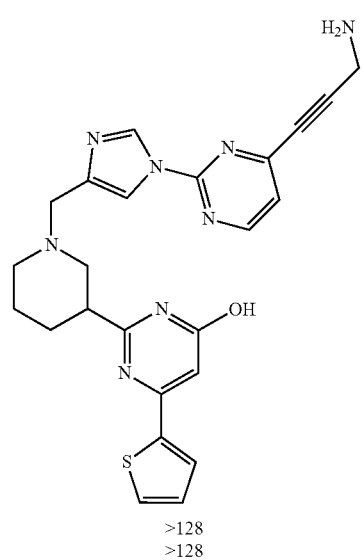
>128
>128
MIC(μg/mL) in *E. coli* ΔTolC
MIC(μg/mL) in *E. coli* MG1655
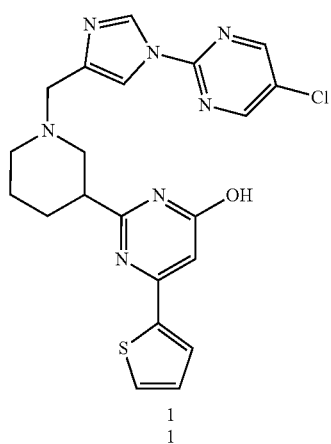
1
1
118
-continued
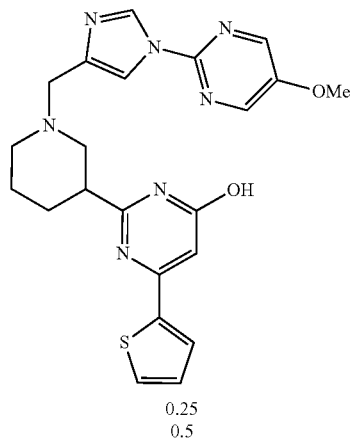
0.25
0.5
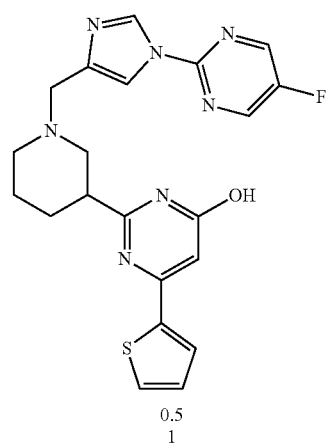
0.5
1
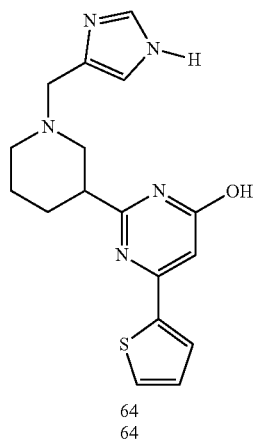
64
64

119
-continued
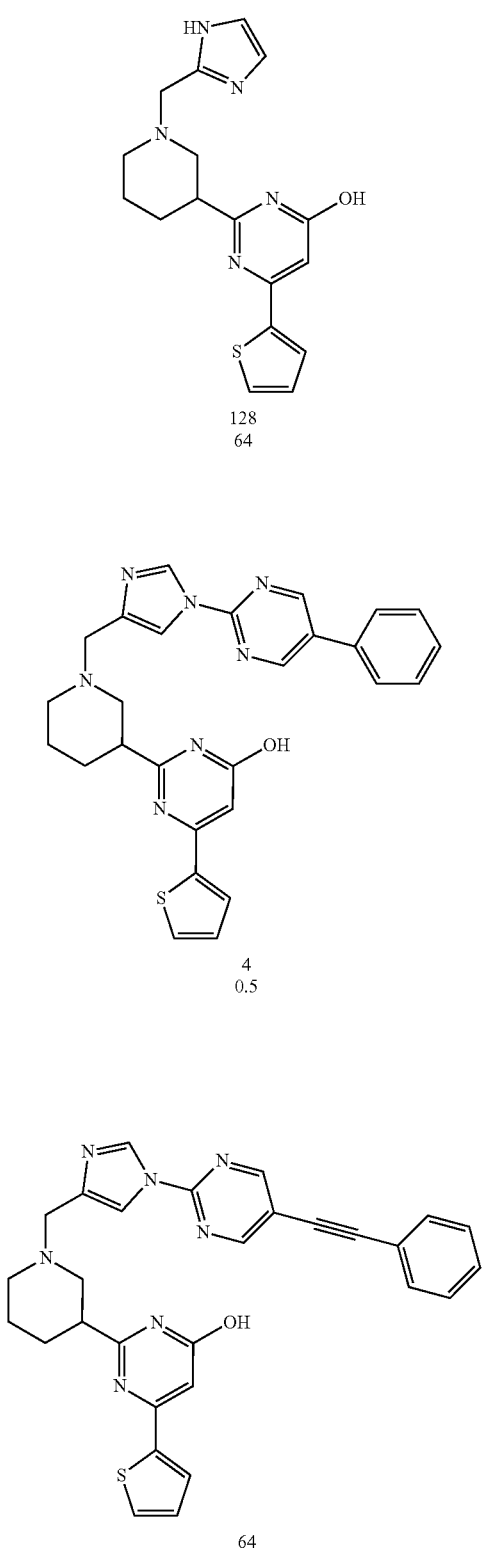
128
64
4
0.5
64
128
MIC(μg/mL) in *S. aureus* ATCC 29213
MIC(μg/mL) in *E. coli* ΔTolC
120
-continued
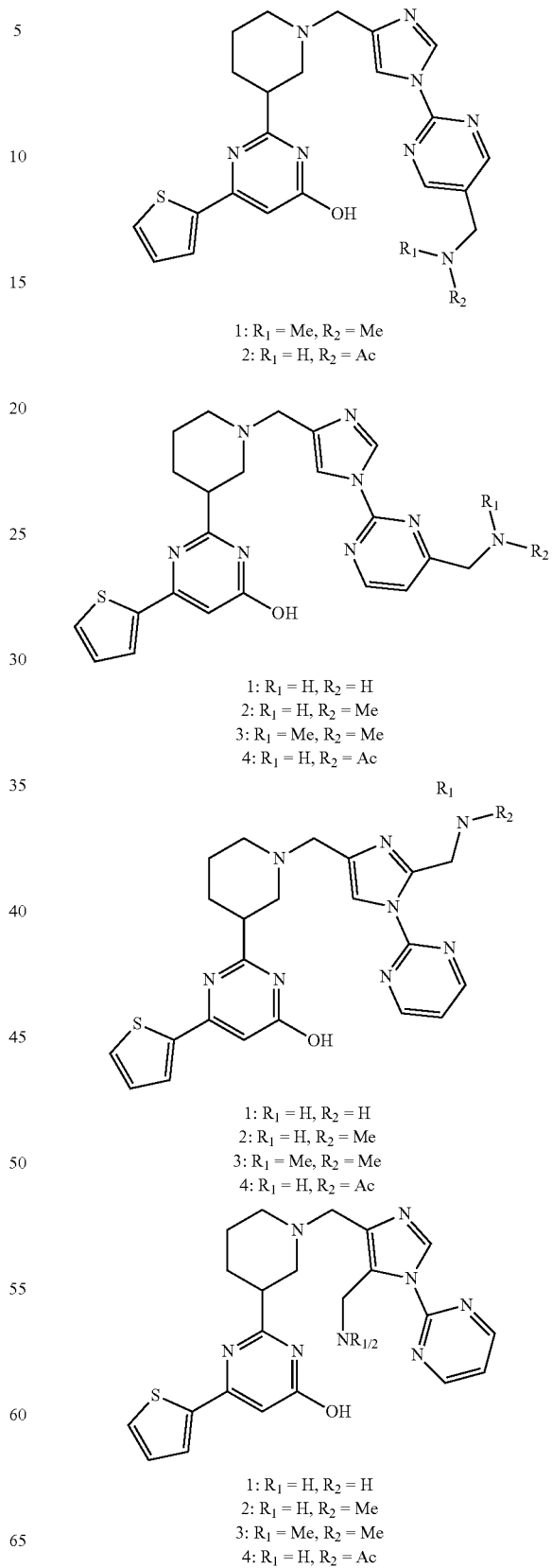
1: R₁ = Me, R₂ = Me
2: R₁ = H, R₂ = Ac
1: R₁ = H, R₂ = H
2: R₁ = H, R₂ = Me
3: R₁ = Me, R₂ = Me
4: R₁ = H, R₂ = Ac
1: R₁ = H, R₂ = H
2: R₁ = H, R₂ = Me
3: R₁ = Me, R₂ = Me
4: R₁ = H, R₂ = Ac
1: R₁ = H, R₂ = H
2: R₁ = H, R₂ = Me
3: R₁ = Me, R₂ = Me
4: R₁ = H, R₂ = Ac 121
-continued
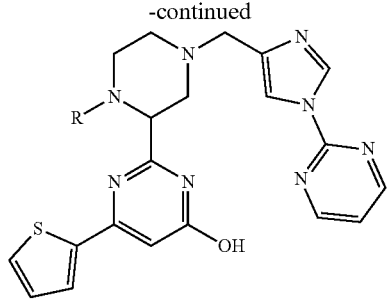
1: R = H
2: R = Me
3: R = Ac
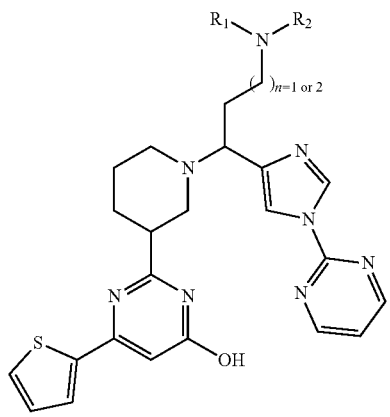
1: $R_1$ = H, $R_2$ = H
2: $R_1$ = H, $R_2$ = Me
3: $R_1$ = Me, $R_2$ = Me
4: $R_1$ = H, $R_2$ = Ac
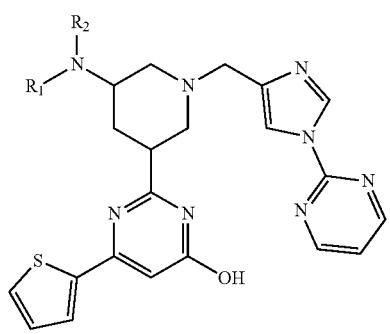
1: $R_1$ = H, $R_2$ = H
2: $R_1$ = H, $R_2$ = Me
3: $R_1$ = Me, $R_2$ = Me
4: $R_1$ = H, $R_2$ = Ac
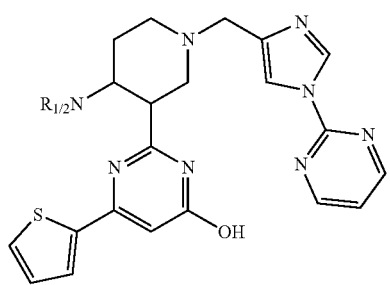
1: $R_1$ = H, $R_2$ = H
2: $R_1$ = H, $R_2$ = Me
3: $R_1$ = Me, $R_2$ = Me
4: $R_1$ = H, $R_2$ = Ac
122
-continued
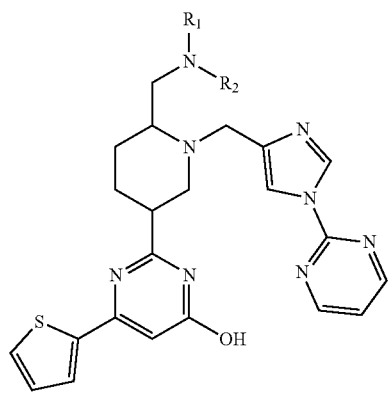
1: $R_1$ = H, $R_2$ = H
2: $R_1$ = H, $R_2$ = Me
3: $R_1$ = Me, $R_2$ = Me
4: $R_1$ = H, $R_2$ = Ac
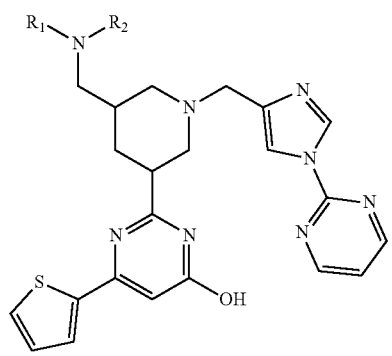
1: $R_1$ = H, $R_2$ = H
2: $R_1$ = H, $R_2$ = Me
3: $R_1$ = Me, $R_2$ = Me
4: $R_1$ = H, $R_2$ = Ac
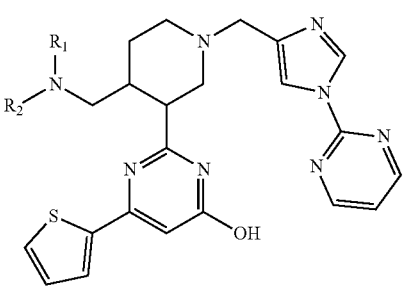
1: $R_1$ = H, $R_2$ = H
2: $R_1$ = H, $R_2$ = Me
3: $R_1$ = Me, $R_2$ = Me
4: $R_1$ = H, $R_2$ = Ac -continued

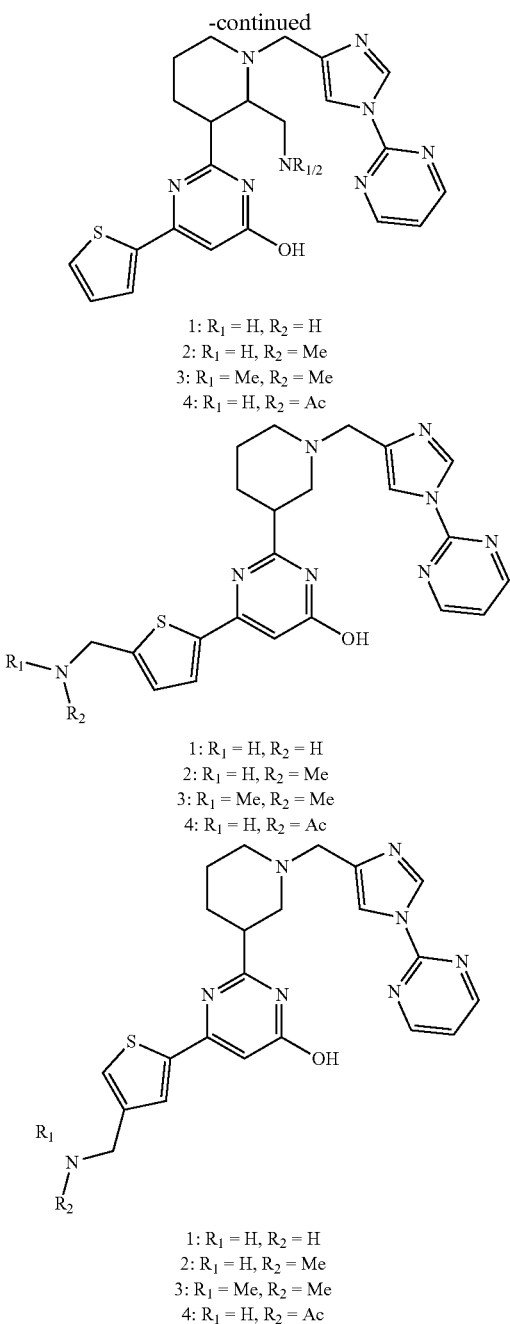

1: R₁ = H, R₂ = H
2: R₁ = H, R₂ = Me
3: R₁ = Me, R₂ = Me
4: R₁ = H, R₂ = Ac

1: R₁ = H, R₂ = H
2: R₁ = H, R₂ = Me
3: R₁ = Me, R₂ = Me
4: R₁ = H, R₂ = Ac

1: R₁ = H, R₂ = H
2: R₁ = H, R₂ = Me
3: R₁ = Me, R₂ = Me
4: R₁ = H, R₂ = Ac

-continued

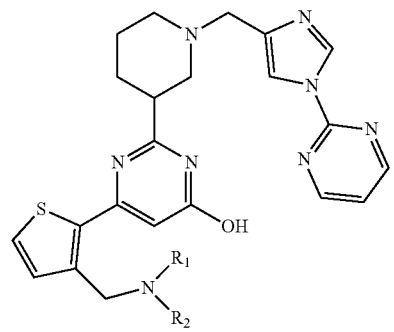

1: R₁ = H, R₂ = H
2: R₁ = H, R₂ = Me
3: R₁ = Me, R₂ = Me
4: R₁ = H, R₂ = Ac

Alternative R₁, R₂ substituents on compounds of Example 3-2:

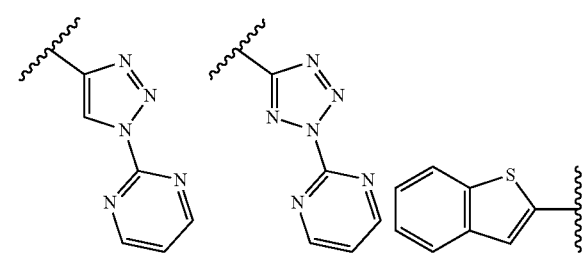

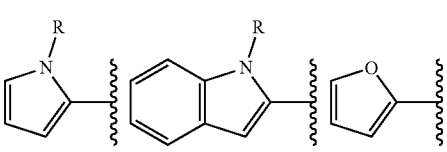

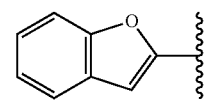

Example 4: Biological Activity Data

TABLE 5A

Bioactivity of Select Compounds against Exemplary Strains of Bacteria.

| Strain: | 1 | 2 | 3 | 4 | 5 | 6 | 7 | 8 | 9 | 10 | 11 | 12 |
|---|---|---|---|---|---|---|---|---|---|---|---|---|
| Debio-1452 | 4 | >32 | 16 | >32 | >32 | >32 | 0.03 | 1 | 8 | 4 | >32 | 0.004 |
| E9 | 2 | 4 | 4 | 32 | 4 | 4 | 0.06 | 0.5 | 4 | 1 | >64 | 0.03 |
| E26 | | | | | >64 | >64 | 4 | >8 | >64 | >64 | >64 | 1 |
| E21 | | | | | 32 | 32 | 0.5 | 2 | 16 | >64 | >64 | 0.5 |
| E13 | 2 | | | | 4 | 8 | 0.125 | 0.5 | 4 | 8 | >64 | 0.03 |
| E17 | 4 | | | | 32 | 8 | 0.06 | 0.5 | 8 | 16 | >64 | 0.125 |
| E12 | >64 | | | | >64 | >64 | <0.125 | | >64 | >64 | >64 | 0.03 |
| E29 | >64 | | | | >64 | | | | | >64 | | >64 |
| Ribocil-C | | | | | | >256 | 0.25 | | | | | 0.5 |
| R13a | 16 | 16 | >128 | 64 | 8 | 16* | 2* | 8* | | | | 16* |
| R18 | | | | | | 16 | 2 | 8 | | | | 4 |

TABLE 5A-continued

Bioactivity of Select Compounds against Exemplary Strains of Bacteria.

| Strain: | 1 | 2 | 3 | 4 | 5 | 6 | 7 | 8 | 9 | 10 | 11 | 12 |
|---|---|---|---|---|---|---|---|---|---|---|---|---|
| R12a |  |  |  |  |  | >256 |  |  |  |  |  | >256 |
| R13b |  |  |  |  |  | 64 |  |  |  |  |  | 64 |
| Z3 | >64 | >64 | 32 | >64 | >64 | >64 | 2 | 2 | >64 | 4 | >64 | 4 |
| Z7 | 2 | 4 | 2 | >32 | 16 |  |  |  |  |  |  |  |
| Z14 | 8 | 8 | 8 | 64 | 8 | 4 |  |  | 8 | 8 | 32 | 4 |
| Z15 |  |  |  |  | 16 | 8 |  |  |  | 8 | 16 | 4 |
| Z11 |  |  |  |  | >64 | 21 |  |  |  | 8 | >64 | 16 |
| Z16 |  |  |  |  | >64 | >64 |  |  | >64 | >64 | >64 | 32 |

TABLE 5B

Key to Table 5A.

| Strain Number Column: | Strain |
|---|---|
| 1 | *E. coli* ATCC25922 |
| 2 | *E. coli* BAA-2469 |
| 3 | *A. baumannii* BAA-2093 |
| 4 | *K. pneumoniae* BAA-2146 |
| 5 | *E. cloacae* ATCC29893 |
| 6 | *E. coli* MG1655 |
| 7 | *E. coli* ΔtolC |
| 8 | *E. coli* ΔrfaC |
| 9 | *K. pneumoniae* ATCC27736 |
| 10 | *A. baumannii* ATCC19606 |
| 11 | *P. aeruginosa* PAO1 |
| 12 | *S. aureus* ATCC29213 |

The activity of other antibacterial compounds is disclosed in WO 2017/156519, the contents of which is hereby incorporated by reference in its entirety.

Example 5: Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
|  | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
|  | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q. s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl mono stearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound of Formula Ia or Formula Ib:

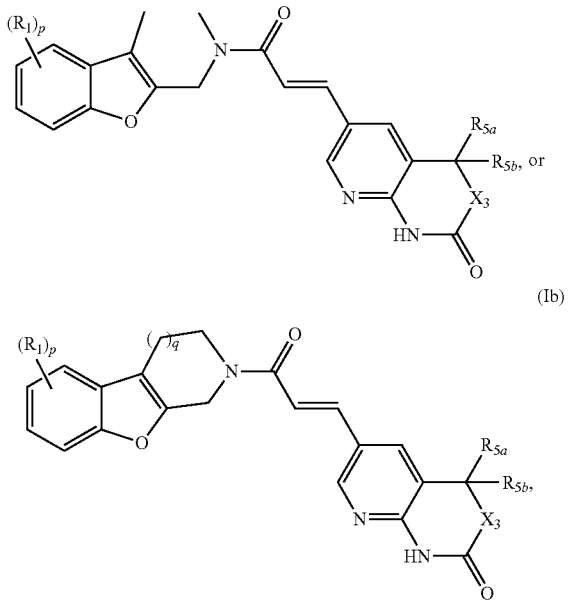

or a pharmaceutically acceptable salt thereof;
wherein
$X_3$ is selected from the group consisting of $C(R_{8a})(R_{8b})$ and $N(R_9)$;
each $R^1$ is independently selected from the group consisting of halogen, hydroxyl, —O($C_1$-$C_6$)alkyl, nitro, cyano, cycloalkyl, heterocyclyl, aryl, heteroaryl, aralkyl, and heteroaralkyl;
$R_{5a}$ and $R_{5b}$ are each independently selected from the group consisting of hydrogen, and —($C_1$-$C_6$)alkyl; or together $R_{5a}$ and $R_{5b}$ form an oxo;
$R_{8a}$ is hydrogen;
$R_{8b}$ is selected from the group consisting of $N(R_{12a})(R_{12b})$, and —(($C_1$-$C_6$)alkylene)$N(R_{12a})(R_{12b})$;
$R_9$ is —(($C_1$-$C_6$)alkylene)$N(R_{12a})(R_{12b})$;
$R_{12a}$ and $R_{12b}$ are each independently selected from the group consisting of hydrogen, —($C_1$-$C_6$)alkyl, —C(O)($C_1$-$C_6$)alkyl, and C(O)O($C_1$-$C_6$)alkyl;
p is an integer from 0-5; and
q is an integer from 1-4.

2. The compound of claim 1 wherein the compound is represented by Formula Ia:

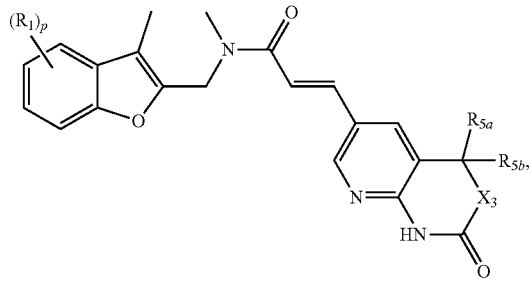

or a pharmaceutically acceptable salt thereof.

3. The compound of claim 1 wherein $X_3$ is $C(R_{8a})(R_{8b})$.

4. The compound of claim 3 wherein $R_{8b}$ is $N(R_{12a})(R_{12b})$.

5. The compound of claim 3 wherein $R_{8b}$ is —(($C_1$-$C_6$)alkylene)$N(R_{12a})(R_{12b})$.

6. The compound of claim 1 wherein at least one of $R_{12a}$ and $R_{12b}$ is hydrogen.

7. The compound of claim 1 wherein at least one of $R_{12a}$ and $R_{12b}$ is $C_1$-$C_6$alkyl, C(O)($C_1$-$C_6$)alkyl or C(O)O($C_1$-$C_6$)alkyl.

8. The compound of claim 1 wherein p is 1.

9. The compound of claim 1 wherein the compound is selected from the group consisting of:

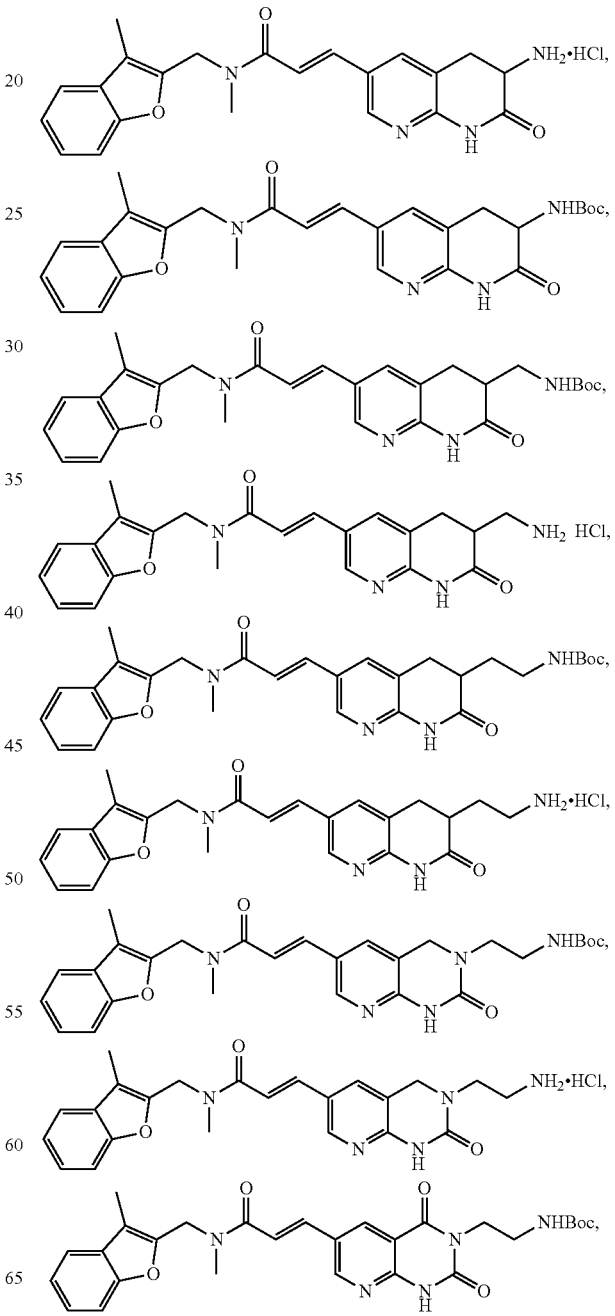

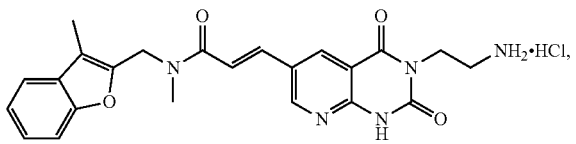

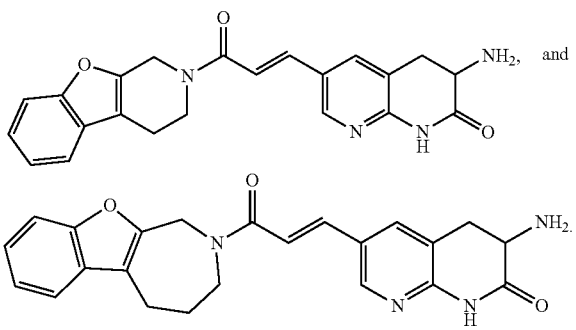

10. The compound of claim 1 wherein the compound is Debio-1425-NH2, 2, or 3:

(Debio-1425-NH2)

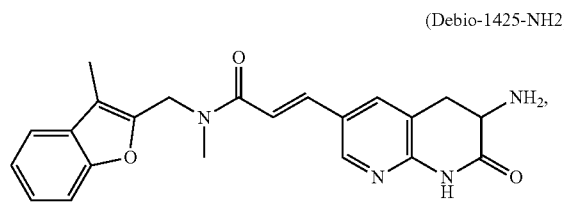

(2)

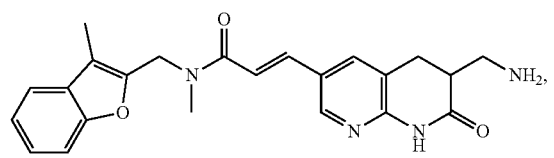

(3)

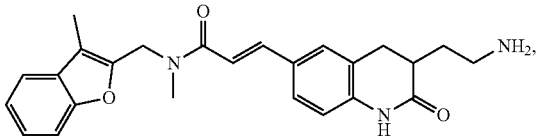

or a pharmaceutically acceptable salt thereof.

11. The compound of claim 1 wherein the compound is Debio-1425-NH2:

(Debio-1425-NH2)

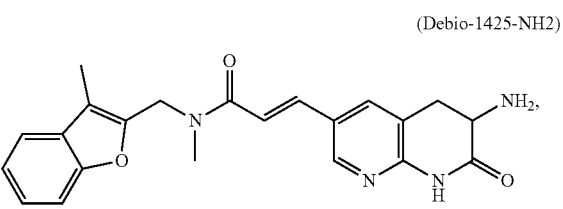 [SMILES: Cc1c(CN(C)C(=O)/C=C/c2cnc3c(c2)CC(N)C(=O)N3)oc2ccccc12]

or a pharmaceutically acceptable salt thereof.

12. A pharmaceutical composition comprising a compound of claim 1 and a pharmaceutically acceptable excipient.

13. A method of antimicrobial treatment comprising administering to a subject in need thereof a therapeutically effective amount of a compound of claim 1, thereby killing or inhibiting growth of a microorganism in the subject.

14. The method of claim 13 wherein the microorganism is a Gram-negative bacterium.

15. The method of claim 13 wherein the microorganism is at least one bacterium selected from the group consisting of *Acinetobacter*, Bacilli, *Bordetella, Borrelia, Brucella, Burkholderia, Campylobacter, Chlamydia, Clostridium*, Conococcus, *Corynebacterium, Enterobacter, Enterococcus, Erwinia, Escherichia, Francisella, Haemophilus*, Heliobacter, *Klebsiella, Legionella, Leptospira, Listeria*, meningococcus, *Mycobacterium, Mycoplasma, Neisseria, Pasteurella, Pelobacter*, Pneumonococcus, *Proteus, Pseudomonas, Rickettsia, Salmonella, Serratia, Shigella, Staphylococcus, Streptococcus, Treponema, Vibrio, Yersinia* and *Xanthomonas*.

\* \* \* \* \*